(12) United States Patent
Bar-Or

(10) Patent No.: US 8,188,215 B2
(45) Date of Patent: *May 29, 2012

(54) METAL-BINDING COMPOUNDS AND USES THEREFOR

(76) Inventor: David Bar-Or, Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/100,854

(22) Filed: May 4, 2011

(65) Prior Publication Data

US 2011/0212902 A1    Sep. 1, 2011

Related U.S. Application Data

(60) Continuation of application No. 12/562,136, filed on Sep. 18, 2009, now Pat. No. 7,973,008, which is a division of application No. 10/076,071, filed on Feb. 13, 2002, now Pat. No. 7,592,304, which is a continuation-in-part of application No. 09/678,202, filed on Sep. 29, 2000, now abandoned.

(60) Provisional application No. 60/283,507, filed on Apr. 11, 2001, provisional application No. 60/281,648, filed on Apr. 4, 2001, provisional application No. 60/509,045, filed on Mar. 22, 2001, provisional application No. 60/268,558, filed on Feb. 13, 2001, provisional application No. 60/211,078, filed on Jun. 13, 2000, provisional application No. 60/157,404, filed on Oct. 1, 1999.

(51) Int. Cl.
*A61K 38/00*    (2006.01)

(52) U.S. Cl. .............................. 530/300; 514/2

(58) Field of Classification Search ........................ None
See application file for complete search history.

(56) References Cited

U.S. PATENT DOCUMENTS

| | | |
|---|---|---|
| 3,853,838 A | 12/1974 | Greven |
| 3,862,928 A | 1/1975 | De Wied et al. |
| 4,022,833 A | 5/1977 | Diana et al. |
| 4,025,499 A | 5/1977 | Thomas |
| 4,046,633 A | 9/1977 | Keutel |
| 4,085,096 A | 4/1978 | Tinney et al. |
| 4,323,558 A | 4/1982 | Nelson |
| 4,412,988 A | 11/1983 | Gasc et al. |
| 4,438,029 A | 3/1984 | Erickson et al. |
| 4,461,724 A | 7/1984 | Konishi |
| 4,591,648 A | 5/1986 | Jones et al. |
| 4,628,045 A | 12/1986 | Hahn |
| 4,636,382 A | 1/1987 | Hemestam et al. |
| 4,665,054 A | 5/1987 | Pickart |
| 4,684,624 A | 8/1987 | Hosobuchi et al. |
| 4,725,576 A | 2/1988 | Pollock et al. |
| 4,746,649 A | 5/1988 | Raddatz et al. |
| 4,760,051 A | 7/1988 | Pickart |
| 4,767,753 A | 8/1988 | Pickart |
| 4,810,693 A | 3/1989 | Pickart |
| 4,816,449 A | 3/1989 | Hahn |
| 4,877,770 A | 10/1989 | Pickart |
| 4,880,778 A | 11/1989 | Bowers et al. |
| 4,885,156 A | 12/1989 | Kotilainen et al. |
| 4,912,118 A | 3/1990 | Hider et al. |
| 4,952,395 A | 8/1990 | Shinnick et al. |
| 4,975,423 A | 12/1990 | Gaffar |
| 5,023,237 A | 6/1991 | Pickart |
| 5,032,384 A | 7/1991 | Yeh et al. |
| 5,051,406 A | 9/1991 | Satoh |
| 5,059,537 A | 10/1991 | Pedroni et al. |
| 5,059,588 A | 10/1991 | Pickart |
| 5,087,696 A | 2/1992 | Parker et al. |
| 5,093,117 A | 3/1992 | Lawrence et al. |
| 5,101,041 A | 3/1992 | Troutner et al. |
| 5,104,865 A | 4/1992 | Hider et al. |
| 5,118,665 A | 6/1992 | Pickart |
| 5,120,831 A | 6/1992 | Pickart |
| 5,128,122 A | 7/1992 | Cerami et al. |
| 5,135,913 A | 8/1992 | Pickart |
| 5,145,838 A | 9/1992 | Pickart |
| 5,147,632 A | 9/1992 | Pan et al. |
| 5,149,540 A | 9/1992 | Kunihiro et al. |
| 5,157,632 A | 10/1992 | Tsutsui |
| 5,158,884 A | 10/1992 | Conti-Tronconi et al. |
| 5,164,367 A | 11/1992 | Pickart |
| 5,171,564 A | 12/1992 | Nathoo et al. |

(Continued)

FOREIGN PATENT DOCUMENTS

DE     4028957     3/1992

(Continued)

OTHER PUBLICATIONS

U.S. Appl. No. 09/678,202, filed Sep. 29, 2000, Bar-Or. U.S. Appl. No. 13/100,870, filed May 4, 2011, Bar-Or.
U.S. Appl. No. 13/110,550, filed May 18, 2011, Bar-Or.
"Angiogenesis Inhibitors," found at //www.cancerprotocol.com/angiogenesis_inhbitiors.html, Jan. 28, 2002, 1 page.
"Capsules SYPRINE® (Trientine Hydrochloride)," Merck & Co., Inc., Whitehouse Station, NJ; Jan. 2001, [online] [retrieved on Jun. 6, 2002] Retrieved from the Internet: <URL: //www.ncbi.nlm.nih.gov/entrez/query.fcgi? cmd=Retrieve&db=PubMed&list_uids=860...>, 4 pages.
"Metal Heads," from New Scientist, Aug. 26, 2000, found at //purdeyenvironment.com/Full%20New%20scientist0001.htm, 6 pages.

(Continued)

*Primary Examiner* — Anand Desai
(74) *Attorney, Agent, or Firm* — Sheridan Ross P.C.

(57) ABSTRACT

The invention provides a method of reducing the damage done by reactive oxygen species (ROS) in an animal. The invention also provides a method of reducing the concentration of a metal in an animal. These methods comprise administering to the animal an effective amount of a metal-binding compound as further described in the application. The invention further provides a method of reducing the damage done by ROS to a cell, a tissue or an organ that has been removed from an animal. This method comprising contacting the cell, tissue or organ with a solution or medium containing an effective amount of a metal-binding compound of the invention. The invention further provides novel metal-binding compounds, pharmaceutical compositions comprising the metal-binding compounds, and kits comprising a container holding a metal-binding compound of the invention.

20 Claims, 29 Drawing Sheets

U.S. PATENT DOCUMENTS

| | | | |
|---|---|---|---|
| 5,177,061 A | 1/1993 | Pickart | |
| 5,200,320 A | 4/1993 | Sette et al. | |
| 5,214,032 A | 5/1993 | Pickart | |
| 5,227,307 A | 7/1993 | Bar-Or et al. | |
| 5,252,559 A | 10/1993 | Kronholm et al. | |
| 5,256,559 A | 10/1993 | Maraganore et al. | |
| 5,270,447 A | 12/1993 | Liotta et al. | |
| 5,286,479 A | 2/1994 | Garlich et al. | |
| 5,288,479 A | 2/1994 | Gorman et al. | |
| 5,290,519 A | 3/1994 | Bar-Or et al. | |
| 5,298,237 A | 3/1994 | Fine | |
| 5,348,943 A | 9/1994 | Pickart | |
| 5,360,338 A | 11/1994 | Waggoner | |
| 5,380,747 A | 1/1995 | Medford et al. | |
| 5,382,431 A | 1/1995 | Pickart | |
| 5,422,096 A | 6/1995 | Lauffer et al. | |
| 5,455,229 A | 10/1995 | Hahn et al. | |
| 5,468,777 A | 11/1995 | France et al. | |
| 5,470,876 A | 11/1995 | Proctor | |
| 5,476,647 A | 12/1995 | Chow et al. | |
| 5,476,939 A | 12/1995 | Johnson | |
| 5,503,987 A | 4/1996 | Wagner et al. | |
| 5,527,522 A | 6/1996 | Lauffer et al. | |
| 5,529,907 A | 6/1996 | Nierman et al. | |
| 5,538,945 A | 7/1996 | Pallenberg et al. | |
| 5,550,183 A | 8/1996 | Pickart | |
| 5,554,375 A | 9/1996 | Pickart | |
| 5,585,466 A | 12/1996 | Carter | |
| 5,591,711 A | 1/1997 | Koyama et al. | |
| 5,618,785 A | 4/1997 | Heavner et al. | |
| 5,624,900 A | 4/1997 | Suda et al. | |
| 5,628,982 A | 5/1997 | Lauffer et al. | |
| 5,631,172 A | 5/1997 | Johnson | |
| 5,631,228 A | 5/1997 | Oppenheim et al. | |
| 5,637,311 A | 6/1997 | Pallenberg | |
| 5,637,578 A | 6/1997 | Riley et al. | |
| 5,639,624 A | 6/1997 | Wagner et al. | |
| 5,650,134 A | 7/1997 | Albert et al. | |
| 5,650,307 A | 7/1997 | Sijmons et al. | |
| 5,654,160 A | 8/1997 | Johnson | |
| 5,663,301 A | 9/1997 | Johnson | |
| 5,670,627 A | 9/1997 | Johnson | |
| 5,670,645 A | 9/1997 | Johnson | |
| 5,683,907 A | 11/1997 | Johnson | |
| 5,710,123 A | 1/1998 | Heavner et al. | |
| 5,710,172 A | 1/1998 | Kukreja et al. | |
| 5,739,395 A | 4/1998 | Bergeron, Jr. | |
| 5,770,178 A | 6/1998 | Itaya et al. | |
| 5,776,892 A | 7/1998 | Counts et al. | |
| 5,780,594 A | 7/1998 | Carter | |
| 5,785,948 A | 7/1998 | Itaya et al. | |
| 5,786,335 A | 7/1998 | Cody et al. | |
| 5,807,535 A | 9/1998 | Smith et al. | |
| 5,830,489 A | 11/1998 | Valenti et al. | |
| 5,851,514 A | 12/1998 | Hassan et al. | |
| 5,858,332 A | 1/1999 | Jensen et al. | |
| 5,858,993 A | 1/1999 | Pickart | |
| 5,874,573 A | 2/1999 | Winchell et al. | |
| 5,877,277 A | 3/1999 | Coy et al. | |
| 5,885,965 A | 3/1999 | Oppenheim et al. | |
| 5,888,522 A | 3/1999 | Pickart | |
| 5,906,811 A | 5/1999 | Hersh | |
| 5,906,996 A | 5/1999 | Murphy | |
| 5,919,900 A | 7/1999 | Moyle et al. | |
| 5,922,307 A | 7/1999 | Montgomery | |
| 5,922,346 A | 7/1999 | Hersh | |
| 5,922,761 A | 7/1999 | Lai | |
| 5,932,548 A | 8/1999 | Deghenghi | |
| 5,952,395 A | 9/1999 | Lorant | |
| 5,994,339 A | 11/1999 | Crapo et al. | |
| 6,001,965 A | 12/1999 | Livant | |
| 6,004,953 A | 12/1999 | Volpin et al. | |
| 6,008,205 A | 12/1999 | Serhan et al. | |
| 6,017,888 A | 1/2000 | Pallenberg et al. | |
| 6,022,879 A | 2/2000 | Crow et al. | |
| 6,083,758 A | 7/2000 | Imperiali et al. | |
| 6,084,093 A | 7/2000 | Riley et al. | |
| 6,096,328 A | 8/2000 | Sagel et al. | |
| 6,228,347 B1 | 5/2001 | Hersh | |
| 6,254,857 B1 | 7/2001 | Hoic et al. | |
| 6,264,966 B1 | 7/2001 | Winchell et al. | |
| 6,270,781 B1 | 8/2001 | Gehlsen | |
| 6,287,541 B1 | 9/2001 | Creeth et al. | |
| 6,348,465 B1 | 2/2002 | Baker | |
| 6,355,706 B1 | 3/2002 | Rajaiah et al. | |
| 6,387,891 B2 | 5/2002 | Winchell et al. | |
| 6,399,371 B1 | 6/2002 | Falduto et al. | |
| 6,509,028 B2 | 1/2003 | Williams et al. | |
| 6,562,363 B1 | 5/2003 | Mantelle et al. | |
| 6,566,511 B2 | 5/2003 | Revenkova et al. | |
| 6,579,891 B1 | 6/2003 | Fernandez-Pol | |
| 6,583,182 B1 | 6/2003 | Winchell et al. | |
| 6,610,693 B2 | 8/2003 | Baker | |
| 6,610,821 B1 | 8/2003 | Blaschuk et al. | |
| 6,800,450 B2 | 10/2004 | Rosen et al. | |
| 6,897,243 B2 | 5/2005 | Baker et al. | |
| 7,592,304 B2 | 9/2009 | Bar-Or et al. | |
| 7,632,803 B2 | 12/2009 | Bar-Or et al. | |
| 7,973,008 B2 * | 7/2011 | Bar-Or | 530/300 |
| 2002/0009693 A1 | 1/2002 | Pelerin | |
| 2002/0037827 A1 | 3/2002 | Wang et al. | |
| 2002/0091074 A1 | 7/2002 | Wooley et al. | |
| 2003/0031630 A1 | 2/2003 | Reznick et al. | |
| 2003/0055003 A1 | 3/2003 | Bar-Or | |
| 2003/0055113 A1 | 3/2003 | Wang et al. | |
| 2003/0103913 A1 | 6/2003 | Nathoo | |
| 2003/0130185 A1 | 7/2003 | Bar-Or et al. | |
| 2003/0158111 A1 | 8/2003 | Bar-Or | |
| 2005/0002876 A1 | 1/2005 | Yukl et al. | |
| 2005/0159489 A1 | 7/2005 | Baker et al. | |
| 2010/0144644 A1 | 6/2010 | Bar-Or et al. | |

FOREIGN PATENT DOCUMENTS

| | | |
|---|---|---|
| EP | 327263 | 8/1989 |
| EP | 0471396 | 2/1992 |
| EP | 0535816 | 7/1993 |
| EP | 0613560 | 9/1994 |
| EP | 0614361 | 9/1994 |
| EP | 0658565 | 6/1995 |
| EP | 719790 | 7/1996 |
| EP | 0723773 | 7/1996 |
| JP | 02-152918 | 6/1990 |
| JP | 03-261717 | 11/1991 |
| JP | 04-159211 | 6/1992 |
| JP | 05-194165 | 8/1993 |
| JP | 05-320032 | 12/1993 |
| JP | 62-116565 | 5/1997 |
| JP | 11-124322 | 5/1999 |
| WO | WO 91/17760 | 11/1991 |
| WO | WO 92/08441 | 5/1992 |
| WO | WO 93/10459 | 5/1993 |
| WO | WO 93/10777 | 6/1993 |
| WO | WO 93/23425 | 11/1993 |
| WO | WO 94/06399 | 3/1994 |
| WO | WO 94/09808 | 5/1994 |
| WO | WO 94/14836 | 7/1994 |
| WO | WO 94/26295 | 11/1994 |
| WO | WO 95/26744 | 10/1995 |
| WO | WO 96/08232 | 3/1996 |
| WO | WO 97/44313 | 11/1997 |
| WO | WO 97/49409 | 12/1997 |
| WO | WO 98/40071 | 9/1998 |
| WO | WO 98/54138 | 12/1998 |
| WO | WO 99/00106 | 1/1999 |
| WO | WO 99/37236 | 7/1999 |
| WO | WO 99/39706 | 8/1999 |
| WO | WO 99/45907 | 9/1999 |
| WO | WO 00/13712 | 3/2000 |
| WO | WO 00/18392 | 4/2000 |
| WO | WO 00/20454 | 4/2000 |
| WO | WO 00/20840 | 4/2000 |
| WO | WO 00/21941 | 4/2000 |
| WO | WO 00/23469 | 4/2000 |
| WO | WO 00/36136 | 6/2000 |
| WO | WO 01/25265 | 4/2001 |
| WO | WO 01/79444 | 10/2001 |
| WO | WO 02/24143 | 3/2002 |

| WO | WO 02/43722 | 6/2002 |
| WO | WO 02/064620 | 8/2002 |
| WO | WO 02/064621 | 8/2002 |
| WO | WO 03/000172 | 1/2003 |

OTHER PUBLICATIONS

"The Role of Copper in the Angiogenesis Process," found at //www.cancerprotocol.com/role_of_copper.html, Jan. 28, 2002, accessed Oct. 27, 2009, 2 pages.

Adman, "Copper Protein Structures," Advances in Protein Chemistry, 1991, vol. 42, pp. 145-197.

Afanas'ev, Superoxide Ion: Chemistry and Biological Implications, vol. I, CRC Press, Boca Raton, FL, 1989, pp. 26, 51, 147, 168-196, 248-266.

Aitken, "Protein Consensus Sequence Motifs," Mol. Biotech., 1999, vol. 12, pp. 241-253.

Ames et al., "Oxidants, antioxidants, and the degenerative diseases of aging," Proc. Natl. Acad. Sci. USA, 1993, vol. 90, pp. 7915-7922.

Atanasiu et al., "Direct evidence of caeruloplasmin antioxidant properties," Mol. Cell. Biochem., 1998, vol. 189, pp. 127-135.

Atwood et al., "Dramatic Aggregation of Alzheimer AB by Cu(II) is induced by conditions representing physiological acidosis," J. Biol. Chem., 1998, vol. 273(21), pp. 12817-12826.

Aust, "Metal Ions, Oxygen Radicals and Tissue Damage," Bibl. Nutr. Dieta. Basel, Karger, 1989, No. 43, pp. 266-277.

Bal et al., "Binding of Nickel(II) and Copper(II) to the N-Terminal Sequence of Human Protamine HP2," Chem. Res. Toxicol., 1997, vol. 10(8), pp. 906-914.

Bal et al., "Mediation of Oxidative DNA Damage by Nickel(II) and Copper(II) with the N-Terminal Sequence of Human Protamine HP2," Chem. Res. Toxicol., 1997, vol. 10, pp. 915-921.

Bar-Or et al., "An Analog of the Human Albumin N-Terminus (Asp-Ala-His-Lys) Prevents Formation of Copper-Induced Reactive Oxygen Species," Biochem. Biophys. Res. Commun., 2001, vol. 284, pp. 856-862.

Bar-Or et al., "Asp-Ala-His-Lys (DAHK) Inhibits Copper-Induced Oxidative DNA Double Strand Breaks and Telomere Shortening," Biochem. Biophys. Res. Commun., 2001, vol. 282, pp. 356-360.

Bar-Or et al., "Asp-Ala-His-Lys, an analog of the human albumin N-terminus inhibits formation of copper-induced reactive oxygen species," Abstract P416 reprinted from American Peptide Society "Abstract Book" presented at 17th American Peptide Symposium, San Diego, CA, Jun. 2001, 1 page.

Bar-Or et al., "Copper inhibits activated protein C: Protective effects of human albumin and an analogue of its high-affinity copper-binding site, d-DAHK," Biochem. Biophys. Res. Commun., 2002, vol. 290, pp. 1388-1392.

Bar-Or et al., "Copper is involved in hydrogen-peroxide-induced DNA damage," Free Rad. Biol. Med., 2002, vol. 32(2), pp. 197-199.

Bar-Or et al., text of poster presented at 17th American Peptide Symposium, San Diego, California, Jun. 2001, found at //www.5z.com/aps/, printed Feb. 19, 2002, 8 pages.

Battegay, E.J., "Angiogenesis: Mechanistic Insights, Neovascular Diseases, and Therapeutic Prospects," Journal of Molecular Medicine, 1995, vol. 73, pp. 333-346.

Beaulieu et al., "Polynitroxyl albumin reduces infarct sixe in transient focal cerebral ischemia in the rat: potential mechanisms studied by magnetic resonance imaging," J. Cerebral Blood Flow and Metabolism, 1998, vol. 18, pp. 1022-1031.

Belayev et al., "Posttreatment with high-dose albumin reduces histopathological damage and improves neurological deficit following fluid percussion brain injury in rats," J. Neurotrauma, 1999, vol. 16(6), pp. 445-453.

Ben-Hamida et al., "Histamine, Xanthine Oxidase Generated Oxygen-Derived Free Radicals and Helicobacter Pylori in Gastroduodenal Inflammation and Ulceration," Inflammation Research, 1998, vol. 47, pp. 193-199.

Blok-Perkowska, "Antimicrobial Properties of Tuftsin and Its Analogs," Antimicrobial Agents and Chemotherapy, 1984, vol. 25(1), pp. 134-136.

Boggs, "Copper chelation suppresses experimental liver tumor growth," found at //www.huntsmancancer.org/content/reuters/2001/12/21/200112221scie001.html, Jan. 28, 2002, 2 pages.

Bolli, R., "Recurrent Ischemia in the Canine Heart Causes Recurrent Bursts of Free Radical Production that Have a Cumulative Effect on Contractile Function," Journal of clinical investigation, Aug. 1995, vol. 96(2), pp. 1066-1084.

Bossu et al., "Trivalent Nickel Catalysis of the Autoxidation of Nickel(II) Tetraglycine," Inorganic Chemistry, 1978, vol. 17(4), pp. 1034-1042.

Bourdon et al., "Glucose and free radicals impair the antioxidant properties of serum albumin," FASEB J., 1999, vol. 13, pp. 233-244.

Boyle et al., "Inhibition of Interleukin-8 Blocks Myocardial Ischemia-Reperfusion Injury," J. Thorac. Cardiovasc. Surg., 1998, vol. 116, pp. 114-121.

Brem, "Angiogenesis and Cancer Control: From Concept to Therapeutic Trial," available at http://www.cancerprotocol.com/loinks/moffittusf_article2.html, accessed Oct. 27, 2009, pp. 1-31.

Brewer, G. et al. "Treatment of Metastatic Cancer with Tetrathiomolybdate, and Anticopper, Antiangiogenic Agent: Phase I Study," 2000, Clinical Cancer Research, vol. 6, pp. 1-10.

Buranaprapuk et al., "Protein cleavage by transition metal complexes bearing amino acid substitutes," Biochim Biophys Acta, 1998, vol. 1387, pp. 309-316.

Bush, "Metals and neuroscience," Current Opinion in Chemical Biology, 2000, vol. 4, pp. 184-191.

Cai, Q., "Antioxidative Properties of Histidine and Its Effect on—Myocardial Injury during Ischemia/Reperfusion in Isolated Rat Heart," Journal of cardiovascular pharmacology, Jan. 1995, vol. 25(1), pp. 147-155.

Calabrese et al., "An e.p.r study of the non-equivalence of the copper sites of caeruloplasmin," Biochem. J., 1986, vol. 238, pp. 291-295.

Abstract of Cameron et al., "Neurovascular Dysfunction in Diabetic Rats. Potential Contribution of Autoxidation and Free Radicals Examined Using Transition Metal Chelating Agents," J.Clin Invest., Aug. 1995, vol. 96(2), pp. 1159-1163.

Canters et al., "Engineering type 1 copper sites in proteins," FEBS, 1993, vol. 325(1,2), pp. 39-48.

Chakrabarti, "Geometry of interaction of metal ions with histidine residues in protein structures," Protein Engineering, 1990, vol. 4(1), pp. 57-63.

Chan et al., "Site-specific N-terminal auto-degradation of human serum albumin," Eur. J. Biochem., 1995, vol. 227, pp. 524-528.

Chen, Hua-Ming, "Characterization of Antioxidative Peptides from Soybean Proteins," (Food Factors for Cancer Prevention, [International Conference on Food Factors: Chemistry and Cancer Prevention], Hamamatsu, Japan, Dec. 1995, pp. 639-641.

Chen, Hua-Ming, "Antioxidative Properties of Histidine-Containing Peptides Designed from Peptide Fragments Found in the Digests of a Soybean Protein," Journal of Agricultural and Food Chemistry, 1998, vol. 46(1), pp. 49-53.

Cobine et al. "Copper-Binding Properties of the N-Terminus of the Menkes Protein," Advances in Experimental Medicine and Biology, 1999, vol. 448, pp. 153-164.

Coddington, A., "The binding of Fe+++ to native and chemically modified human serum albumin in the presence of sodium citrate," Biochimica et Biophysica Acta, 1960, vol. 44, pp. 361-363.

Corazza et al., "1H, 13C-NMR and X-ray absorption studies of copper(I) glutathione complexes," Eur. J. Biochem., 1996, vol. 236, pp. 697-705.

Cotelle et al., "Redox chemistry of complexes of Nickel(II) with some Biologically important peptides in the presence of reduced Oxygen Species: An ESR study," J. Inorganic Biochemistry, 1992, vol. 46, pp. 7-15.

Danielsson et al.; "Nonopsonic Activation of Neutrophils by Helicobacter Pylori Is Inhibited by Rebamipide," Digestive Diseases and Sciences, Sep. 1998, Supplement, vol. 43(9), pp. 167S-173S.

Das et al., "Antioxidant Effectiveness in Ischemia-Reperfusion Tissue Injury," Methods in Enzymology, 1994, vol. 233, pp. 601-611.

Davies, "Protein Damage and Degradation by Oxygen Radicals: I. General Aspects," J. Biol. Chem., 1987, vol. 262(20), pp. 9895-9901.

Davies, "Protein Damage and Degradation by Oxygen Radicals: II. Modification of Amino Acids," J. Biol. Chem., 1987, vol. 262(20), pp. 9902-9907.

Davies, "Protein Damage and Degradation by Oxygen Radicals: III. Modification of Secondary and Tertiary Structure," J. Biol. Chem., 1987, vol. 262(20), pp. 9908-9913.

Davies, "Protein Damage and Degradation by Oxygen Radicals: IV. Degradation of Denatured Protein," J. Biol. Chem., 1987, vol. 262(20), pp. 9914-9920.

Abstract of Dubois et al., "Treatment of Wilson's Disease with Triethylene Tetramine Hydrochloride (Trientine)," J Pediatr Gastroenterol Nutr, Jan. 1990, vol. 10(1), pp. 77-81.

Duchette et al., "Copper Reduction Therapy as an Antiangiogenic Treatment for Lymphoma and other Cancers," at www.coldcure.com/html/anti_ang.html, revised Feb. 23, 2001, 23 pages.

Dunphy et al., The effects of mannitol, albumin, and cardioplegia enhancers on 24-h rat heart preservation, Am. J. Physiol., 1999, vol. 276, pp. H1591-H1598.

Farkas et al., "Studies on Transition-metal-Peptide Complexes. Part 9.+ Copper(II) Complexes of Tripeptides containing histidine," J. Chem. Soc. Dalton Trans., 1984, pp. 611-614.

Flaherty, J.T., "Myocardial Injury Mediated by Oxygen Free Radicals," Am. J. Med., 1991, vol. 91, pp. 3C79S-3C85S.

Florence, "The role of free radicals in disease," Australian and New Zealand J. Opthamol., 1995, vol. 23(1), pp. 3-7.

Fu et al., "Evidence for roles of radicals in protein oxidation in advanced human atherosclerotic plaque," Biochem. J., 1998, vol. 333, pp. 519-525.

Giannitsis, E., "Neutrophil-derived oxidative stress after myocardial ischemia induced by incremental atrial pacing," Pacing and clinical electrophysiology: PACE, Jan. 1998, vol. 21(1 Pt 2), pp. 157-162.

Guan, "Isolation and Evaluation of Nonsiderophore Cyclic Peptides from Marine Sponges," Biochemical and Biophysical Research Communications, 2001, vol. 283(4), pp. 976-981.

Gutteridge et al., Copper Salt-Dependent Hydroxyl Radical Formation Damage to Proteins acting as Antioxidants, Biochim. Biophys. Acta, 1983, vol. 759, pp. 38-41.

Halliwell and Gutteridge, Free Radicals in Biology and Medicine, Second Edition, Clarendon Press, Oxford, 1989, pp. 1-21.

Halliwell et al., "Oxygen free radicals and Iron in Relation to Biology and Medicine: Some problems and Concepts," Arch. Biochem. Biophys., 1986, vol. 246(2), pp. 501-514.

Halliwell et al., "The Antioxidants of Human Extracellular Fluids," Arch. Biochem. Biophys., 1990, vol. 280(1), pp. 1-8.

Abstract of Haque et al., "Cell Envelopes of Gram negative Bacteria: Composition, Response to Chelating Agents and Susceptibility of Whole Cells to Antibacterial Agents," J Appl Bacteriol, Feb. 1976, vol. 40(1 ), pp. 89-99.

Harford et al., "Amino Terminal Cu(II)- and Ni(II)- Binding (ATCUN) Motif of Proteins and Peptides: Metal Binding, DNA Cleavage, and other Properties," Acc. Chem. Res., 1997, vol. 30, pp. 123-130.

He et al., "Dual Role of Lys206-Lys296 Interaction in Human Transferrin N-Love: Iron-Release Trigger and Anion-Binding Site," Biochemistry, 1999, vol. 38, pp. 9704-9711.

Hensley et al., "Reactive Oxygen Species as Causal Agents in the Neurotoxicity of the Alzheimer's Disease-Associated Amyloid Beta Peptide," Ann. NY Acad. Sci., 1996, pp. 120-134.

Hersh T., Oral Care and Antioxidants [online] [retrieved on Nov. 4, 2002). Retrieved from the Internet <URL.//www.dietsearch.comlhealth/oralcare.html>.

Hirose et al., "Copper binding selectivity of N- and C-sites in serum (human)—and ovo-transferrin," Biochim. Biophys. Acta, 1996, vol. 1296, pp. 103-111.

Hisatomi et al., "Optimal Concentration of Additional Albumin in the preserved solution of Isolated donor heart," Transplantation, 1991, vol. 52(4), pp. 754-755.

Hu, G., "Copper stimulates proliferation of human endothelial cells under culture," Journal of Cellular Biochemistry, 1998, vol. 69, pp. 326-335.

Huh et al., "The effect of high-dose albumin therapy on local cerebral perfusion after transient focal cerebral ischemia in rats," Brain Res., 1998, vol. 804, pp. 105-113.

Ilnuma et al., "Role of Active Oxygen Species and Lipid Peroxidation in Mepirizole-Induced Duodenal Ulcers in Rats," Digestive Diseases and Sciences, Aug. 1998, vol. 43(8), pp. 1657-1664.

Kaplan, "Synthetic ACTH Analogue Semax Displays Nootropic-Like Activity in Humans," Neuroscience Research Communications, 1996, vol. 19(2), pp. 115-123.

Karck et al., "TPEN, A Transition Metal Chelator, Improves Myocardial Protection during Prolonged Ischemia," J Heart Lung Transplant, 1992, vol. 11, pp. 979-985.

Keller et al., "Immunochemical detection of Oxidized Proteins," Chem. Res. Toxicol., 1993, vol. 6, pp. 430-433.

Kerr et al., "An introduction to oxygen free radicals," Heart Lung, 1996, vol. 25, pp. 200-209.

Khan et al., "Hepatocyte Toxicity of Mechlorethamine and Other Alkylating Anticancer Drugs," Biochem. Pharmacol., 1992, vol. 43(9), pp. 1963-1967.

Abstract of Kida et al., "Effect of pH on Preferential Antibactierial-Activity of Ethylenediaminetetraacetic Acid (EDTA)," Nippon Saikingaku Zasshi, Jul. 1992, vol. 47(4), pp. 625-629.

Kimoto et al., "Enhancement of Antitumor Activity of Ascorbate against Ehrlich Ascites Tumor Cells by the Copper: Glycylglycylhistidine Complex," Cancer Res., 1983, vol. 43(2), pp. 824-828.

Kiyokawa, T., "Binding of Cu(II) or Zn(II) in a de novo designed triple-stranded α-helical coiled-coil toward a prototype for a metal-loenzyme," Journal of Peptide Research, 2004, vol. 63(4), pp. 347-353.

Knight, "Diseases related to oxygen-derived free radicals," Ann. Clin. Lab. Sci., 1995, vol. 25(2), pp. 111-121.

"Herpetic stomatitis," //www.myoptumhealth.com/portal/ADAM/item/Herpetic+stomatitis, Dec. 2002, 2 pages.

Koch et al. "Copper-binding motifs in catalysis, transport, detoxification, and signalling," Chemistry and Biology, Aug. 1997, vol. 4(8), pp. 549-560.

Abstract of Kodama et al., "Fate of orally Administered Triethylenetetramine Dihydrochloride: A Therapeutic Drug for Wilson's Disease," Tohoku J. Exp. Med., Jan. 1993, vol. 169(1), pp. 59-66.

Kowalik-Jankowska et al., "Copper(II) Complexes with Oligopeptides Containing Serine, Methionine or Phenylalanine Residues," Sep. 24, 1992, pp. 1184-1197.

Kowalik-Jankowska et al., "Effect of a-Hydroxymethylserine Residue on Binding Ability of Oligopeptides to Cu(2)+ Ions," J. Inorg. Biochem., 1997, vol. 66, pp. 193-196.

Kruck et al., "Molecular design to mimic the copper(II) and glycylglycyl-L-histidine-N-methyl amide and comparison with human albumin," Can. J. Chem., 1976, vol. 54, pp. 1300-1308.

Lane et al., "SPARC Is a Source of Copper-Binding Peptides that Stimulate Angiogenesis," The Journal of Cell Biology, 1994, vol. 125, pp. 929-943.

Lappin et al., "Electron Paramagnetic Resonance Studies of Nickel(III)-Oligopeptide Complexes," Inorganic Chemistry, 1978, vol. 17(6), pp. 1630-1634.

Abstract for Lau et al., "Synthesis and copper(II)-binding properties of the N-terminal peptide of human alpha-fetoprotein," Biochem J., 1989, vol. 257(3), pp. 745-750.

Laussac et al., "Characterization of the Copper(II)- and Nickel(II)-Transport Site of Human Serum Albumin. Studies of Copper(II) and Nickel(II) Binding to Peptide 1-24 of Human Serum Albumin by 13C and 1H NMR," Biochemistry, 1984, vol. 23, pp. 2832-2838.

Leeuwenburgh et al., "Markers of protein oxidation by hydroxyl radical and reactive nitrogen species in tissues of aging rats," Am J. Physiol., 1998, vol. 274, pp. R453-R461.

Legrand et al., "Structure and spatial conformation of the iron-binding sites of transferrins," Biochimie, 1988, vol. 70, pp. 1185-1195.

Abstract of Light et al., "The effect of triethylenetetramine dihydrochloride on the in vivo susceptibility of Pseudomonas aeruginosa to gentamicin," J Antibiot (Tokyo), Aug. 1979, vol. 32(8), pp. 834-838.

Abstract of Lind et al., "Oxidative inactivation of plasmin and other serine proteases by copper and ascorbate," Blood, 1993, vol. 82(5), pp. 1522-1531.

Little et al., "Treatment of acute focal cerebral ischemia with concentrated albumin," Neurosurgery, 1981, vol. 9(5), pp. 552-558.

Loban et al., "Iron-binding antioxidant potential of plasma albumin," Clinical Science, 1997, vol. 93, pp. 445-451.

Lonn, E., "Effects of oxygen free radicals and scavengers on the cardiac extracellular collagen matrix during ischemia-reperfusion," Canadian journal of cardiology, Mar. 1994, vol. 10(2), pp. 203-213.
Abstract of Love et al., "Nerve Function and Regeneration in Diabetic and Galactosaemic Rats: Antioxidant and Metal Chelator Effects," Eur J Pharmacol, Oct. 24, 1996, vol. 314(1-2), pp. 33-39.
Machonkin et al., "Spectroscopic and magnetic studies of human ceruloplasmin: identification of a redox-inactive reduced type 1 copper site," Biochemistry, 37:9570-9578 (1998).
Mack, "Design and Chemical Synthesis of a Sequence-Specific DNA-Cleaving Protein," J. Am. Chem. Soc. 110, 7572, 1988.
Malins et al., "Progression of human breast cancers to the metastatic state is linked to hydroxyl radical-induced DNA damage," Proc. Natl. Acad. Sci USA, 93:2557-2565 (1996).
Malmström et al., "The Chemical biology of Copper," Curr Op. Chem. Biol., 2:286-292 (1998).
Manjari, V, "Oxidant tress antioxidants nitric oxide and essential fatty-acids in peptic ulcer disease," Prostaglandins, leukotriences, and Essential Fatty Acids 59(6) p. 401-6, 1998.
Manso, "Simposio de Outono: Ishcemia, reperfusion and oxygen free radicals," Rev. Port. Cardiol., 11(11):997-999 (1992).
Maret et al., "Cobalt as probe and Label of Proteins," Methods in Enzymology, 1993, vol. 226, pp. 52-71.
Marx et al., "Site-specific modification of albumin by free radicals: Reaction with Copper(II) and ascorbate," Biochem. J., 1985, vol. 236, pp. 397-400.
Masuoka et al., "Intrinsic Stoichiometric Equilibrium Constants for the Binding of Zinc(II) and Copper(II) to the high affinity site of serum albumin," J. Biol. Chem., 1993, vol. 268(29), pp. 21533-21537.
Matsubara et al., "Inhibition of Human Endothelial Cell Proliferation in Vitro and Neovascularization In Vivo by D-Penicillamine," J. Clin. Invest., 1989, vol. 83, pp. 158-167.
McGuirl et al., "Copper-containing oxidases," Curr. Op. Chem. Biol., 1999, vol. 3, pp. 138-144.
Neurath, H., ed., "Metal-Binding Groups of Proteins: A. Evidence for Specific Donor Atoms," Chapter IV of the Proteins: Composition, Structure, and Function, vol. 5, Academic Press, 1970, pp. 61-99.
Miller et al., "Effects of Deferrioxamine on Iron-Catalyzed Lipid Peroxidation," Arch. Biochem. Biophys., 1992, vol. 295(2), pp. 240-246.
Abstract of Mlynarz et al., "α-Hydroxymethylserine (HMS) Makes HMS-HMS-His the Most Efficient Tripeptide Ligand for Cu2+ Ions," Speciation:98, 1998, 1 page.
Abstract of Moch et al., "Protective effects of hydroxyethyl starch-deferoxamine in early sepsis," Shock, 1995, vol. 4(6), pp. 425-432.
Abstract of Moriguchi et al., "The Copper Chelator Trientine has an Antiangiogenic Effect Against Hepatocellular Carcinoma, Possibly Through Inhibition of Interleukin-8 Production," Int J Cancer, Dec. 10, 2002, vol. 102(5), pp. 445-452.
Morikawa, Eiharu, "Treatment of Focal Cerebral Ischemia With Synthetic Oligopeptide Corresponding to Lectin Domain of Selectin," Stroke (Dallas), 1996, vol. 27(5), pp. 951-956.
Abstract of Morinushi et al., "The Relationship Between Gingivitis and Colonization by Porphyromonas Gingivalis and Actinobacillus Actinomycetemcomitans in Children," J Periodontol, Mar. 2000, vol. 71(3), pp. 403-409.
Abstract of Morita et al., "Wilson's Disease Treatment by Triethylene Tetramine Dihydrochloride (Trientine, 2HCI): Long-Term Observations," Dev Pharmacol Ther, 1992, vol. 19(1), pp. 6-9.
Mukaida et al., "Inhibition of neutrophil-mediated acute inflammatory injury by an antibody against interleukin-8 (IL-8)," Inflamm. Res., 1998, vol. 47, Supplement 3, pp. S151-S157.
Musci et al., "The State of the Copper Sites in Human Ceruloplasmin," Arch. Biochem. Biophys., 1993, vol. 306(1), pp. 111-118.
Norgaard, "Specific Neutrophil Hyporesponsiveness in Chronic Helicobacter pylori Infection," Journal of infectious diseases, 1996, vol. 174(3), pp. 544-551.
Odeh, "The Role of Reperfusion-Induced Injury in the Pathogenesis of the Crush Syndrome," N Eng. J Med, 1991, vol. 324(20), pp. 1417-1422.

O'Neill, "Hydroxyl radical production during myocardial ischemia and reperfusion in cats," American journal of physiology, Aug. 1996, vol. 271(2 Pt 2), pp. H660-H667.
Pickering et al., "X-ray absorption spectroscopy of Cuprous-Thiolate Clusters in Proteins and Model Systems," Journal of the American Chemical Society, 1993, vol. 115(21), pp. 9498-9505.
Praticò et al., "Localization of Distinct F2-Isoprostanes in Human Atherosclerotic LesIons," J. Clin. Invest., 1997, vol. 100(8), pp. 2028-2034.
Predki et al., "Further characterization of the N-terminal copper(II)- and nickel(II)-binding motif of proteins," Biochem. J., 1992, vol. 287, pp. 211-215.
Quinlan et al., "Vanadium and Copper in Clinical Solutions of Albumin and their potential to damage protein structure," J. Pharm. Sci., 1992, vol. 81(7), pp. 611-614.
Raju et al., "Ceruloplasmin, Copper Ions, and Angiogenesis," JNCI, 1982, vol. 69, pp. 1183-1188.
Rao et al., "Protection of Ischemic Heart From Reperfusion Injury of Myo-Inositol Hexaphosphate, a Natural Antioxidant," Ann. Thorac. Surg., 1991, vol. 52, pp. 908-912.
Regan, "The Design of Metal-Binding Sites in Proteins," Annu. Rev. Biophys. Biomol. Struct., 22:257-81 (1993).
Regan, "Protein design: novel metal binding sites," TIBS 20, pp. 280-285 (1995).
Remmers et al., "Protein extravasation and cellular uptake after high-dose human-albumin treatment of transient focal cerebral ischemia in rats," Brain Research, 827:237-242 (1999).
Rosenthal et al., "Prevention of Post-Ischemic Brain Lipid Conjugated Diene Production and Neurological Injury by Hydoxyethyl Starch-Conjugated Deferoxamine," Free Radical Biology & Medicine, 1992, vol. 12, pp. 29-33.
Röth, "Oxygen Free Radicals and their Clinical Implications," Acta Chirurgica Hungarica, 1997, vol. 36(1-4), pp. 302-305.
Rotilio et al., "Copper-Dependent Oxidative Stress and Neurodegeneration," Life, 2000, vol. 50, pp. 309-314.
Rupp et al., "Copper(I) and Copper(II) in complexes of biochemical significance studied by X-ray photoelectron spectroscopy," Biochim. Biophys. Acta., 1976, vol. 446, pp. 151-165.
Russell et al., "Pretreatment with polynitroxyl albumin (PNA) inhibits ischemia-reperfusion induced leukocyte-endothelial cell adhesion," Free Radical Biology & Medicine, 1998, vol. 25(2), pp. 153-159.
Rylkov et al., "Labile conformation of type 2 Cu(2)+ centres in human ceruloplasmin," Eur. J. Biochem., 1991, vol. 197, pp. 185-189.
Sadler et al., "Involvement of a lysine residue in the N-terminal Ni(2)+ and Cu(2)+ biding site of serum albumins comparison with Co(2)+, Cd(2)+ and Al(3)+," Eur. J. Biochem., 1994, vol. 220, pp. 193-200.
Abstract of Saito et al., "Triethylene Tetramine (Trien) Therapy for Wilson's Disease," Tohoku J Exp Med, May 1991, vol. 164(1), pp. 29-35.
Salvemini et al., "A Nonpeptidyl mimic of superoxide dismutase with therapeutic activity in rats," Science, 1999, vol. 286, pp. 304-306.
Sayre et al., "Redox metals and neurodegenerative disease," Current Opinion in Chemical Biology, 1999, vol. 3, pp. 220-225.
Seko, "Reduction of Rat Myocardiallschaemia/Reperfusion Injury by a Synthetic Selectin Oligopeptide," J. Pathol., 1996, vol. 178, pp. 335-342.
Shapiro, "Behcet's Disease: Immune Process and the Potential Impact of Nutritional Supplementation and Pharmaco-Nutrition," Aug. 2002, //www.angelfire.com/ma/Behcetbook/shapiro.html, 26 pages.
Shimazawa et al., "Antiangiogenic activity of tumor necrosis factor-a production regulators derived from thaliodomide," Biol. Pharm. Bull., 1999, vol. 22(2), pp. 224-226.
Si et al., "Albumin enhances Superoxide production in cultured microglia," GLIA, 1997, vol. 21, pp. 413-418.
Abstract of Siegemund et al., "Mode of Action of Triethylenetetramine Dihydrochloride on Copper Metabolism in Wilson's Disease," Acta Neurol Scand, Jun. 1991, vol. 83(6), pp. 364-366.

Smith et al., "Cytochemical demonstration of oxidative damage in alzheimer disease by immunochemical enhancement of the carbonyl reaction with 2,4-Dinitrophenylhydrazine," J. Histochem. Cytochem., 1998, vol. 46, pp. 731-735.

Sokolowska et al., "Short peptides are not reliable models of thermodynamic and kinetic properties of the N-terminal metal binding site in serum albumin," Eur. J. Biochem., 2002, vol. 269, pp. 1323-1331.

Spencer et al., "Transition Metal Chelators Reduce Directly Measured Myocardial Free Radical Production During Reperfusion," J. Cardiovasc. Pharmacol., 1998, vol. 32(3), pp. 343-348.

Stohs, "The Role of Free Radicals in Toxicity and Disease," J. Basic & Clin. Physiol. Pharmacol., 1995, vol. 6(3-4), pp. 205-229.

Sutherland et al., "Attenuation of trace element-media injury during ischaemia and reperfusion by human albumin N-terminus analogue (H4DUS60131)," Abstract P078 in Abstracts of Communications to be presented at the 10th International Congress on Cardiovascular Pharmacotherapy, Kyoto Japan, Mar. 2001, p. 63.

Sutherland et al., "Attenuation of Trace Element-Mediated Injury During Ischemia and Reperfusion by an N-Terminus Analogue of Human Albumin," J. Cardio. Pharmacol., 2002, vol. 39, pp. 722-728.

Süzer et al., "Human Albumin enriched St. Thomas Hospital Cardioplegic solution increases reperfusion injury in isolated perfused rat hearts," Pharmacol. Res., 1998, vol. 37(2), pp. 97-101.

Herbert et al., eds., The Dictionary of Immunology, 4th Edition, Academic Press, Harcourt Brace & Company, London, 1995, pp. 50, 119-120.

Luckey et al., "Toxicity and Physicochemical Properties of Metal," Chapter 4 of Metal Toxicity in Mammals: Physiologic and Chemical Basis for Metal Toxicity, Plenum Press, 1977, pp. 115-122.

Tsuruma et al., "Anti-Rat IL-8 (CINC) Monoclonal Antibody Administration Reduces Ischemia-Reperfusion Injury in Small Intestine," Trans. Pro., 1998, vol. 30, pp. 2644-2645.

Ueda et al., "Catalytic Activites and Coordination Environments of the Copper Ions in the Imidazole Clusters of Histidine-Peptides, His(His)nGLY and N-Acetyl-his(his)nGLY (n=3, 8, and 18)," Chem. Pharm. Bull., 1995, vol. 43(2), pp. 359-361.

Ueda et al., "Reactions of Copper(II)-Oligopeptide Complexes with Hydrogen Peroxide: Effects of Biological Reductants," Free Radical Biology & Medicine, 1995, vol. 18(5), pp. 929-933.

Ueda et al., "Activation of hydrogen peroxide by copper (II) complexes with some histidine-containing peptides and their SOD-like activities," J. Inorgan. Biochem., 1994, vol. 55, pp. 123-130.

Abstract of Vaara, "Agents That Increase the Permeability of the Outer Membrane," Microbiol Rev, Sep. 1992, vol. 56(3), pp. 395-411.

Valadon, "Aspects of Antigen Mimicry Revealed by Immunization with a Peptide Mimetic of Cryptococcus neoformans Polysaccharide," J. Immunol. 161, 1998, pp. 1829-1836.

Waddington et al., "Reactive oxygen species: a potential role in the pathogenesis of periodontal disease," Oral Dis., May 2000, vol. 6(3), pp. 138-151.

Abstract of Waerhaug et al., "Comparison of the effect of chlorhexidine and CuS04 on plaque formation and development of gingivitis," J Clinical Periodontology, Mar. 1984, vol. 11(3), pp. 176-180.

Waggoner et al., "The Role of Copper in Neurodegenerative Disease," Neurobiology of Disease, 1999, vol. 6, pp. 221-230.

Abstract of Walshe, "Treatment of Wilson's Disease With Trientine (Triethylene Tetramine) Dihydrochloride," Lancet, Mar. 20, 1982, vol. 1(8273), pp. 643-647.

Whittal et al., "Copper binding to octarepeat peptides of the prion protein monitored by mass spectrometry," Protein Science, 2000, vol. 9, pp. 332-343.

Windholz et al., "The Merck Index, 10th Edition," Merck & Co. Inc., 1983, p. 1382, 2 pages.

Winge et al., "Cuprous-Thiolate Polymetallic Clusters in Biology," Bioinorganic Chemistry of Copper (Book), May 31, 1993, Springer, USA, pp. 110-123.

Wolff et al., "Free radicals, lipids and protein degradation," TIBS, 1986, vol. 11, pp. 27-31.

Wysocki et al., "Peroxide plasma level in patients with coronary heart disease as a possible indicator of ischemia during exercise test," Coronary Artery Disease, 1993, vol. 4, pp. 645-647.

Yamada et al., "Degradation of Transferring and albumin by radical reactions in human plasma evaluated by immunoblot," Biochem. Mol. Biol. Intl, 1998, vol. 46(4), pp. 733-738.

Yang et al., "Fully human anti-interleukin-8 monoclonal antibodies: potential therapeutics for the treatment of inflammatory disease states," J. Leukoc. Biol., Sep. 1999, vol. 66, pp. 401-410.

Abstract of Yarze et al., "Wilson's Disease: Current Status," Am J Med, Jun. 1992, vol. 92(6), pp. 643-654.

Yoon et al., "The Role of Metal Ions in Ischemia/Reperfusion Injury in Skin Flaps," J Surg Res, 1989, vol. 46, pp. 163-165.

Yoshida et al., "Copper Chelation Inhibits Tumor Angiogenesis in the Experimental 9L Gliosarcoma Model," Neurosurgery, 1995, vol. 37(2), pp. 287-293.

Abstract of Yoshii et al., "The Copper-Chelating Agent, Trientine, Suppresses Tumor Development and Angiogenesis in the Murine Hepatocellular Carcinoma Cells," Int J Cancer., Dec. 15, 2001, vol. 94(6), pp. 768-773.

Zachariou, "Protein Selectivity in Immobilized Metal Affinity Chromatography Based on the Surface Accessibility of Aspartic and Glutamic Acid Residues," Journal of Protein Chemistry, 1995, vol. 14(6), pp. 419-430.

Zweier, J., "Direct Measurement of Free Radical Generation Following Reperfusion of Ischemic Myocardium," Proc Natl Aced Sci, 1987, vol. 84, pp. 1404-1407.

International Search Report for International (PCT) Patent Application No. PCT/US00/26952, mailed Jan. 31, 2001.

Written Opinion for International (PCT) Patent Application No. PCT/US00/26952, mailed Jun. 21, 2001.

International Preliminary Examination Report for International (PCT) Patent Application No. PCT/US00/26952, mailed Oct. 31, 2001.

Written Opinion for International (PCT) Patent Application No. PCT/US02/04275, mailed Oct. 27, 2003.

International Search Report for International (PCT) Patent Application No. PCT/US02/04275, mailed Feb. 3, 2003.

International Preliminary Examination Report for International (PCT) Patent Application No. PCT/US02/04275, mailed Feb. 19, 2004.

Supplementary Partial European Search Report for European Patent Application No. 00967163.7-2405, mailed Jul. 15, 2003.

Supplementary Partial European Search Report for European Patent Application No. 00967163.7-2405, mailed Feb. 18, 2004.

Baker, "The Effect of D-Penicillamine Under the Periodontal Membrane and Alveolar Bone of the Cat During Orthodontic Tooth Movement," J. South Calif. Dent Assoc., Jul. 1970, vol. 38(7), pp. 578-590.

Bystrom et al., "The Antibacterial Action of Sodium Hypochlorite and EDTA in 60 Cases of Endodontic Therapy," Int Endod J, Jan. 1985, vol. 18(1), pp. 35-40.

Gasmi et al., "NMR structure of neuromedin C, a neurotransmitter with an amino terminal Cu.sup.II-, Ni.sup.II-binding (ATCUN) motif," J Pept Res, Jun. 1997, vol. 49(6), pp. 500-509.

Dixon et al., "Preparation of Triethylenetetramine Dihydrochloride for the Treatment of Wilson's Disease," Lancet, Apr. 15, 1972, vol. 1(7755), p. 853.

Prince et al., "Prions are copper-binding proteins," TIBS, Jun. 1998, vol. 23, pp. 197-198.

Rogala et al., "Antibacterial Action of Complexing Compounds. II. Influence of Disodium Ethylendiaminetetraacetate (NA2EDTA) on Experimental Infection with Pseudomonas Aeruginosa in Mice," Arch Immunol Ther Exp (Warsz), 1974, vol. 22(6), pp. 791-796.

Extended European Search Report for European Patent Application No. 10183238.4, dated Mar. 24, 2011.

\* cited by examiner

Polymer—— Lys(vN and C-protected)-His(N-protected)-Ala - NH$_2$

Polymer—— Lys(vN and C-protected)-His(N-protected)-Ala - Asp (substituted with R$_1$)

\* CHIRAL CENTRE

D₁

D₂

D₃

D₄

D₅

METAL-BINDING COMPOUNDS AND USES THEREFOR

CROSS REFERENCE TO RELATED APPLICATIONS

This application is a continuation of U.S. patent application Ser. No. 12/562,136, filed Sep. 18, 2009, now U.S. Pat. No. 7,973,008, which is a divisional of U.S. patent application Ser. No. 10/076,071, filed Feb. 13, 2002, now U.S. Pat. No. 7,592,304, which is a continuation-in-part of U.S. patent application Ser. No. 09/678,202, filed Sep. 29, 2000, now abandoned. U.S. patent application Ser. No. 10/076,071 also claims the benefit of U.S. Provisional Patent Application No. 60/283,507, filed Apr. 11, 2001, U.S. Provisional Patent Application No. 60/281,648, filed Apr. 4, 2001, U.S. Provisional Patent Application No. 60/509,045, filed Mar. 22, 2001, and U.S. Provisional Patent Application No. 60/268,558, filed Feb. 13, 2001. U.S. patent application Ser. No. 09/678,202, claims the benefit of U.S. Provisional Patent Application No. 60/211,078, filed Jun. 13, 2000 and U.S. Provisional Patent Application No. 60/157,404, filed on Oct. 1, 1999. The entire disclosure of the aforementioned applications is considered to be part of the disclosure of this application and is hereby incorporated fully by reference.

FIELD OF THE INVENTION

The invention relates to a method of reducing the molecular, cellular and tissue damage done by reactive oxygen species (ROS). The invention also relates to certain compounds, especially certain peptides and peptide derivatives, that bind metal ions, particularly Cu(II). The binding of metal ions by the compounds of the invention inhibits the formation and/or accumulation of ROS and/or targets the damage done by ROS to the compounds themselves (i.e., the compounds of the invention may act as sacrificial antioxidants). The compounds of the invention can also be used to reduce the concentration of a metal in an animal in need thereof.

BACKGROUND

Reactive oxygen species (ROS) include free radicals (e.g., superoxide anion and hydroxyl, peroxyl, and alkoxyl radicals) and non-radical species (e.g., singlet oxygen and hydrogen peroxide). ROS are capable of causing extensive cellular and tissue damage, and they have been reported to play a major role in a variety of diseases and conditions. Indeed, ROS have been implicated in over 100 diseases and pathogenic conditions, and it has been speculated that ROS may constitute a common pathogenic mechanism involved in all human diseases. Stohs, *J. Basic Clin. Physiol. Pharmacol*, 6, 205-228 (1995). For reviews describing ROS, their formation, the mechanisms by which they cause cellular and tissue damage, and their involvement in numerous diseases and disorders, see, e.g., Manso, *Rev. Port. Cardiol.*, 11, 997-999 (1992); Florence, *Aust. N Z J. Opthalmol.*, 23, 3-7 (1992); Stohs, *J. Basic Clin. Physiol. Pharmacol.*, 6, 205-228 (1995); Knight, *Ann. Clin. Lab. Sci.*, 25, 111-121 (1995); Kerr et al., *Heart & Lung*, 25, 200-209 (1996); Roth, *Acta Chir. Hung.*, 36, 302-305 (1997).

Ischemia/reperfusion is the leading cause of illness and disability in the world. Cardiovascular ischemia, in which the body's capacity to provide oxygen to the heart is diminished, is the leading cause of illness and death in the United States. Cerebral ischemia is a precursor to cerebrovascular accident (stroke), which is the third leading cause of death in the United States. Ischemia also occurs in other organs (e.g., kidney, liver, lung, and the intestinal tract), in harvested organs (e.g., organs harvested for transplantation or for research (e.g., perfused organ models)), and as a result of surgery where blood flow is interrupted (e.g., open heart surgery and coronary bypass surgery). Ischemia need not be limited to one organ; it can also be more generalized (e.g., in hemorrhagic shock).

Cellular and tissue damage occur during ischemia as result of oxygen deficiency. However, the damage that occurs during ischemia is generally light compared to the severe damage that occurs upon reperfusion of ischemic tissues and organs. See, e.g., Manso, *Rev. Port. Cardiol.*, 11, 997-999 (1992); Stohs, *J. Basic Clin. Physiol. Pharmacol.*, 6, 205-228 (1995); Knight, *Ann. Clin. Lab. Sci.*, 25, 111-121 (1995); Kerr et al., *Heart & Lung*, 25, 200-209 (1996); Roth, *Acta Chir. Hung.*, 36, 302-305 (1997). ROS have been reported to be responsible for the severe damage caused by reperfusion of ischemic tissues and organs. See, e.g., Manso, *Rev. Port. Cardiol.*, 11, 997-999 (1992); Stohs, *J. Basic Clin. Physiol. Pharmacol.*, 6, 205-228 (1995); Knight, *Ann. Clin. Lab. Sci.*, 25, 111-121 (1995); Kerr et al., *Heart & Lung*, 25, 200-209 (1996); Roth, *Acta Chir. Hung.*, 36, 302-305 (1997).

Metal ions, primarily transition metal ions, can cause the production and accumulation of ROS. In particular, copper and iron ions released from storage sites are one of the main causes of the production of ROS following injury, including ischemia/reperfusion injury and injury due to heat, cold, trauma, excess exercise, toxins, radiation, and infection. Roth, *Acta Chir. Hung.*, 36, 302-305 (1997). Copper and iron ions, as well as other transition metal ions (e.g., vanadium, and chromium ions), have been reported to catalyze the production of ROS. See, e.g., Stohs, *J. Basic Clin. Physiol. Pharmacol.*, 6, 205-228 (1995); Halliwell et al., *Free Radicals In Biology And Medicine*, pages 1-19 (Oxford University 1989); Marx et al., *Biochem. J.*, 236, 397-400 (1985); Quinlan et al., *J. Pharmaceutical Sci.*, 81, 611-614 (1992). Other transition metal ions (e.g., cadmium, mercury, and nickel ions) and other metal ions (e.g., arsenic and lead ions) have been reported to deplete some of the molecules of the natural antioxidant defense system, thereby causing an increased accumulation of ROS. See, e.g., Stohs, *J. Basic Clin. Physiol. Pharmacol.*, 6, 205-228 (1995). Although it has been reported that free copper ions bind nonspecifically to the amino groups of essentially any protein (Gutteridge et al., *Biochim. Biophys. Acta*, 759, 38-41 (1983)), copper ions bound to proteins can still cause the production of ROS which damage at least the protein to which the copper ions are bound. See, e.g., Gutteridge et al., *Biochim. Biophys. Acta*, 759, 38-41 (1983); Marx et al., *Biochem. J.*, 236, 397-400 (1985); Quinlan et al., *J. Pharmaceutical Sci.*, 81, 611-614 (1992).

Albumin has been characterized as an extracellular antioxidant. See, e.g., Halliwell and Gutteridge, *Arch. Biochem. Biophys.*, 280, 1-8 (1990); Das et al., *Methods Enzymol.*, 233, 601-610 (1994); Stohs, *J. Basic Clin. Physiol. Pharmacol.*, 6, 205-228 (1995); Dunphy et al., *Am. J. Physiol.*, 276, H1591-H1598 (1999)). The antioxidant character of albumin has been attributed to several of albumin's many physiological functions, including albumin's ability to bind metals (particularly copper ions), to bind fatty acids, to bind and transport steroids, to bind and transport bilirubin, to scavenge HOCl, and others. See, e.g., Halliwell and Gutteridge, *Arch. Biochem. Biophys.*, 280, 1-8 (1990); Halliwell and Gutteridge, *Arch. Biochem. Biophys.*, 246, 501-514 (1986); Stohs, *J. Basic Clin. Physiol. Pharmacol.*, 6, 205-228 (1995); Dunphy et al., *Am. J. Physiol.*, 276, H1591-H1598 (1999)). Albumin contains several metal binding sites, including one at the N-terminus. The N-terminal metal-binding sites of several albumins, including human, rat and bovine serum albumins, exhibit high-affinity for Cu(II) and Ni(II), and the amino acids involved in the high-affinity binding of these metal ions have been identified. See Laussac et al., *Biochem.*, 23, 2832-2838 (1984); Predki et al., *Biochem. J.*, 287, 211-215 (1992); Masuoka et al., *J. Biol. Chem.*, 268, 21533-21537 (1993). It has been reported that copper bound to albumin at metal binding sites other than the high-affinity N-terminal site produce free radicals which causes extensive damage to albumin at sites dictated by the location of the "loose" metal binding sites, resulting in the characterization of albumin as a "sacrificial antioxidant." See Marx et al., *Biochem. J.*, 236, 397-400 (1985); Halliwell et al., *Free Radicals In Biology And Medicine*, pages 1-19 (Oxford University 1989); Halliwell and Gutteridge, *Arch. Biochem. Biophys.*, 280, 1-8 (1990); Quinlan et al., *J. Pharmaceutical Sci.*, 81, 611-614 (1992).

Despite the foregoing, attempts to use albumin as a treatment for cerebral ischemia have shown mixed results. It has been reported that albumin is, and is not, neuroprotective in animal models of cerebral ischemia. Compare Huh et al., *Brain Res.*, 804, 105-113 (1998) and Remmers et al., *Brain Res.*, 827, 237-242 (1999), with Little et al., *Neurosurgery*, 9, 552-558 (1981) and Beaulieu et al., *J. Cereb. Blood Flow. Metab.*, 18, 1022-1031 (1998).

Mixed results have also been obtained using albumin in cardioplegia solutions for the preservation of excised hearts. As reported in Dunphy et al., *Am. J. Physiol.*, 276, H1591-H1598 (1999), the addition of albumin to a standard cardioplegia solution for the preservation of excised hearts did not improve the functioning of hearts perfused with the solution for twenty-four hours. Hearts did demonstrate improved functioning when perfused with a cardioplegia solution containing albumin and several enhancers (insulin, ATP, corticosterone, and pyruvic acid). This was a synergistic effect, since the enhancers alone, as well as the albumin alone, did not significantly improve heart function. An earlier report of improved heart function using cardioplegia solutions containing albumin was also attributed to synergism between enhancers and albumin. See the final paragraph of Dunphy et al., *Am. J. Physiol.*, 276, H1591-H1598 (1999) and Hisatomi et al., *Transplantation*, 52, 754-755 (1991), cited therein. In another study, hearts perfused with a cardioplegia solution containing albumin increased reperfusion injury in a dose-related manner, as compared to a solution not containing albumin. Suzer et al., *Pharmacol. Res.*, 37, 97-101 (1998). Based on their study and the studies of others, Suzer et al. concluded that albumin had not been shown to be effective for cardioprotection. They further noted that the use of albumin in cardioplegia solutions could be unsafe due to possible allergic reactions and the risks associated with the use of blood products.

Finally, although albumin has been characterized as an antioxidant, it has also been reported to enhance superoxide anion production by microglia (Si et al., *GLIA*, 21, 413-418 (1997)). This result led the authors to speculate that albumin leaking through the disrupted blood brain barrier in certain disorders potentiates the production of superoxide anion by microglia, and that this increased production of superoxide anion is responsible for the pathogenesis of neuronal damage in cerebral ischemia/reperfusion and some neurodegenerative diseases.

As noted above, the N-terminal metal-binding sites of several albumins exhibit high-affinity for Cu(II) and Ni(II). These sites have been studied extensively, and a general amino terminal Cu(II)- and Ni(II)-binding (ATCUN) motif has been identified. See, e.g., Harford and Sarkar, *Acc. Chem. Res.*, 30, 123-130 (1997). The ATCUN motif can be defined as being present in a protein or peptide which has a free —$NH_2$ at the N-terminus, a histidine residue in the third position, and two intervening peptide nitrogens. See, e.g., Harford and Sarkar, *Acc. Chem. Res.*, 30, 123-130 (1997). Thus, the ATCUN motif is provided by the peptide sequence Xaa Xaa His, where Xaa is any amino acid except proline. See, e.g., Harford and Sarkar, *Acc. Chem. Res.*, 30, 123-130 (1997). The Cu(II) and Ni(II) are bound by four nitrogens provided by the three amino acids of the ATCUN motif (the nitrogen of the free —$NH_2$, the two peptide nitrogens, and an imidazole nitrogen of histidine) in a slightly distorted square planar configuration. See, e.g., Harford and Sarkar, *Acc. Chem. Res.*, 30, 123-130 (1997). Side-chain groups of the three amino acids of which the ATCUN motif consists can be involved in the binding of the Cu(II) and Ni(II), and amino acids near these three N-terminal amino acids may also have an influence on the binding of these metal ions. See, e.g., Harford and Sarkar, *Acc. Chem. Res.*, 30, 123-130 (1997); Bal et al., *Chem. Res. Toxicol.*, 10, 906-914 (1997). For instance, the sequence of the N-terminal metal-binding site of human serum albumin is Asp Ala His Lys [SEQ ID NO:1], and the free side-chain carboxyl of the N-terminal Asp and the Lys residue have been reported to be involved in the binding of Cu(II) and Ni(II), in addition to the four nitrogens provided by Asp Ala His. See Harford and Sarkar, *Acc. Chem. Res.*, 30, 123-130 (1997); Laussac et al., *Biochem.*, 23, 2832-2838 (1984); and Sadler et al., *Eur. J. Biochem.*, 220, 193-200 (1994).

The ATCUN motif has been found in other naturally-occurring proteins besides albumins, and non-naturally-occurring peptides and proteins comprising the ATCUN motif have been synthesized. See, e.g., Harford and Sarkar, *Acc. Chem. Res.*, 30, 123-130 (1997); Bal et al., *Chem. Res. Toxicol.*, 10, 906-914 (1997); Mlynarz, et al., *Speciation 98: Abstracts*. Cu(II) and Ni(II) complexes of ATCUN-containing peptides and proteins have been reported to exhibit superoxide dismutase (SOD) activity. See Cotelle et al., *J. Inorg. Biochem.*, 46, 7-15 (1992); Ueda et al., *J. Inorg. Biochem.*, 55, 123-130 (1994). Despite their reported SOD activity, these complexes still produce free radicals which damage DNA, proteins and other biomolecules. See Harford and Sarkar, *Acc. Chem. Res.*, 30, 123-130 (1997); Bal et al., *Chem. Res. Toxicol.*, 10, 915-21 (1997); Ueda et al., *Free Radical Biol. Med.*, 18, 929-933 (1995); Ueda et al., *J. Inorg. Biochem.*, 55, 123-130 (1994); Cotelle et al., *J. Inorg. Biochem.*, 46, 7-15 (1992). As a consequence, it has been hypothesized that at least some of the adverse effects of copper and nickel in vivo (e.g., causing cancer and birth defects) are attributable to the binding of Cu(II) and Ni(II) to ATCUN-containing proteins which causes the production of damaging free radicals. See Harford and Sarkar, *Acc. Chem. Res.*, 30, 123-130 (1997); Bal et al., *Chem. Res. Toxicol.*, 10, 915-921 (1997); Cotelle et al., *J. Inorg. Biochem.*, 46, 7-15 (1992). Cf. Koch et al., *Chem. & Biol.*, 4, 549-60 (1997). The damaging effects produced by a Cu(II) complex of an ATCUN-containing peptide in combination with ascorbate have been exploited to kill cancer cells in vitro and to produce anti-tumor effects in vivo. See Harford and Sarkar, *Acc. Chem. Res.*, 30, 123-130 (1997).

SUMMARY OF THE INVENTION

The invention provides a method of reducing the damage done by reactive oxygen species (ROS) in an animal. The method comprises administering to the animal an effective amount of a metal-binding peptide having the formula $P_1$-$P_2$ or a physiologically-acceptable salt thereof.

The invention further provides a method of reducing the damage done by ROS to a cell, a tissue or an organ that has been removed from an animal. This method comprises contacting the cell, tissue or organ with a solution containing an effective amount of the peptide $P_1$-$P_2$ or a physiologically-acceptable salt thereof.

The invention also provides a method of reducing the concentration of a metal in an animal in need thereof. The method comprises administering to the animal an effective amount of a metal-binding peptide having the formula $P_1$-$P_2$ or a physiologically-acceptable salt thereof.

The invention also provides a pharmaceutical composition comprising a pharmaceutically-acceptable carrier and the peptide $P_1$-$P_2$ or a physiologically-acceptable salt thereof.

In addition, the invention provides a kit for reducing the damage done by ROS to a cell, a tissue or an organ that has been removed from an animal. The kit comprises a container holding the peptide $P_1$-$P_2$.

In the formula $P_1$-$P_2$:

$P_1$ is $Xaa_1$ $Xaa_2$ His or $Xaa_1$ $Xaa_2$ His $Xaa_3$; and
$P_2$ is $(Xaa_4)_n$.

$Xaa_1$ is glycine (Gly), alanine (Ala), valine (Val), leucine (Leu), isoleucine (Ile), serine (Ser), threonine (Thr), aspartic acid (Asp), asparagine (Asn), glutamic acid (Glu), glutamine (Gln), lysine (Lys), hydroxylysine (Hylys), histidine (His), arginine (Arg), ornithine (Orn), phenylalanine (Phe), tyrosine (Tyr), tryptophan (Trp), cysteine (Cys), methionine (Met) or α-hydroxymethylserine (HMS). In addition, $Xaa_1$ can be an amino acid which comprises a δ-amino group (e.g., Orn, Lys) having another amino acid or a peptide attached to it (e.g., Gly (δ)-Orn). $Xaa_1$ is preferably Asp, Glu, Arg, Thr, or HMS. More preferably, $Xaa_1$ is Asp or Glu. Most preferably $Xaa_1$ is Asp.

$Xaa_2$ is Gly, Ala, β-Ala, Val, Len, Ile, Ser, Thr, Asp, Asn, Glu, Gln, Lys, Hylys, His, Arg, Orn, Phe, Tyr, Trp, Cys, Met or HMS. $Xaa_2$ is preferably Gly, Ala, Val, Leu, Ile, Thr, Ser, Asn, Met, His or HMS. More preferably $Xaa_2$ is Ala, Val, Thr, Ser, Leu, or HMS. Even more preferably $Xaa_2$ is Ala, Thr, Leu, or HMS. Most preferably $Xaa_2$ is Ala.

$Xaa_3$ is Gly, Ala, Val, Lys, Arg, Orn, Asp, Glu, Asn, Gln, or Trp, preferably Lys.

$Xaa_4$ is any amino acid.

Finally, n is 0-100, preferably 0-10, more preferably 0-5, and most preferably 0.

In a preferred embodiment, at least one of the amino acids of $P_1$, other than β-Ala when it is present, is a D-amino acid. Preferably, the D-amino acid is $Xaa_1$, His, or both. Most preferably all of the amino acids of $P_1$, other than β-Ala when it is present, are D-amino acids. In another preferred embodiment, at least one of the amino acids of $P_1$, other than β-Ala when it is present, is a D-amino acid, and at least 50% of the amino acids of $P_2$ are also D-amino acids. Most preferably all of the amino acids of $P_2$ are D-amino acids.

In another preferred embodiment, at least one amino acid of $P_1$ and/or $P_2$ is substituted with (a) a substituent that increases the lipophilicity of the peptide without altering the ability of $P_1$ to bind metal ions, (b) a substituent that protects the peptide from proteolytic enzymes without altering the ability of $P_1$ to bind metal ions, or (c) a substituent which is a non-peptide, metal-binding functional group that improves the ability of the peptide to bind metal ions.

The invention provides another method of reducing the damage done by ROS in an animal. The method comprises administering to the animal an effective amount of a metal-binding peptide (MBP) having attached thereto a non-peptide, metal-binding functional group. The metal-binding peptide MBP may be any metal-binding peptide, not just $P_1$-$P_2$.

The invention further provides another method of reducing the damage done by ROS to a cell, a tissue or an organ that has been removed from an animal. This method comprises contacting the cell, tissue or organ with a solution containing an effective amount of a metal-binding peptide MBP having attached thereto a non-peptide, metal-binding functional group.

The invention provides another method of reducing the concentration of a metal in an animal in need thereof. The method comprises administering to the animal an effective amount of a metal-binding peptide MBP having attached thereto a non-peptide, metal-binding functional group.

The invention also provides a pharmaceutical composition comprising a pharmaceutically-acceptable carrier and a metal-binding peptide MBP having attached thereto a non-peptide, metal-binding functional group.

The invention also provides a kit for reducing the damage done by ROS to a cell, a tissue or an organ that has been removed from an animal. The kit comprises a container holding a metal-binding peptide MBP having attached thereto a non-peptide, metal-binding functional group.

The invention provides yet another method of reducing the damage done by reactive oxygen species (ROS) in an animal. The method comprises administering to the animal an effective amount of a metal-binding peptide dimer of the formula $P_3$-L-$P_3$, wherein each $P_3$ may be the same or different and is a peptide which is capable of binding a metal ion, and L is a chemical group which connects the two $P_3$ peptides through their C-terminal amino acids. In a preferred embodiment, one or both of the two $P_3$ peptides is $P_1$.

The invention further provides a method of reducing the damage done by ROS to a cell, a tissue or an organ that has been removed from an animal. This method comprises contacting the cell, tissue or organ with a solution containing an effective amount of the metal-binding peptide dimer of the formula $P_3$-L-$P_3$.

The invention also provides a method of reducing the concentration of a metal in an animal in need thereof. The method comprises administering to the animal an effective amount of the metal-binding peptide dimer of the formula $P_3$-L-$P_3$.

The invention also provides a pharmaceutical composition comprising a pharmaceutically-acceptable carrier and the metal-binding peptide dimer of the formula $P_3$-L-$P_3$.

In addition, the invention provides a kit for reducing the damage done by ROS to a cell, a tissue or an organ that has been removed from an animal. The kit comprises a container holding the metal-binding peptide dimer of the formula $P_3$-L-$P_3$.

In addition, the invention provides a peptide having the formula $P_1$-$P_2$, or a physiologically-acceptable salt thereof, wherein at least one amino acid of $P_1$, other than β-Ala when it is present, is a D-amino acid.

Further provided by the invention is a peptide having the formula $P_1$-$P_2$, or a physiologically-acceptable salt thereof, wherein at least one amino acid of $P_1$ and/or $P_2$ is substituted with (a) a substituent that increases the lipophilicity of the peptide without altering the ability of $P_1$ to bind metal ions, (b) a substituent that protects the peptide from proteolytic enzymes without altering the ability of $P_1$ to bind metal ions, or (c) a substituent which is a non-peptide, metal-binding functional group that improves the ability of the peptide to bind metal ions.

In addition, the invention provides a peptide having the formula $P_1$-$P_2$, wherein $P_1$ is defined above, and $P_2$ is a peptide sequence which comprises the sequence of a metal-binding site.

The invention also provides a metal-binding peptide MBP having attached thereto a non-peptide, metal-binding functional group.

Finally, the invention provides the metal-binding peptide dimer of the formula $P_3$-L-$P_3$.

BRIEF DESCRIPTION OF THE DRAWINGS

In FIG. 10, -□- is saline control, and —○— is drug.

In FIG. 11, -□- is saline control, and —○— is drug.

In FIG. 12, -□- is saline control, and —○— is drug.

In FIG. 13, -□- is saline control, and —○— is drug.

In FIG. 14, -□- is saline control, and —○— is drug.

In FIG. 15A, ■=ascorbate only, ♦=copper and ascorbate, ▲=tetrapeptide (L-Asp L-Ala L-His L-Lys [SEQ ID NO:1]), copper and ascorbate (tetrapeptide/copper ratio of 1:1), X=tetrapeptide, copper and ascorbate (tetrapeptide/copper ratio of 2:1). In FIG. 15B, ♦=copper and ascorbate and ■=tetrapeptide, copper and ascorbate (tetrapeptide/copper ratio of 2:1).

In FIG. 17, ♦=ascorbate only, ♦=copper and ascorbate, Δ=tetrapeptide (L-Asp L-Ala L-His L-Lys [SEQ ID NO:1]), copper and ascorbate (tetrapeptide/copper ratio of 1:1), X=tetrapeptide, copper and ascorbate (tetrapeptide/copper ratio of 2:1).

DETAILED DESCRIPTION OF THE PRESENTLY-PREFERRED EMBODIMENTS

Figure 1A:
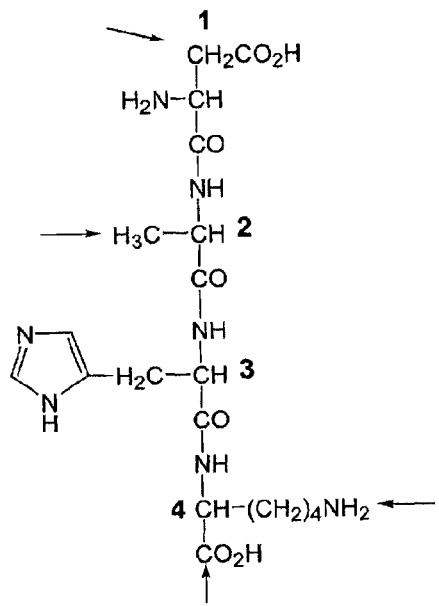
FIGS. 1A-D: Formulas of tetrapeptide Asp Ala His Lys [SEQ ID NO: 1] showing points of possible substitution.

The invention provides a peptide of the formula $P_1$-$P_2$. $P_1$ is $Xaa_1$ $Xaa_2$ His or is $Xaa_1$ $Xaa_2$ His $Xaa_3$, wherein $Xaa_1$, $Xaa_2$, and $Xaa_3$ are defined above. $P_1$ is a metal-binding peptide sequence that binds transition metal ions of Groups 1b-7b or 8 of the Periodic Table of elements (including V, Co, Cr, Mo, Mn, Ba, Zn, Hg, Cd, Au, Ag, Co, Fe, Ni, and Cu) and other metal ions (including As, Sb and Pb). The binding of metal ions by $P_1$ inhibits (i.e., reduces or prevents) the production of ROS and/or the accumulation of ROS by these metal ions and/or targets the damage done by ROS that may still be produced by the bound metal ions to the peptide itself. As a result, the damage that can be caused by ROS in the absence of the binding of the metal ions to $P_1$ is reduced. In particular, $P_1$ binds Cu(II), Ni(II), Co(II), and Mn(II) with high affinity. It should, therefore, be particularly effective in reducing the damage caused by the production and accumulation of ROS by copper and nickel.

In $P_1$, $Xaa_1$ is most preferably Asp, $Xaa_2$ is most preferably Ala, and $Xaa_3$ is most preferably Lys (see above). Thus, the preferred sequences of $P_1$ are Asp Ala His and Asp Ala His Lys [SEQ ID NO:1]. Most preferably the sequence of $P_1$ is Asp Ala His Lys [SEQ ID NO:1]. Asp Ala His is the minimum sequence of the N-terminal metal-binding site of human serum albumin necessary for the high-affinity binding of Cu(II) and Ni(II), and Lys has been reported to contribute to the binding of these metal ions to this site. Also, Asp Ala His Lys [SEQ ID NO:1] has been found by mass spectometry to bind Fe(II) and to pass through a model of the blood brain barrier. Other preferred sequences for $P_1$ include Thr Leu His (the N-terminal sequence of human α-fetoprotein), Arg Thr His (the N-terminal sequence of human sperm protamin HP2) and HMS HMS His (a synthetic peptide reported to form extremely stable complexes with copper; see Mlynarz et al., *Speciation 98: Abstracts*, Apr. 21, 1998).

$P_2$ is $(Xaa_4)_n$, wherein $Xaa_4$ is any amino acid and n is 0-100. When n is large (n>about 20), the peptides will reduce the damage done by ROS extracellularly. Smaller peptides are better able to enter cells, and smaller peptides can, therefore, be used to reduce the damage done by ROS both intracellularly and extracellularly. Smaller peptides are also less subject to proteolysis. Therefore, in $P_2$, preferably n is 0-10, more preferably n is 0-5, and most preferably n is 0. Although $P_2$ may have any sequence, $P_2$ preferably comprises a sequence which (1) binds a transition metal, (2) enhances the ability of the peptide to penetrate cell membranes and/or reach target tissues (e.g., to be able to cross the blood brain barrier), or (3) otherwise stabilizes or enhances the performance of the peptide. $P_2$ together with $P_1$ may also be the N-terminal sequence of a protein having an N-terminal metal-binding site with high affinity for copper and nickel, such as human, rat or bovine serum albumin. In the case where n=100, the peptide would have the sequence of approximately domain 1 of these albumins.

The sequences of many peptides which comprise a binding site for transition metal ions are known. See, e.g., U.S. Pat. Nos. 4,022,888, 4,461,724, 4,665,054, 4,760,051, 4,767,753, 4,810,693, 4,877,770, 5,023,237, 5,059,588, 5,102,990, 5,118,665, 5,120,831, 5,135,913, 5,145,838, 5,164,367, 5,591,711, 5,177,061, 5,214,032, 5,252,559, 5,348,943, 5,443,816, 5,538,945, 5,550,183, 5,591,711, 5,690,905, 5,759,515, 5,861,139, 5,891,418, 5,928,955, and 6,017,888, PCT applications WO 94/26295, WO 99/57262 and WO 99/67284, European Patent application 327263, Lappin et al., *Inorg. Chem.*, 17, 1630-34 (1978), Bossu et al., *Inorg. Chem.*, 17, 1634-40 (1978), Chakrabarti, *Protein Eng.*, 4, 57-63 (1990), Adman, *Advances In Protein Chemistry*, 42, 145-97 (1991), Cotelle et al., *J. Inorg. Biochem.*, 46, 7-15 (1992), Canters et al., *FEBS*, 325, 39-48 (1993), Regan, *Annu. Rev. Biophys. Biomol. Struct.*, 22, 257-281 (1993), Ueda et al., *J. Inorg. Biochem.*, 55, 123-30 (1994), Ueda et al., *Free Radical Biol. Med.*, 18, 929-33 (1995), Regan, *TIBS*, 20, 280-85 (1995), Ueda et al., *Chem. Pharm. Bull.*, 43, 359-61 (1995), Bal et al., *Chem. Res. Toxicol.*, 10, 906-914 (1997), Bal et al., *Chem. Res. Toxicol.*, 10, 915-21 (1997), Koch et al., *Chem. Biol.*, 4, 549-60 (1997), Kowalik-Jankowska et al., *J. Inorg. Biochem.*, 66, 193-96 (1997), Harford and Sarkar, *Acc. Chem. Res.*, 30, 123-130 (1997), Prince et al., *TIBS*, 23, 197-98 (1998), Mlynarz, et al., *Speciation 98: Abstracts*, and Aitken, *Molec. Biotechnol.*, 12, 241-53 (1999), Whittal et al., *Protein Science*, 9, 332-343 (2000). $P_2$ may comprise the sequence of one or more of the metal-binding sites of these peptides.

When $P_2$ comprises a metal-binding site, it preferably has a sequence which includes a short spacer sequence between $P_1$ and the metal binding site of $P_2$, so that the metal-binding sites of $P_1$ and $P_2$ may potentially cooperatively bind metal ions (similar to a 2:1 peptide:metal complex; see Example 10). Preferably, the spacer sequence is composed of 1-5, preferably 1-3, neutral amino acids. Thus, the spacer sequence may be Gly, Gly Gly, Gly Ala Gly, Pro, Gly Pro Gly, etc.

In particular, when $P_2$ comprises a metal-binding site, it preferably comprises one of the following sequences: $(Xaa_4)_m$ $Xaa_5$ $Xaa_2$ His $Xaa_3$ or $(Xaa_4)_m$ $Xaa_5$ $Xaa_2$ His. $Xaa_2$, $Xaa_3$ and $Xaa_4$ are defined above, and m is 0-5, preferably 1-3. The $Xaa_4$ amino acid(s), if present, form(s) a short spacer sequence between $P_1$ and the metal binding site of $P_2$ so that the metal-binding sites of $P_1$ and $P_2$ may cooperatively bind metal ions, and $Xaa_4$ is preferably a neutral amino acid (see the previous paragraph). $Xaa_5$ is an amino acid which comprises a δ-amino group (preferably Orn or Lys, more preferably Orn) having the $Xaa_4$ amino acid(s), if present, or $P_1$ attached to it by means of the δ-amino group. See Harford and Sarkar, *Acc. Chem. Res.*, 30, 123-130 (1997) and Shullenberger et al., *J. Am. Chem. Soc.*, 115, 11038-11039 (1993) (as a result of this means of attachment, the α-amino group of $Xaa_5$ can still participate in binding metals by means of the ATCUN motif). Thus, for instance, $P_1$-$P_2$ could be Asp Ala His Gly Gly (δ)-Orn Ala His [SEQ ID NO:2].

In addition, $P_2$ may comprise one of the following sequences: $[(Xaa_4)_m\ Xaa_5\ Xaa_2\ His\ Xaa_3]_r$, $[(Xaa_4)_m\ Xaa_5\ Xaa_2\ His]_r$, $[(Xaa_4)_m\ Xaa_5\ Xaa_2\ His\ Xaa_3\ (Xaa_4)_m\ Xaa_5\ Xaa_2\ His]_r$, and $[(Xaa_4)_m\ Xaa_5\ Xaa_2His(Xaa_4)_m\ Xaa_5\ Xaa_2\ His\ Xaa_3]_r$, wherein $Xaa_2$, $Xaa_3$, $Xaa_4$, $Xaa_5$ and m are defined and described above, and r is 2-100. In this manner metal-binding polymers may be formed.

In another preferred embodiment, $P_2$ comprises a peptide sequence that can bind Cu(I). As discussed in more detail below, Cu(II) is converted to Cu(I) in the presence of ascorbic acid or other reducing agents, and the Cu(I) reacts with oxygen to produce ROS (see equations in Examples 10 and 11). $P_1$ can bind Cu(II) tightly (see above) and is very effective by itself in inhibiting the production of ROS by copper (see Examples 7-11). However, as can be seen from the equations in Examples 10 and 11, it would be desirable to also employ a $P_2$ which could bind Cu(I).

Peptide sequences which can bind Cu(I) are known in the art. See, e.g, Pickering et al., *J. Am. Chem. Soc.,* 115, 9498-9505 (1993); Winge et al., in *Bioinorganic Chemistry Of Copper*, pages 110-123 (Karlin and Tyeklar, eds., Chapman & Hall, New York, N.Y., 1993); Koch et al., *Chem & Biol.,* 4, 549-560 (1997); Cobine et al., in *Copper Transport And Its Disorders*, pages 153-164 (Leone and Mercer eds., Kluwer Academic/Plenum Publishers, New York, N.Y., 1999). These sequences include:

```
Met Xaa4 Met,

Met Xaa4 Xaa4 Met,

Cys Cys,

Cys Xaa4 Cys,

Cys Xaa4 Xaa4 Cys,

Met Xaa4 Cys Xaa4 Xaa4 Cys,

Gly Met Xaa4 Cys Xaa4 Xaa4 Cys,      [SEQ ID NO: 7]

Gly Met Thr Cys Xaa4 Xaa4 Cys,       [SEQ ID NO: 8]
and

Gly Met Thr Cys Ala Asn Cys,         [SEQ ID NO: 9]
``` wherein $Xaa_4$ is defined above. Glutathione (γ-Glu Cys Gly) is also known to bind Cu(I). Additional Cu(I)-binding peptide sequences can be identified using a metallopeptide combinatorial library as described in, e.g., PCT application WO 00/36136. Preferably, the Cu(I)-binding peptide comprises the sequence Cys $Xaa_4$ $Xaa_4$ Cys (e.g., Gly Met $Xaa_4$ Cys $Xaa_4$ $Xaa_4$ Cys [SEQ ID NO:7], more preferably Gly Met Thr Cys $Xaa_4$ $Xaa_4$ Cys [SEQ ID NO:8], most preferably Gly Met Thr Cys Ala Asn Cys [SEQ ID NO:9]).

To enhance the ability of the $P_1$-$P_2$ peptide to penetrate cell membranes and/or reach target tissues, $P_2$ is preferably hydrophobic or an arginine oligomer (see Rouhi, *Chem. & Eng. News,* 49-50 (Jan. 15, 2001)). When $P_2$ is hydrophobic, it preferably contains 1-3 hydrophobic amino acids (e.g., Gly Gly), preferably D-amino acids. A hydrophobic $P_2$ may be particularly desirable for uses of $P_1$-$P_2$ where $P_1$-$P_2$ must cross the blood brain barrier. The arginine oligomer preferably contains 6-9 Arg residues, most preferably 6-9 D-Arg residues (see Rouhi, *Chem. & Eng. News,* 49-50 (Jan. 15, 2001). The use of a $P_2$ which is an arginine oligomer may be particularly desirable when $P_1$-$P_2$ is to be administered topically or transdermally.

The amino acids of the peptide may be L-amino acids, D-amino acids, or a combination thereof. Preferably, at least one of the amino acids of $P_1$ is a D-amino acid (preferably $Xaa_1$ and/or His), except for β-Ala, when present. Most preferably, all of the amino acids of $P_1$, other than β-Ala, when present, are D-amino acids. Also, preferably about 50% of the amino acids of $P_2$ are D-amino acids, and most preferably all of the amino acids of $P_2$ are D-amino acids. D-amino acids are preferred because peptides containing D-amino acids are resistant to proteolytic enzymes, such as those that would be encountered upon administration of the peptide to an animal (including humans) or would be present in an excised organ perfused with a solution containing the peptide. Also, the use of D-amino acids would not alter the ability of the peptide to bind metal ions, including the ability of the peptide to bind copper with high affinity.

The peptides of the invention may be made by methods well known in the art. For instance, the peptides, whether containing L-amino acids, D-amino acids, or a combination of L- and D-amino acids, may be synthesized by standard solid-phase peptide synthesis methods. Suitable techniques are well known in the art, and include those described in Merrifield, in *Chem. Polypeptides*, pp. 335-61 (Katsoyannis and Panayotis eds. 1973); Merrifield, *J. Am. Chem. Soc.,* 85, 2149 (1963); Davis et al., *Biochem. Int'l,* 10, 394-414 (1985); Stewart and Young, *Solid Phase Peptide Synthesis* (1969); U.S. Pat. Nos. 3,941,763 and 5,786,335; Finn et al., in *The Proteins,* 3rd ed., vol. 2, pp. 105-253 (1976); and Erickson et al. in *The Proteins,* 3rd ed., vol. 2, pp. 257-527 (1976). See also, Polish Patent 315474 (synthesis of HMS-containing peptides) and Shullenberger et al., *J. Am. Chem. Soc.,* 115, 1103811039 (1993) (synthesis of (δ)-Orn-containing peptides). Alternatively, the peptides may be synthesized by recombinant DNA techniques if they contain only L-amino acids. Recombinant DNA methods and suitable host cells, vectors and other reagents for use therein, are well known in the art. See, e.g., Maniatis et al., *Molecular Cloning: A Laboratory Manual*, Cold Spring Harbor, N.Y. (1982), Sambrook et al., *Molecular Cloning: A Laboratory Manual*, Cold Spring Harbor, N.Y. (1989).

Figure 1B:
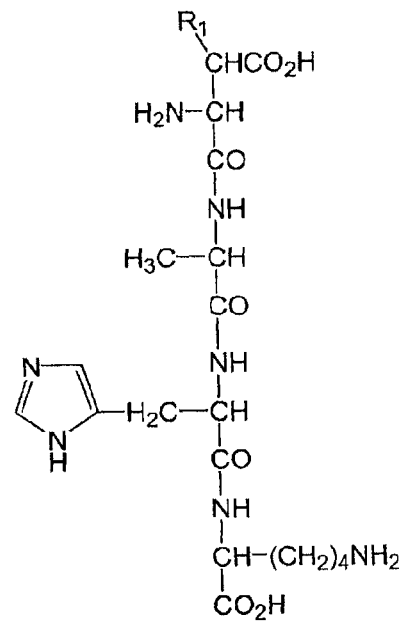
Figure 1C:
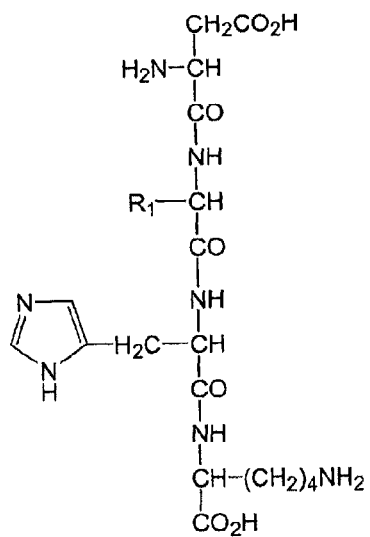
Figure 1D:
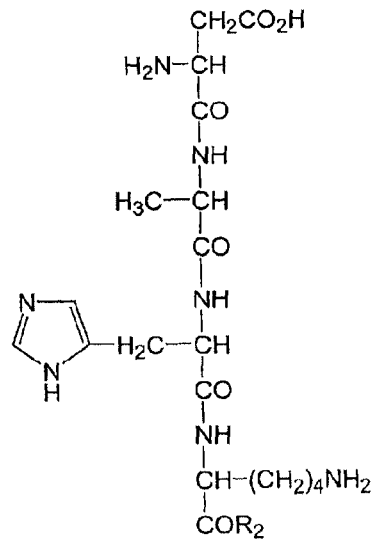

The invention further comprises derivatives of the peptide $P_1$-$P_2$, whether composed of L-amino acids, D-amino acids, or a combination of L- and D-amino acids, which are more resistant to proteolytic enzymes, more lipid soluble (to allow the peptides to more readily penetrate cell membranes and/or reach target organs, such as the brain), or both. As illustrated in FIG. 1A, $P_1$ can be modified in the regions indicated by the arrows without altering the metal binding function of $P_1$. In particular, $P_1$ can be substituted at carbons 1 or 2 with $R_1$, and the terminal —COOH of $P_1$ can be substituted with protecting group $R_2$ (FIGS. 1B-D). $P_2$ can be modified in ways similar to those described for $P_1$ to make $P_2$ more resistant to proteolytic enzymes, more lipid soluble, or both.

$R_1$ can be a straight-chain or branched-chain alkyl containing from 1 to 16 carbon atoms, and the term "alkyl" includes the R and S isomers. $R_1$ can also be an aryl or heteroaryl containing 1 or 2 rings. The term "aryl" means a compound containing at least one aromatic ring (e.g., phenyl, naphthyl, and diphenyl). The term "heteroaryl" means an aryl wherein at least one of the rings contains one or more atoms of S, N or O. These substitutions do not substantially decrease the ability of $P_1$ to bind metal ions. In particular, the ability of $P_1$ to bind copper with high affinity is not decreased by these substitutions. For instance, some of the substituents, such as a n-butyl attached to carbon 2 (see FIG. 1C, $R_1$ is n-butyl) should increase the affinity of the peptide for metal ions, such as copper, due to the inductive effect of the alkyl group. Substitution of carbon 2 (FIG. 1C) with an aryl, heteroaryl, or a long chain alkyl (about 6-16 carbon atoms) should enhance transport of the peptide across lipid membranes.

Figure 2A:
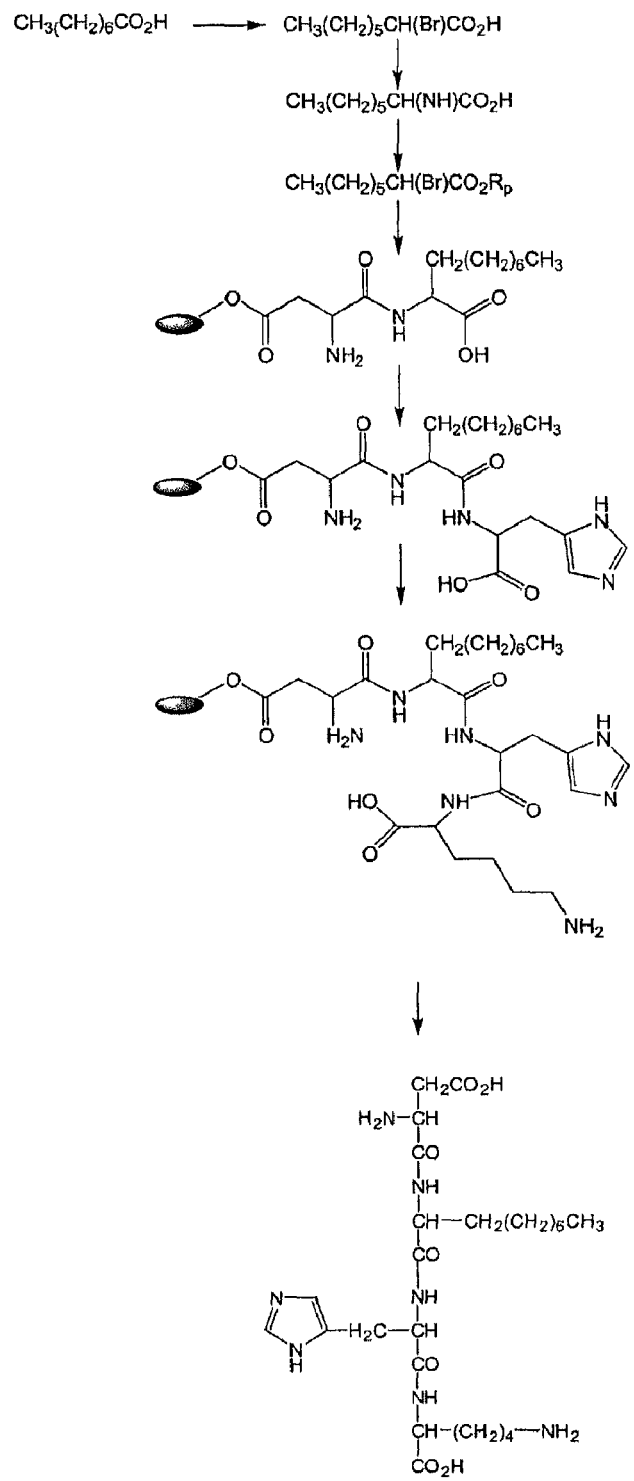
FIGS. 2A-B: Schematic diagrams of the synthesis of derivatives of the tetrapeptide Asp Ala His Lys [SEQ ID NO:1] coming within the formula of FIG. 1C (FIG. 2A) and FIG. 1B (FIG. 2B).

As noted above, methods of synthesizing peptides by solid phase synthesis are well known. These methods can be modified to prepare the derivatives shown in FIGS. 1B-C. For example, the derivative of $P_1$ illustrated in FIG. 1C, wherein $R_1$ is octyl, can be prepared as illustrated in FIG. 2A. In FIG. 2A, the elliptical element represents the polymer resin and $R_p$ is a standard carboxyl protecting group. As illustrated in FIG. 2A, octanoic acid (freshly distilled) is treated with dry bromine followed by phosphorus trichloride. The mixture is heated to about 100° C. and kept at that temperature for 4 hours. α-Bromooctanoic acid is obtained as a colorless liquid upon distillation. Amination of the bromoacid is achieved by allowing the acid and an ammonia solution to stand at 40-50° C. for 30 hours. The octyl derivative of the amino acid is obtained by removing ammonium bromide with methanol washes. Classical resolution methods give the desired optically-pure D-form. Other derivatives wherein $R_1$ is an alkyl, aryl or heteroaryl can be prepared in the manner illustrated in FIG. 2A.

Figure 2B:
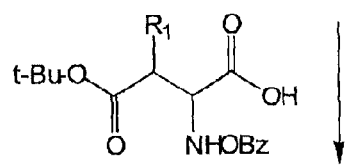

In addition, the derivative of $P_1$ illustrated in FIG. 1B, wherein $R_1$ is phenyl, can be prepared as illustrated in FIG. 2B. In FIG. 2B, Polymer is the resin, t-Bu is t-butyl, and Bz is benzyl. Other derivatives wherein $R_1$ is an alkyl, aryl or heteroaryl can be prepared in the manner illustrated in FIG. 2B.

$R_2$ can be $-NH_2$, $-NHR_1$, $-N(R_1)_2$, $-OR_1$, or $R_1$ (see FIG. 1D), wherein $R_1$ is defined above. These derivatives can be prepared as the last step of a solid-phase peptide synthesis before the peptide is removed from the resin by methods well known in the art. Substitutions with $R_2$ do not substantially decrease the ability of $P_1$ to bind metal ions.

In addition, $P_1$ and $P_2$ can be substituted with non-peptide functional groups that bind metal ions. These metal-binding functional groups can be attached to one or more pendent groups of the peptide, and the resulting peptide derivatives will possess one or more sites that are capable of binding metal ions, in addition to the binding site provided by $P_1$ and, optionally, the binding site provided by $P_2$. As a consequence, the ability of such peptide derivatives to bind metal ions is improved as compared to the corresponding unmodified peptide. For instance, the peptide derivative can bind two of the same type of metal ion instead of one (e.g., two Cu(II)), the peptide derivative can bind two different metal ions instead of one type of metal ion (e.g., one Cu(II) and one Fe(III)), or the peptide derivative can bind one metal ion better (e.g., with greater affinity) than the corresponding unmodified peptide.

Metal-binding functional groups include polyamines (e.g., diamines, triamines, etc.). Suitable diamines include 1,2-alkyldiamines, preferably alkyl diamines wherein the alkyl contains 2-10 carbon atoms (e.g., $H_2N-(CH_2)_n-NH_2$, wherein n=2-10). Suitable diamines also include 1,2-aryldiamines, preferably benzene diamines (e.g., 1,2-diaminobenzene). Suitable diamines further include 1,2-cyclic alkane diamines. "Cyclic alkanes" are compounds containing 1-3 rings, each containing 5-7 carbon atoms. Preferably the cyclic alkane diamine is 1,2-diaminocylcohexane (cyclohexane diamine).

Figure 3A:
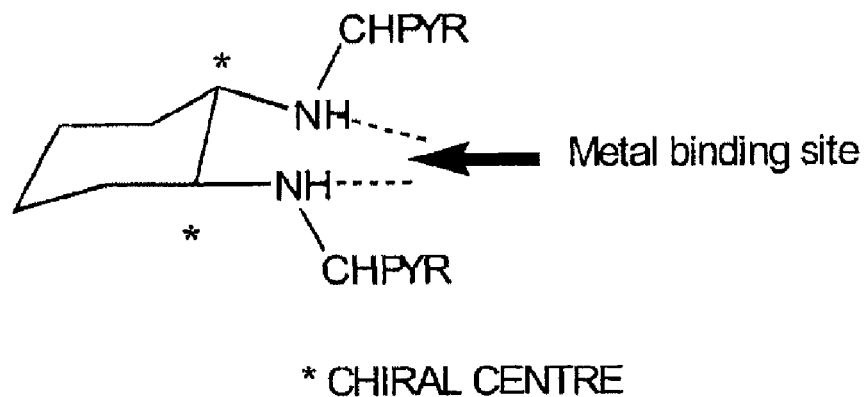
FIG. 3A-B: Formulas of cyclohexane diamine derivatives.
Figure 3B:
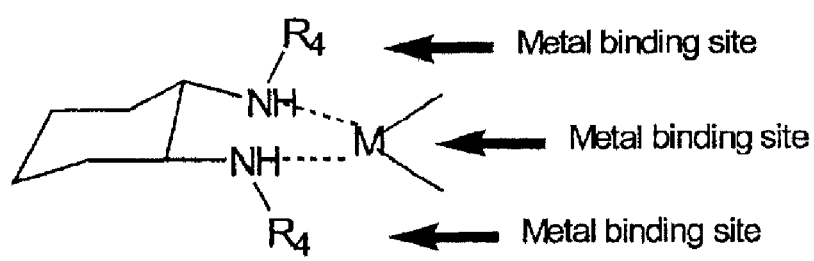

A particularly preferred diamine is 1,2-diaminocyclohexane (FIGS. 3A-B). Previous studies carried out by Rao & P. Williams (*J. Chromatography A*, 693, 633 (1995)) have shown that a cyclohexane diamine derivative (FIG. 3A, where PYR is pyridine) binds to a variety of metal ions. The resulting metal chelator has been successfully used to resolve amino acids and peptides, showing that the molecule has a very high affinity for α-amino acids, forming a very stable coordination complex, which is unique in many respects.

Figure 3C:
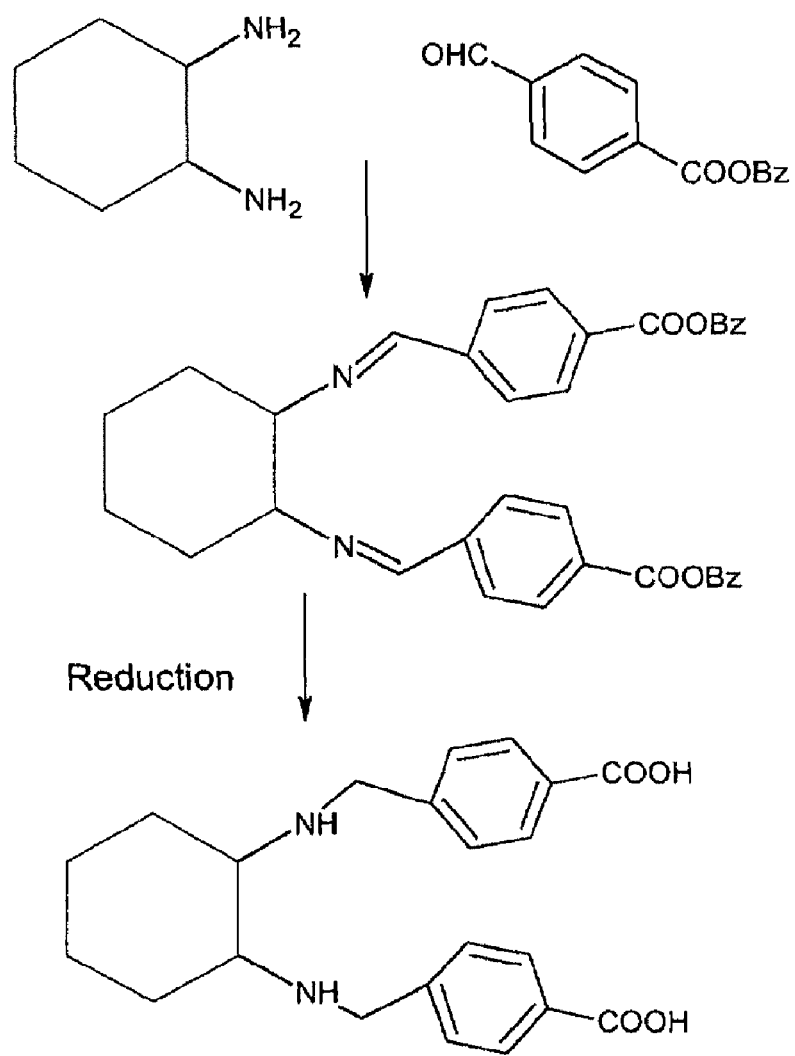
FIGS. 3C-D: Schematic diagrams of syntheses of cyclohexane diamine derivatives of the tetrapeptide Asp Ala His Lys [SEQ ID NO:1].

1,2-Diaminocyclohexane possesses a reactive amino functional group to which a peptide of the invention can be attached. See FIG. 3B, where M is a metal ion and at least one $R_4$ is -alkyl-CO-peptide, -aryl-CO-peptide, -aryl-alkyl-CO-peptide, or -alkyl-aryl-CO-peptide (see also FIGS. 3C-D). The other $R_4$ may be the same or may be -alkyl-COOH, -aryl-COOH, -aryl-alkyl-COOH, or alkyl-aryl-COOH. Derivatives of the type shown in FIG. 3B will have several metal-binding sites and can, therefore, be expected to bind metal ions more readily than the unsubstituted peptide. Further, due to the presence of the cyclohexane functionality, the compound will possess lipid-like characteristic which will aid its transport across lipid membranes.

Figure 3D:
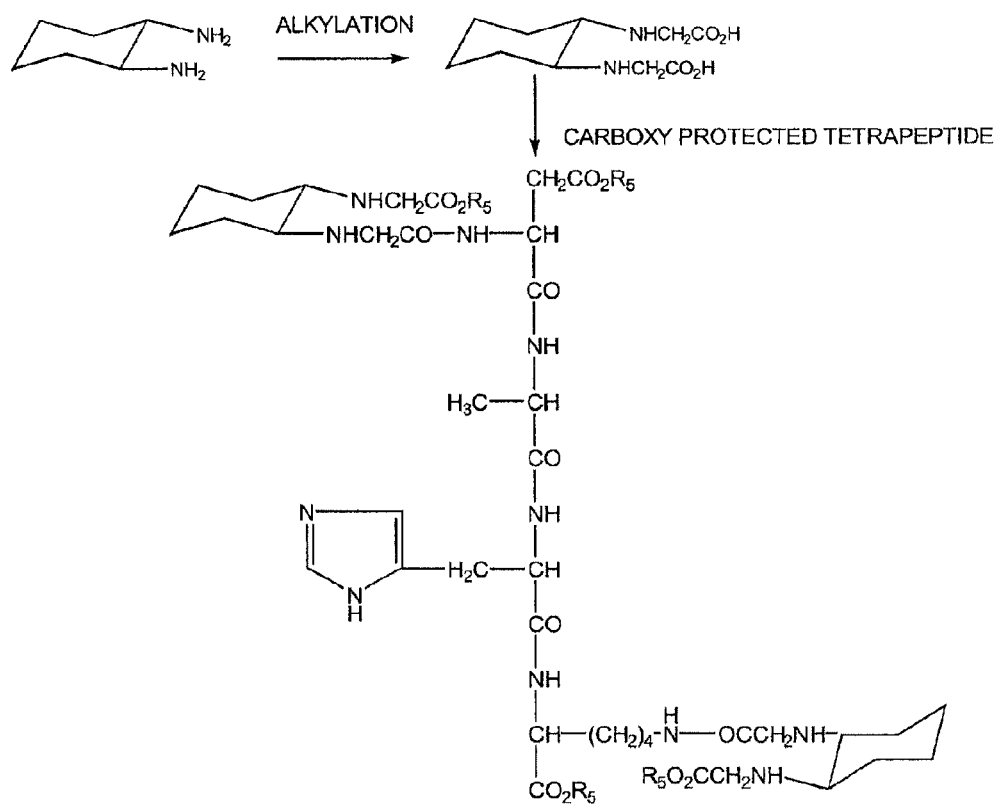

Cyclohexane diamine derivatives of the peptides of the invention can be prepared by two distinct routes. The first involves initial condensation with an aldehyde followed by reduction (see FIG. 3C; in FIG. 3C Bz is benzyl). A number of aldehydes (alkyl and aryl) react readily with cyclohexane diamine at room temperature, forming an oxime. The oxime can be reduced with sodium borohydride under anaerobic conditions to give the diacid derivative. The carboxyl moieties are then reacted with the free amino groups present in carboxy-protected $P_1$ to give the cyclohexane diamine derivative of the peptide. The second route is a direct alkylation process which is illustrated in FIG. 3D. For example, cyclohexane diamine is treated with bromoacetic acid to give the diacetic acid derivative. The carboxyl moieties are then reacted with the free amino groups present in carboxy-protected $P_1$ to give the derivative. In FIG. 3D, $R_5$ is H or another peptide. When $R_5$ is H, the derivative can be further reacted to produce typical carboxylic acid derivatives, such as esters, by methods well known in the art. Metal binding experiments have indicated that the presence or absence of this group does not have a bearing on the metal binding capacity of the whole molecule. However, these groups would either make the molecule hydrophobic or hydrophilic, depending upon the substituent, and this may, in turn, have an effect on delivery of the molecule across membranes or to target tissues. These two synthetic routes will work for the synthesis of diamine peptide derivatives using the other diamines described above.

Additional suitable polyamines and polyamine derivatives and methods of attaching them to peptides are described in U.S. Pat. Nos. 5,101,041 and 5,650,134, the complete disclosures of which are incorporated herein by reference. Other polyamine chelators suitable for attachment to peptides are known. See, e.g., U.S. Pat. Nos. 5,422,096, 5,527,522, 5,628,982, 5,874,573, and 5,906,996 and PCT applications WO 97/44313, WO 97/49409, and WO 99/39706.

It is well known that vicinal diacids bind to metal ions, and the affinity for copper is particularly high. It is therefore envisaged that a peptide having a vicinal diacid functional group will be extremely effective in metal binding. Suitable vicinal diacids include any 1,2-alkyldiacid, such as diacetic acid (succinic acid), and any 1,2-aryldiacid.

Figure 4:
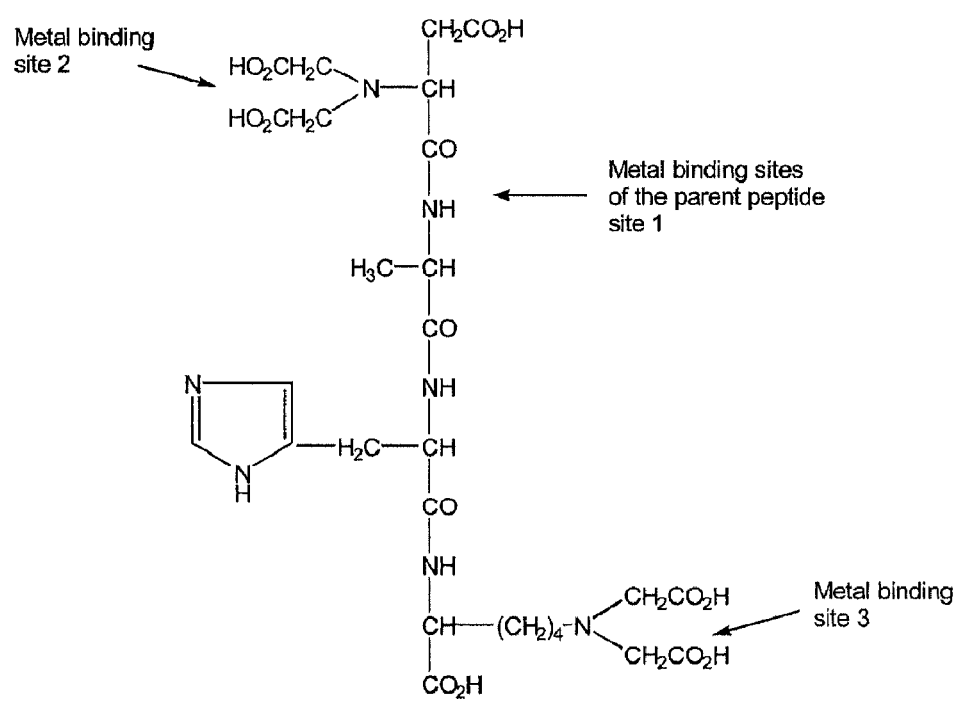
FIG. 4: Formula of a tetraacetic acid derivative of the tetrapeptide Asp Ala His Lys [SEQ ID NO:1].

The amino groups of the peptide can be reacted with diacetic acid to produce a diacid derivative (see FIG. 4). This can be conveniently accomplished by reacting the amino groups of the resin-bound peptide with a halogenated acetic acid (e.g., bromoacetic acid or chloroacetic acid) or a halogenated acetic acid derivative (e.g., benzyloxy ester). Solid phase synthetic procedures enable removal of unreacted materials by washing with solvent. The final product is released from the resin by hydrolytic cleavage. Other diacid derivatives of the peptides of the invention can be made in the same manner.

Polyaminopolycarboxylic acids are known to bind metals, such as copper and iron. Suitable polyaminopolycarboxylic acids for making derivatives of the peptides of the invention and methods of attaching them to peptides are described in U.S. Pat. Nos. 5,807,535 and 5,650,134, and PCT application WO 93/23425, the complete disclosures of which are incorporated herein by reference. See also, U.S. Pat. No. 5,739,395.

Figure 7:
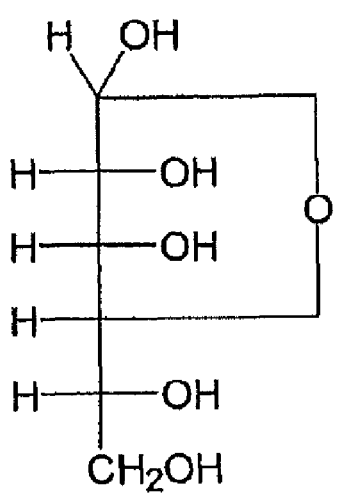
FIG. 7: Formulas of monosaccharides.
Figure 7:
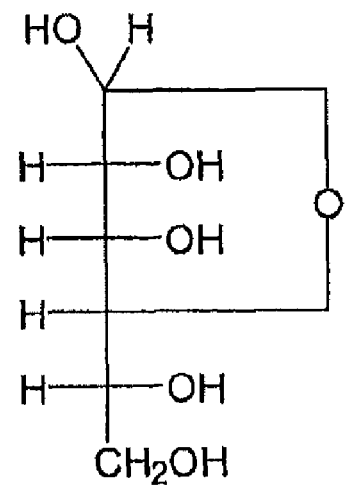
Figure 7:
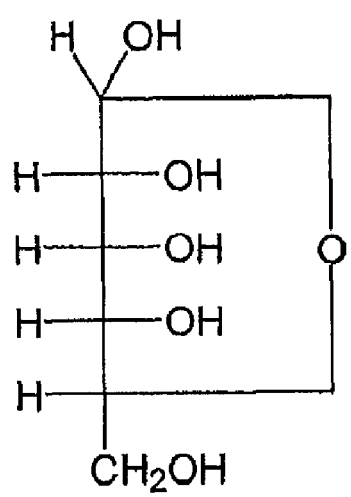
Figure 7:
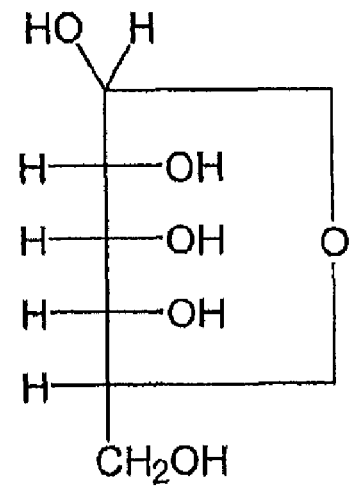

Vicinal polyhydroxyl derivatives are also included in the invention. Suitable vicinal polyhydroxyls include monosaccharides and polysaccharides (i.e., disaccharide, trisaccharide, etc.). Presently preferred are monosaccharides. See FIG. 7. The monosaccharides fall into two major categories—furanoses and pyranoses. One of the prime examples of a furanose ring system is glucose. The hydroxyl groups of glucose can be protected as benzyl or labile t-butyloxy functional groups, while leaving the aldehyde free to react with an amine group (e.g., that of lysine) of the tetrapeptide. Mild reduction/hydrolysis produces the monosaccharide peptide derivative. Other monosaccharide peptide derivatives can be prepared in this manner.

Figure 5:
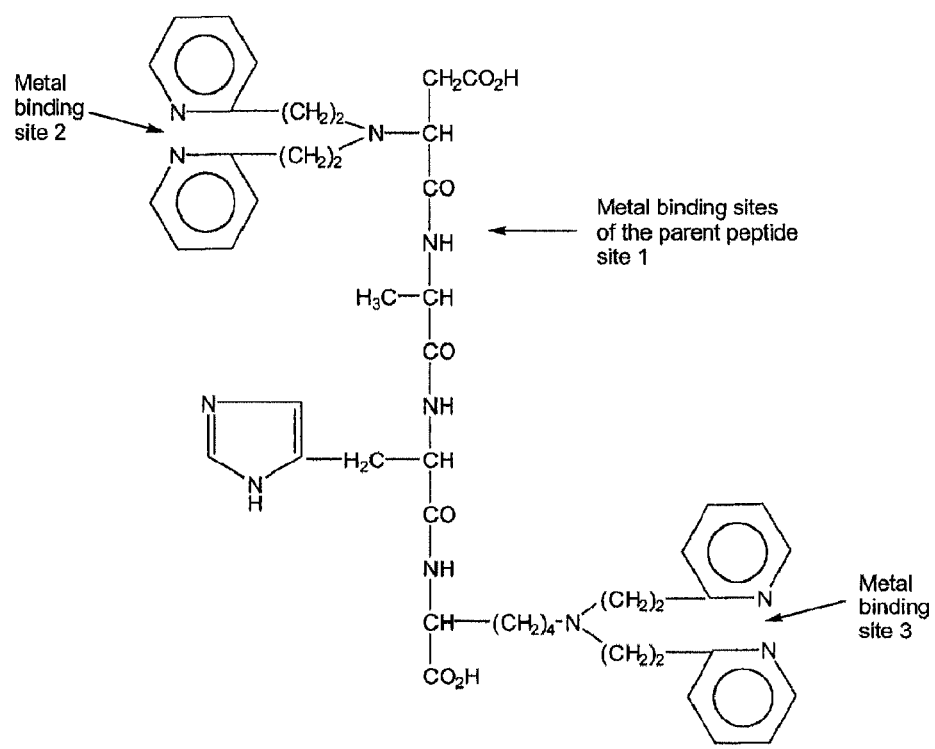
FIG. 5: Formula of a bispyridylethylamine derivative of the tetrapeptide Asp Ala His Lys [SEQ ID NO:1].

Bispyridylethylamine derivatives are known to form strong complexes with divalent metal ions. When attached to the peptide, this functional group would provide additional chelating sites for metal ions, including copper. The bispyridylethyl derivative of the tetrapeptide Asp Ala His Lys [SEQ ID NO:1] is shown in FIG. 5. It is anticipated that the metal-binding capacity of this tetrapeptide derivative will be increased by at least three-fold as compared to the underivatized peptide. The preparation of this bispyridylethylamine derivative shares some similarities with the synthesis of diacid derivatives. The two amino groups of the tetrapeptide (one at Asp and the other at Lys) are reacted with 2-bromoethylpyridine to give the tetra-substituted peptide derivative. The reaction is accomplished by reacting the resin-bound tetrapeptide with the bromoethylpyridine, followed by cleavage of the product from the resin.

Phenanthroline is another heterocyclic compound capable of binding divalent metal ions. Phenanthroline derivatives of the peptides can be synthesized in the same manner as for the bispyridylethylamine derivatives.

Figure 6A:
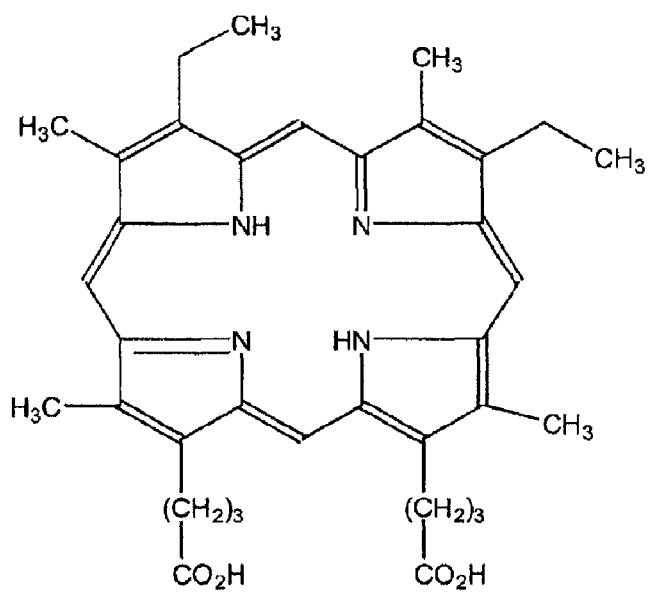
FIGS. 6A-B: Formulas of mesoporphyrin IX with (FIG. 6B) and without (FIG. 6A) a bound metal ion M.
Figure 6B:
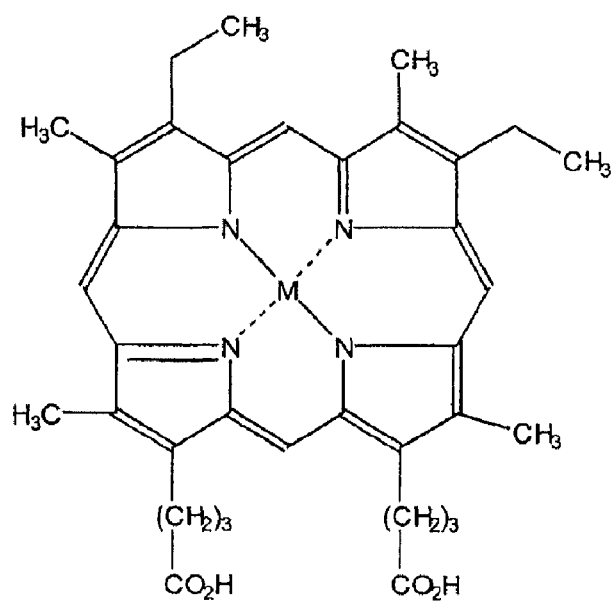

Porphyrins are a group of compounds found in all living matter and contain a tetrapyrrolic macrocycle capable of binding to metals. Heme, chlorophyll and corrins are prime examples of this class of compounds containing iron, magnesium and cobalt, respectively. Mesoporphyrin IX (FIG. 6A-B, where M is a metal ion) is derived from heme and has been observed to possess specific affinity for copper. Addition of this structure to a peptide of the invention would produce a porphyrin-peptide derivative possessing several sites for binding of copper (see FIG. 6C). In addition to their roles in metal binding, the imidazole residues at positions 3 and 3' of the tetrapeptide shown in FIG. 6C may provide a binding site for metals other than copper, thereby stabilizing the porphyrin-metal complex. In particular, cyanocobalamine (vitamin B-12) contains cobalt as the metal in the porphyrin nucleus, and the complex is stabilized by the imidazole groups. On the basis of this analogy it is anticipated that the porphyrin-tetrapeptide derivative would bind cobalt (or other metals) at normal physiological conditions in the prophyrin nucleus and that the complex would be stabilized by the His imidazole groups.

Figure 6C:
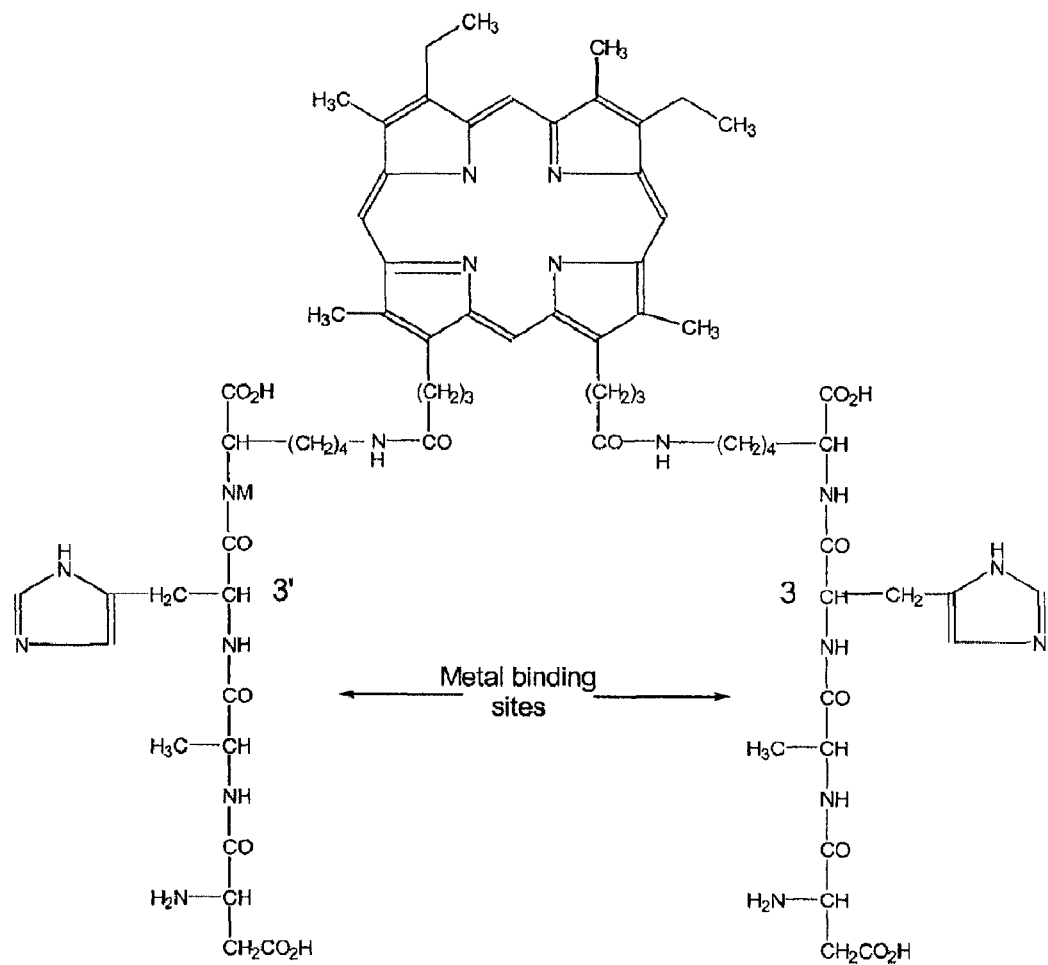
FIG. 6C: Formula of mesoporphyrin IX derivative of the tetrapeptide Asp Ala His Lys [SEQ ID NO:1].

To prepare the porphyrin-peptide derivative shown in FIG. 6C, the carboxyl groups of mesoporphyrin IX can be activated and coupled with the amino groups of the peptide employing standard solid-phase peptide synthesis. Typically, the free amino group of the lysine residue of the resin-bound peptide can be coupled with carboxy activated porphyrin nucleus. The condensation product can be cleaved off the resin using standard methods. This method can be used to synthesize other porphyrin derivatives of peptides of the invention.

Other suitable porphyrins and macrocyclic chelators and methods of attaching them to peptides are described in U.S. Pat. Nos. 5,994,339 and 5,087,696, the complete disclosures of which are incorporated herein by reference. Other porphyrins and macrocyclic chelators that could be attached to peptides are known. See, e.g., U.S. Pat. Nos. 5,422,096, 5,527,522, 5,628,982, 5,637,311, 5,874,573, and 6,004,953, PCT applications WO 97/44313 and WO 99/39706.

A variety of additional metal chelators and methods of attaching them to proteins are described in U.S. Pat. No. 5,683,907, the complete disclosure of which is incorporated herein by reference.

Dithiocarbamates are known to bind metals, including iron. Suitable dithiocarbamates for making derivatives of the peptides of the invention are described in U.S. Pat. Nos. 5,380,747 and 5,922,761, the complete disclosures of which are incorporated herein by reference.

Hydroxypyridones are also known to be iron chelators. Suitable hydroxypyridones for making derivatives of the peptides of the invention are described in U.S. Pat. Nos. 4,912,118 and 5,104,865 and PCT application WO 98/54138, the complete disclosures of which are incorporated herein by reference.

Additional non-peptide metal chelators are known in the art or will be developed. Methods of attaching chemical compounds to proteins and peptides are well known in the art, and attaching non-peptide metal chelators to the peptides of the invention is within the skill in the art. See, e.g., those patents cited above describing such attachment methods.

As can be appreciated, the non-peptide, metal-binding functional groups could be attached to another metal-binding peptide (MBP) in the same manner as they are to peptide $P_1$-$P_2$. The resulting peptide derivatives would contain one or more metal-binding functional groups in addition to the metal-binding site of MBP. Preferably, MBP contains from 2-10, more preferably 3-5, amino acids. Preferably MBP contains one or more D-amino acids; most preferably all of the amino acids of MBP are D-amino acids. As described above, the sequences of many metal-binding peptides are known. These peptides and peptides comprising the metal-binding sites of these peptides can be prepared in the same ways as described above for peptide $P_1$-$P_2$. Derivatives of these peptides having one or more metal-binding functional group attached to the peptide can be prepared in the same ways as described above for derivatives of peptide $P_1$-$P_2$.

The invention also provides metal-binding peptide dimers of the formula:

$P_3$ is any peptide capable of binding a metal ion, and each $P_3$ may be the same or different. Each $P_3$ preferably contains 2-10, more preferably 3-5, amino acids. As described above, metal-binding peptides are known, and each $P_3$ may comprise the sequence of one or more of the metal-binding sites of these peptides. Although each $P_3$ may be substituted as described above for $P_1$ and $P_2$, including with a non-peptide, metal-binding functional group, both $P_3$ peptides are preferably unsubstituted. $P_3$ may also comprise any amino acid sequence substituted with a non-peptide, metal-binding functional group as described above to provide the metal-binding capability of $P_3$. Preferably, each $P_3$ is an unsubstituted metal-binding peptide (i.e., an unsubstituted peptide comprising a peptide sequence which binds metal ions). Most preferably, one or both of the $P_3$ groups is $P_1$ (i.e., the dimers have the sequence $P_3$-L-$P_1$, $P_1$-L-$P_3$ or, most preferably, $P_1$-L-$P_1$). $P_1$ is defined above.

Figure 19A:
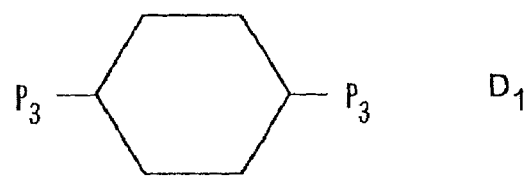
FIG. 19A: Formulas of peptide dimers according to the invention.
Figure 19A:
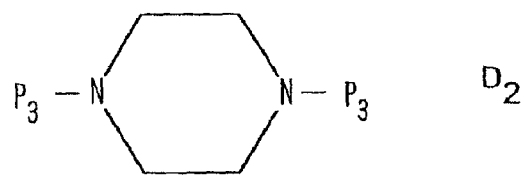
Figure 19A:
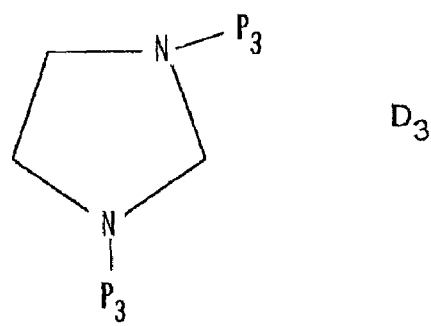
Figure 19A:
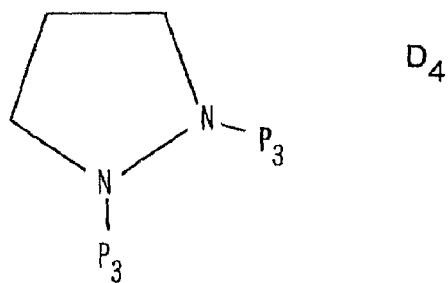
Figure 19A:
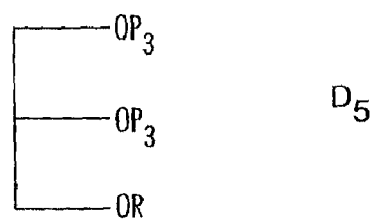

L is a linker which is attached to the C-terminal amino acid of each $P_3$. L may be any physiologically-acceptable chemical group which can connect the two $P_3$ peptides through their C-terminal amino acids. By "physiologically-acceptable" is meant that a peptide dimer containing the linker L is not toxic to an animal (including a human) or an organ to which the peptide dimer is administered as a result of the inclusion of the linker L in the peptide dimer. Preferably, L links the two $P_3$ groups so that they can cooperatively bind metal ions (similar to a 2:1 peptide:metal complex; see Example 10). L is also preferably neutral. Most preferably, L is a straight-chain or branched-chain alkane or alkene residue containing from 1-18, preferably from 2-8, carbon atoms (e.g., —$CH_2$—, —$CH_2CH_2$—, —$CH_2CH_2CH_2$—, —$CH_2CH_2(CH_3)CH_2$—, —CHCH—, etc.) or a cyclic alkane or alkene residue containing from 3-8, preferably from 5-6, carbon atoms (see FIG. 19A, compound $D_1$), preferably attached to a $P_3$ by means of an amide linkage. Such linkers are particularly preferred because they impart hydrophobicity to the peptide dimers. In another preferred embodiment, L is a nitrogen-containing heterocyclic alkane residue (see FIG. 19A, compounds $D_2$, $D_3$ and $D_4$), preferably a piperazide (see FIG. 19A, compound $D_2$). In another preferred embodiment L is a glyceryl ester (see FIG. 19A, compound $D_5$; in formula $D_5$, R is an alkyl or aryl containing, preferably containing 1-6 carbon atoms). Finally, L could be a metal-binding porphyrin (see FIG. 6C). These preferred linkers L will allow the two peptides $P_3$ to bind metal ions cooperatively and are biocompatible, and the peptide dimers containing these preferred linkers can be made easily and in large quantities. By "biocompatible" is meant that a peptide dimer containing the linker L does not produce any undesirable side-effects due to the linker L in an animal (including a human) or an organ to which the peptide dimer is administered.

Figure 19B:
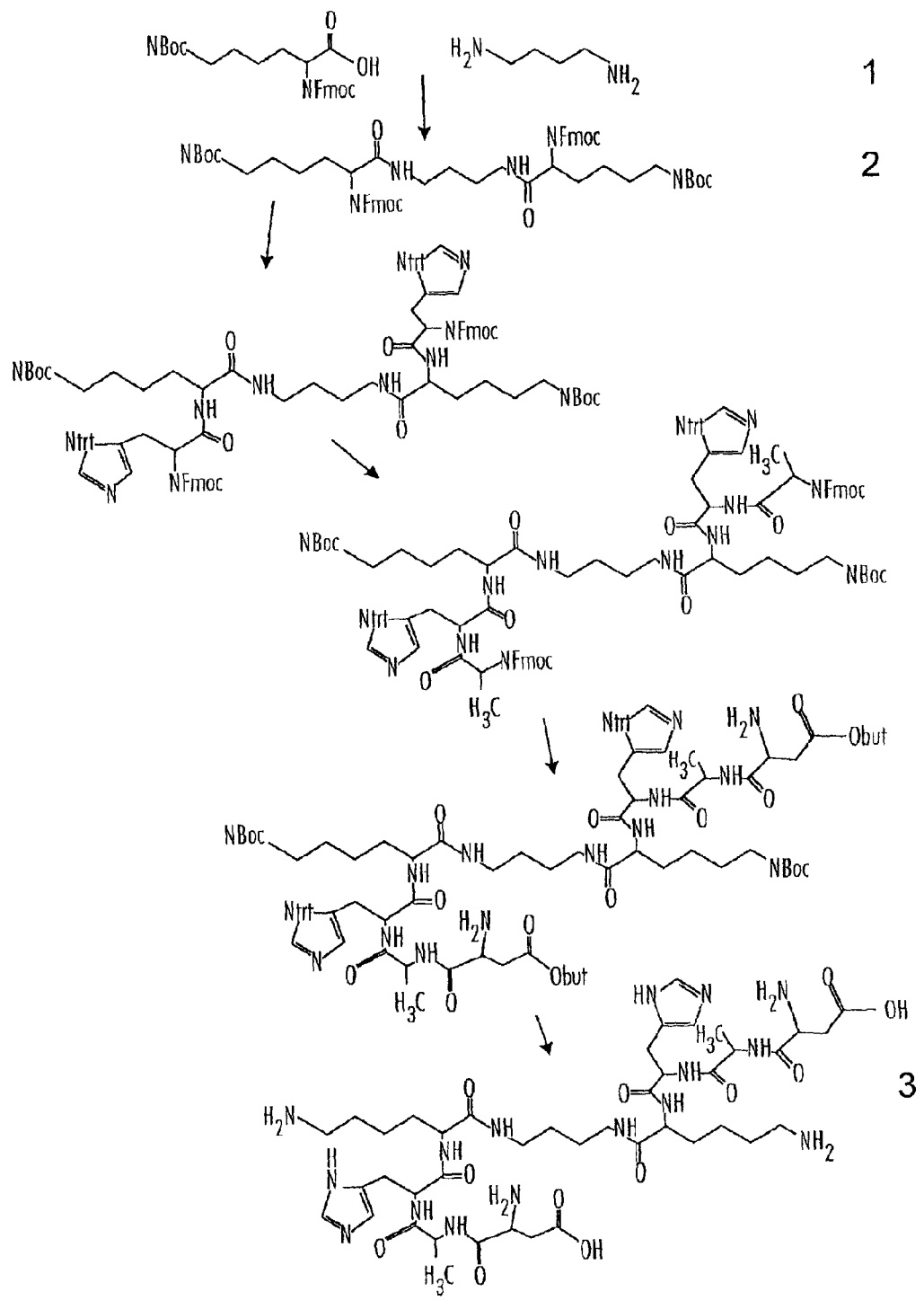
FIGS. 19B-D: Diagrams illustrating the synthesis of peptide dimers according to the invention.
Figure 19C:
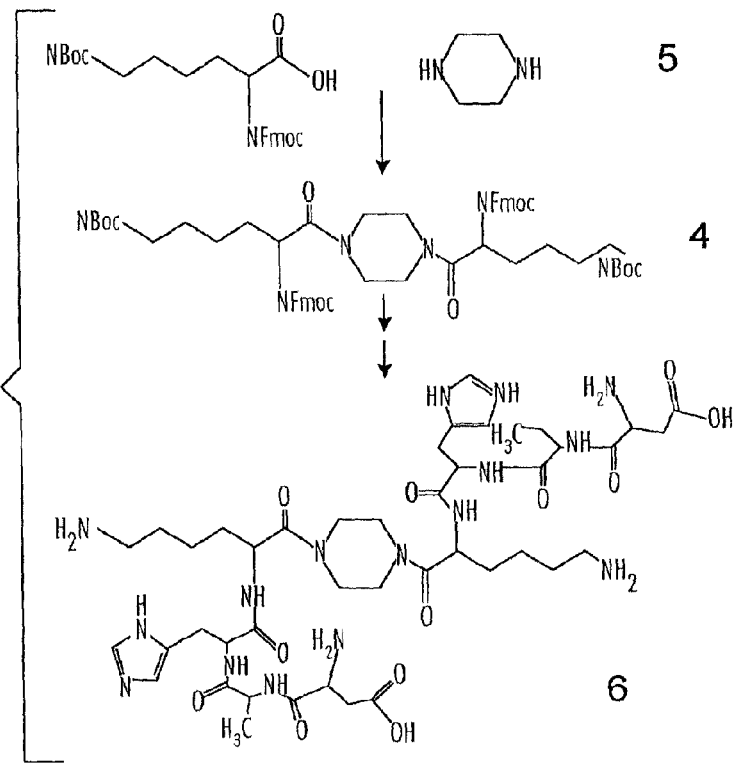
Figure 19D:
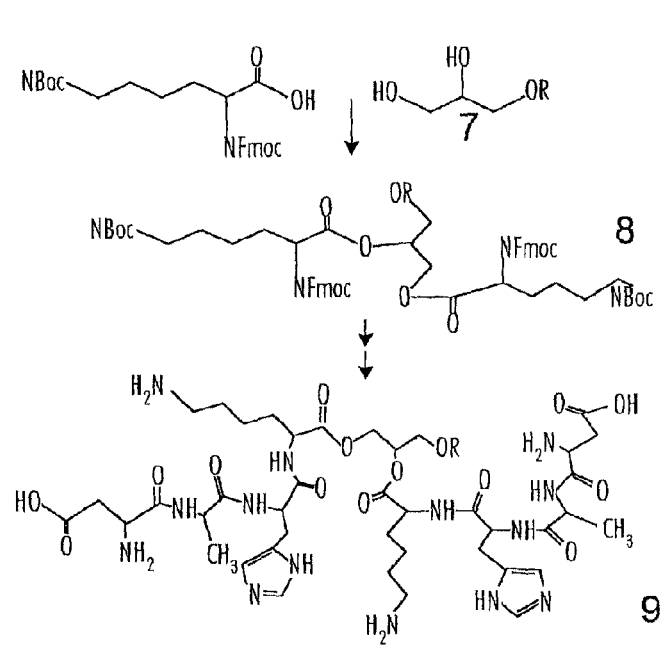

Methods of synthesizing the peptide dimers are illustrated in FIGS. 19B-D. In general, the C-terminal amino acids (protected by methods and protecting groups well known in the art) of the two $P_3$ groups are attached to L, and the resulting amino acid dimers used in standard peptide synthetic methods to make the peptide dimers.

For instance, a peptide dimer, where each peptide has the sequence Asp Ala His Lys, [SEQ ID NO:1] can be synthesized by coupling protected lysines to a free diamine functional group, either as an acid chloride or by using standard coupling agents used in peptide synthesis (see FIGS. 19B-C). Many suitable diamines are available commercially or suitable diamines can be readily synthesized by methods known in the art.

For instance, the lysine dimer 2 (FIG. 19B) can be prepared as follows. To a stirred solution of 9-fluorenylmethyloxycarbonyl (Fmoc)- and t-benzyloxycarbonyl(Boc)-protected D-Lys (Fmoc-D-Lys(Boc)-OH) (20 mmole) in dry dimethylformamide (DMF; 100 mL; dry argon flushed) are added butane-1,4-diamine 1 and 2-(1H-benzotriazole-1-yl)-1,2,3,3-tetramethyluroniumtetrafluoroborate (TBTU; 0.5 mmole). The solution is stirred for 36 hours at room temperature. The bis-protected lysine 2 is isolated by flash chromatography over silica and elution with mixtures of ethyl acetate/methanol. The peptide dimer 3 is then prepared from the protected lysine dimer 2 employing classical peptide synthesis methodology (see FIG. 19B).

Another peptide dimer, where each peptide has the sequence Asp Ala His Lys [SEQ ID NO:1], can be synthesized as follows. First, a different protected lysine dimer 4 is synthesized by acylating the two amino centers of a piperazine 5 (see FIG. 19C; see also Chambrier et al., *Proc. Natl. Acad. Sci.*, 96, 10824-10829 (1999)). Then, the remainder of the amino acid residues are added employing standard peptide synthesis methodology to give the peptide dimer 6 (see FIG. 19C).

Peptide dimers, where each peptide has the sequence Asp Ala His Lys [SEQ ID NO:1] and where L is a glyceryl ester, can be synthesized as follows. The 3-substituted propane-1, 2-diols of formula 7 in FIG. 19D, wherein R is an alkyl or aryl, are commercially available. A lysine diester 8, wherein R is methyl, can be prepared as follows (see FIG. 19D). To a stirred solution of Fmoc-D-Lys(Boc)-OH (20 mmole) in dry toluene (100 mL; dry argon flushed) is added 3-methoxypropane-1,2-diol (200 mmole) and imidazole (15 mmole). The solution is stirred for 36 hours at room temperature. The solvent is removed in vacuo, and the residue is dissolved in ethyl acetate. This solution is washed with citric acid solution (2%), water, 0.5 N $NaHCO_3$ solution, and again with water; then the organic layer is dried over magnesium sulphate (removal of the solvent gives a pale yellow residue). The bis-protected lysine 8 is isolated by flash chromatography over silica and elution with mixtures of ethyl acetate/methanol. The peptide dimer 9 is then prepared from the protected lysine dimer 8 employing classical peptide synthesis methodology (see FIG. 19D).

The physiologically-acceptable salts of the metal-binding compounds are also included in the invention. Physiologically-acceptable salts include conventional non-toxic salts, such as salts derived from inorganic acids (such as hydrochloric, hydrobromic, sulfuric, phosphoric, nitric, and the like), organic acids (such as acetic, propionic, succinic, glycolic, stearic, lactic, malic, tartaric, citric, glutamic, benzoic, salicylic, and the like) or bases (such as the hydroxide, carbonate or bicarbonate of a pharmaceutically-acceptable metal cation). The salts are prepared in a conventional manner, e.g., by neutralizing the free base form of the compound with an acid.

A metal-binding compound of the invention can be used to reduce the damage done by ROS or to reduce the metal ion concentration in an animal in need thereof. To do so, a metal-binding compound of the invention is administered to the animal. Preferably, the animal is a mammal, such as a rabbit, goat, dog, cat, horse or human. Effective dosage forms, modes of administration and dosage amounts for the various compounds of the invention may be determined empirically, and making such determinations is within the skill of the art. It has been found that an effective dosage is from about 2 to about 200 mg/kg, preferably from about 10 to about 40 mg/kg, most preferably about 20 mg/kg. However, it is understood by those skilled in the art that the dosage amount will vary with the particular metal-binding compound employed, the disease or condition to be treated, the severity of the disease or condition, the route(s) of administration, the rate of excretion of the compound, the duration of the treatment, the identify of any other drugs being administered to the animal, the age, size and species of the animal, and like factors known in the medical and veterinary arts. In general, a suitable daily dose of a compound of the present invention will be that amount of the compound which is the lowest dose effective to produce a therapeutic effect. However, the daily dosage will be determined by an attending physician or veterinarian within the scope of sound medical judgment. If desired, the effective daily dose may be administered as two, three, four, five, six or more sub-doses, administered separately at appropriate intervals throughout the day. Administration of the compound should be continued until an acceptable response is achieved.

The compounds of the present invention may be administered to an animal patient for therapy by any suitable route of administration, including orally, nasally, rectally, vaginally, parenterally (e.g., intravenously, intraspinally, intraperitoneally, subcutaneously, or intramuscularly), intracisternally, transdermally, transmucosally, intracranially, intracerebrally, and topically (including buccally and sublingually). The preferred routes of administration are orally, intravenously, and topically.

While it is possible for a metal-binding compound of the present invention to be administered alone, it is preferable to administer the compound as a pharmaceutical formulation (composition). The pharmaceutical compositions of the invention comprise a metal-binding compound or compounds of the invention as an active ingredient in admixture with one or more pharmaceutically-acceptable carriers and, optionally, with one or more other compounds, drugs or other materials. Each carrier must be "acceptable" in the sense of being compatible with the other ingredients of the formulation and not injurious to the animal. Pharmaceutically-acceptable carriers are well known in the art. Regardless of the route of administration selected, the compounds of the present invention are formulated into pharmaceutically-acceptable dosage forms by conventional methods known to those of skill in the art. See, e.g., *Remington's Pharmaceutical Sciences*.

Formulations of the invention suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of a compound or compounds of the present invention as an active ingredient. A compound or compounds of the present invention may also be administered as bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monosterate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may be employed as fillers in soft and hard-filled gelatin capsules using such excipients as lactose or milk sugars, as well as high molecular weight polyethylene glycols and the like.

A tablet may be made by compression or molding optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient only, or preferentially, in a certain portion of the gastrointestinal tract, optionally, in a delayed manner. Examples of embedding compositions which can be used include polymeric substances and waxes. The active ingredient can also be in microencapsulated form.

Liquid dosage forms for oral administration of the compounds of the invention include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compound(s), may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or salicylate, and which is solid at room temperature, but liquid at body temperature and, therefore, will melt in the rectum or vaginal cavity and release the active compound. Formulations of the present invention which are suitable for vaginal administration also include pessaries, tampons, creams, gels, pastes, foams or spray formulations containing such carriers as are known in the art to be appropriate.

Dosage forms for the topical, transdermal or transmucosal administration of a compound of this invention include powders, sprays, ointments, pastes, creams, lotions, gels, solutions, patches, drops and inhalants. The active compound(s) may be mixed under sterile conditions with a pharmaceutically-acceptable carrier, and with any buffers, or propellants which may be required.

The ointments, pastes, creams and gels may contain, in addition to a compound or compound(s) of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound or compounds of this invention, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane.

The active ingredient (i.e., a metal-binding compound or compounds of the invention) may also be delivered through the skin using conventional transdermal drug delivery systems, i.e., transdermal patches, wherein the active ingredient is typically contained within a laminated structure that serves as a drug delivery device to be affixed to the skin. In such a structure, the active ingredient is typically contained in a layer, or "reservoir," underlying an upper backing layer. The laminated device may contain a single reservoir, or it may contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form.

The backing layer in these laminates, which serves as the upper surface of the device, functions as the primary structural element of the laminated structure and provides the device with much of its flexibility. The material selected for the backing material should be selected so that it is substantially impermeable to the active ingredient and any other materials that are present. The backing layer may be either occlusive or nonocclusive, depending on whether it is desired that the skin become hydrated during drug delivery. The backing is preferably made of a sheet or film of a preferably flexible elastomeric material. Examples of polymers that are suitable for the backing layer include polyethylene, polypropylene, polyesters, and the like.

During storage and prior to use, the laminated structure includes a release liner. Immediately prior to use, this layer is removed from the device to expose the basal surface thereof, either the drug reservoir or a separate contact adhesive layer, so that the system may be affixed to the skin. The release liner should be made from a drug/vehicle impermeable material.

Transdermal drug delivery devices may be fabricated using conventional techniques, known in the art, for example by casting a fluid admixture of adhesive, active ingredient and vehicle onto the backing layer, followed by lamination of the release liner. Similarly, the adhesive mixture may be cast onto the release liner, followed by lamination of the backing layer. Alternatively, the drug reservoir may be prepared in the absence of active ingredient or excipient, and then loaded by "soaking" in a drug/vehicle mixture.

The laminated transdermal drug delivery systems may, in addition, contain a skin permeation enhancer. That is, because the inherent permeability of the skin to some active ingredients may be too low to allow therapeutic levels of the drug to pass through a reasonably sized area of unbroken skin, it is necessary to coadminister a skin permeation enhancer with such drugs. Suitable enhancers are well known in the art.

The pharmaceutical compositions of the invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, propellants such as fluorocarbons or nitrogen, and/or other conventional solubilizing or dispersing agents.

Preferred formulations for topical drug delivery are ointments and creams. Ointments are semisolid preparations which are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Formulations for buccal administration include tablets, lozenges, gels and the like. Alternatively, buccal administration can be effected using a transmucosal delivery system as known to those skilled in the art.

Pharmaceutical compositions of this invention suitable for parenteral administrations comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form.

Alternatively, delayed absorption of a parenterally-administered drug is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

As noted above, ROS have been reported to play a major role in a variety of diseases and conditions. See Manso, *Rev. Port. Cardiol.*, 11, 997-999 (1992); Florence, *Aust. N Z J. Opthalmol.*, 23, 3-7 (1992); Stohs, *J. Basic Clin. Physiol. Pharmacol.*, 6, 205-228 (1995); Knight, *Ann. Clin. Lab. Sci.*, 25, 111-121 (1995); Kerr et al., *Heart & Lung*, 25, 200-209 (1996). Diseases and conditions involving or caused by excess metal ions, and diseases and conditions wherein a reduction in the concentration of metal ions would be desirable, are also known. The metal-binding compounds of the invention can be used to treat any of these diseases and conditions and other diseases and conditions in which ROS or metal ions play a role by administering a metal-binding compound of the invention as described above. "Treat" and variations thereof are used herein to mean to cure, prevent, ameliorate, alleviate, inhibit, or reduce the severity of a disease or condition or of at least some of the symptoms or effects thereof.

Specific diseases and conditions that are treatable with the metal-binding compounds of the invention include adult respiratory distress syndrome, aging, AIDS, angiogenic diseases, artherosclerosis (hypertension, senility and impotence), arthritis, asthma, autoimmune diseases, cancer (e.g., kidney, liver, colon, breast, gastrointestinal and brain), carcinogenesis, cellular damage caused by ionizing radiation (e.g., radiation of tumors), chronic granulomatous disease, cirrhosis, colitis, Crohn's disease, cystic fibrosis, degenerative diseases of aging, diabetes (diabetic retinopathy, renal disease, impotence and peripheral vascular disease), eye diseases (e.g., cataracts, central artery occlusion, benign monoclonal gammopathy, and macular degeneration), emphysema, head injury and traumatic brain injury, hepatitis C, infertility (copper present in seminal fluid can damage or kill sperm and/or lower sperm motility), inflammation, inflammatory bowel disease, metastasis, ischemia, neoplastic diseases, neurological diseases, neurological trauma, neurodegenerative diseases (e.g., Alzheimer's disease, amyotropic lateral sclerosis, Huntington's chorea, Parkinson's disease, multiple sclerosis, and senile dementia), pancreatitis, peripheral vascular disease, prion disease (transmissible spongiosiform encephalomyopathy), pulmonary embolism, renal disease (dialysis patients), reperfusion, scleroderma, sepsis, shock, tissue damage occurring upon administration of chemotherapeutics, tissue damage after surgery (e.g., transplantation surgery, open heart surgery, and any surgery where the blood supply to a tissue is cut off, and surgical ischemia of the limbs (tourniquet injury)), toxic reactions (e.g, herbicide poisoning, transition metal (copper, cobalt, and nickel) poisoning, carbon monoxide poisoning, and antibiotic toxicity), traumatic crush injury, and Wilson's disease (congenital high levels of copper).

Specific ischemic conditions and diseases treatable with the metal-binding compounds of the invention include:
Central nervous system ischemia—
Brain ischemia after surgery
Hyperthermia brain injury
Perinatal hypoxia-induced ischemia ("cerebral palsy")
Seizures
Spinal cord injury
Stroke (thrombotic, embolic or hemorrhagic cerebrovascular accident)
Transient ischemic attack
Traumatic brain injury
Cardiac ischemia—
Acute myocardial infarction
Angina pectoris
Arrythmias
Cardiac ischemia after surgery
Congestive heart failure
Myocardial "stunning" (low cardiac output syndrome)
Ischemic bowel disease
Placental ischemia and fetal distress
Pulmonary embolism
Surgery where the blood supply to a tissue or organ is cut off—
Angioplasty
Cardiac bypass surgery
Transplantation surgery (both the donor organ and the recipient of the organ)
Surgical ischemia of the limbs (tourniquet injury).

An angiogenic disease or condition is a disease or condition involving, caused by, exacerbated by, or dependent on angiogenesis. Angiogenesis is the process of new blood vessel formation in the body. Copper is required for angiogenesis. See PCT application WO 00/21941 and "The Role Of Copper In The Angiogenesis Process", (Jan. 28, 2002), and references cited in both of them. In particular, copper is involved in the activation of growth factors (such as the dimerization of b-FGF and serum $Cu^{2+}$-GHK), activation of angiogenic factors (such as $Cu^{2+}$-(K)GHK derived from SPARC), cross-linking of the transitional matrix (e.g., collagens VIII and I by $Cu^{2+}$-dependent lysyl oxidase), and formation of basement membrane (e.g., collagens IV and elastin by $Cu^{2+}$-dependent lysyl oxidase).

Specific angiogenic diseases and conditions treatable with the metal-binding compounds of the invention include neoplastic diseases (e.g., tumors (e.g., tumors of the bladder, brain, breast, cervix, colon, rectum, kidney, lung, ovary, pancreas, prostate, stomach and uterus) and tumor metastasis), benign tumors (e.g., hemangiomas, acoustic neuromas, neurofibromas, trachomas, and pyrogenic granulomas), hypertrophy (e.g., cardiac hypertrophy induced by thyroid hormone), connective tissue disorders (e.g., rheumatoid arthritis and atherosclerosis), psoriasis, ocular angiogenic diseases (e.g., diabetic retinopathy, retinopathy of prematurity, macular degeneration, corneal graft rejection, neovascular glaucoma, retrolental fibroplasia, and rubeosis), cardiovascular diseases, cerebral vascular diseases, endometriosis, polyposis, obesity, diabetes-associated diseases, hemophiliac joints, and immune disorders (e.g., chronic inflammation and autoimmunity). The metal-binding compounds of the invention can also be used to inhibit the vascularization required for embryo implantation, thereby providing a method of birth control.

High copper levels have been found in the serum and tumors of patients with many types of progressive tumors. As noted above, copper plays a major role in angiogenesis, thereby contributing to tumor growth and metastasis. Also, metals, particularly copper and nickel, have been reported to be carcinogens. Thus, the metal-binding compounds of the invention may be used to reduce copper levels in cancer patients. The metal-binding compounds of the invention may also be used to inhibit (reduce or prevent) carcinogenesis in individuals at risk (e.g., metal-exposed individuals, such as welders, machinists, autobody repairmen, etc.).

Specific inflammatory diseases and conditions treatable with the metal-binding compounds of the invention include acute respiratory distress syndrome, allergies, arthritis, asthma, autoimmune diseases, bronchitis, cancer, Crohn's disease, cystic fibrosis, emphysema, endocarditis, gastritis, inflammatory bowel disease, ischemia reperfusion, multiple organ dysfunction syndrome, nephritis, pancreatitis, respiratory viral infections, sepsis, shock, ulcerative colitis and other inflammatory disorders.

Acidosis is present in, or plays a role in, a number of diseases and conditions, including hypoventilation, hypoxia, ischemia, prolonged lack of oxygen, severe dehydration, diarrhea, vomiting, starvation, AIDS, sepsis, kidney disease, liver disease, metabolic diseases (e.g., advanced stages of diabetes mellitus), and neurodegenerative diseases (e.g., Alzheimer's). Acidosis is also caused by certain medications (e.g., large amounts of aspirin and oral medications used to treat diabetes), and instances of mild acidosis have been reported to increase with age (Knight, "Metal Heads," New Scientist, Aug. 26, 2000. Under normal conditions, copper is bound to plasma proteins and peptides, primarily ceruloplasmin and albumin. In acidotic conditions, copper is released from the proteins to which it is normally bound. It is estimated that 40-70% of weakly bound copper is released at pH 6.0. Free copper can participate in reactions that lead to the formation of ROS and causes a number of other deleterious effects, such as interfering with metabolism and energy ultilization. Thus, the metal-binding compounds of the invention may be used to treat diseases or conditions involving acidosis to prevent damage due to ROS, to prevent other deleterious effects of free copper, or both.

Sepsis can also be treated using the metal-binding compounds of the invention. Sepsis is a systemic inflammatory response to infection. Sepsis is also characterized by ischemia (caused by coagulopathy and suppressed fibrinolysis) and acidosis.

A compound of the invention is preferably administered prophylactically. For instance, a compound of the invention is preferably administered prior to and/or simultaneously with reperfusion of an ischemic tissue or organ (e.g., prior to and/or simultaneously with angioplasty or treatment with clot dissolving drugs, such as tissue plasminogen activators). Of course administration of a compound of the invention should be continued for a period of time after reperfusion has been achieved. Similarly, a compound of the invention should be administered prior to and/or during surgery (e.g., open-heart surgery or surgery to transplant an organ into an animal), and administration of the compound should be continued for a period of time after the surgery. As another example of prophylactic administration, a compound of the invention can be administered to a patient presenting symptoms of a serious condition (e.g., cerebrovascular ischemia or cardiovascular ischemia) while the patient is tested to diagnose the condition. In this way, the patient will be protected during the time it takes to diagnose such conditions, and treatment with the metal-binding compounds of the invention may also prolong the time during which other therapies (e.g., administration of tissue plasminogen activator for cerebrovascular ischemia) can be administered. As yet a further example, a compound of the invention can be administered at the time a patient is to undergo radiation therapy (e.g., radiation for a tumor or prior to a bone marrow transplant).

A compound of the invention can also be used to treat patients who have suffered blunt trauma. In particular, a compound of the present invention may be very beneficial in treating patients suffering from multiple blunt trauma who have a low albumin level, since it has been found that a low albumin level is a predictor of mortality in such patients. More specifically, 34 patients suffering from multiple blunt trauma were studied. These patients were admitted to the intensive care unit of Swedish Hospital, Denver, Colo. in 1998. Two groups of patients were matched by a trauma surgeon by age, injury severity score (ISS), and type and area of injury without knowledge of the albumin levels of the patients. One group was composed of the patients who died, and the other group was composed of survivors. Following the match, the admission albumin levels were retrieved from the medical records by an independent observer, and the albumin levels of the two groups were compared. For the 17 survivors, the mean albumin level was 3.50±1.00 g/dl. For the 17 patients who died, the mean albumin level was 2.52±0.73 g/dl. The % variance was 28.6 and 28.9, respectively, and the p-value was 0.0026 (95% confidence interval 0.3462-0.4771).

The compounds of the invention may be given alone to reduce the damage done by ROS. Alternatively, the compounds of the invention can be given in combination with "free radical scavengers." "Free radical scavengers" include superoxide dismutase, catalase, glutathione peroxidase, ebselen, glutathione, cysteine, N-acetyl cysteine, penicillamine, allopurinol, oxypurinol, ascorbic acid, α-tocopherol, Trolox (water-soluble α-tocopherol), β-carotene, fatty-acid binding protein, fenozan, probucol, cyanidanol-3, dimercaptopropanol, indapamide, emoxipine, dimethyl sulfoxide, and others. See, e.g., Das et al., *Methods Enzymol.,* 233, 601-610 (1994); Stohs, *J. Basic Clin. Physiol. Pharmacol.,* 6, 205-228 (1995). The compounds of the invention can also be given in combination with another metal-binding peptide or non-peptide chelator (suitable metal-binding peptides and non-peptide chelators are described above and others are known in the art). For instance, a peptide $P_1$ (i.e., peptide $P_1$-$P_2$ wherein n=0 in the formula of $P_2$), which binds Cu(II) tightly, could be given in combination with a separate peptide suitable for binding Cu(I) (suitable Cu(I)-binding peptides are described above). As another example, a peptide $P_1$ could be given in combination with a separate peptide or non-peptide chelator capable of binding iron. Suitable iron-binding peptides and non-peptide chelators are described above and others are known in the art (e.g., deferoxamine mesylate). The compounds of the invention can, of course, also be given along with standard therapies for a given conditions (e.g., insulin to treat diabetes).

The metal-binding compounds of the invention can also be used to reduce the damage done by ROS to a cell, a tissue or organ that has been removed from an animal. To reduce the damage done by ROS to a tissue or an organ, the tissue or organ is contacted with a solution containing an effective amount of a metal-binding compound of the invention. Many suitable solutions are known. See, e.g., Dunphy et al., *Am. J. Physiol.,* 276, H1591-H1598 (1999); Suzer et al., *Pharmacol.*

Res., 37, 97-101 (1998); Hisatomi et al., *Transplantation*, 52, 754-755 (1991); U.S. Pat. No. 5,710,172. Effective amounts of the metal-binding compound to include in such solutions can be determined empirically, and doing so is within the skill in the art. The harvested tissue or organ may subsequently be used for transplantation into a recipient or for research purposes (e.g., using a perfused liver to screen drugs). The metal-binding compounds of the invention can be used alone or can be used in combination with a free radical scavenger or another metal-binding compound (see above).

Cells isolated from an animal can be stored or cultured in a medium containing an effective amount of a metal-binding compound of the invention. Many suitable media are known. Effective amounts of the metal-binding compound to include in the medium can be determined empirically, and doing so is within the skill in the art. The cells may be administered to a recipient in need thereof (e.g., for cellular immunotherapy or gene therapy) or may be used for research purposes.

In addition, media containing an effective amount of a metal-binding compound of the invention can be used in in vitro fertilization (IVF) procedures for reducing the damage done by ROS to gametes (sperm and/or ova), zygotes, and blastocysts during collection, storage and/or culture. In particular, seminal fluid is known to contain substantial amounts of copper and fructose, conditions suitable for the production of ROS. Many suitable media for use in IVF procedures are known (e.g., Gardner media G1, G2, etc.). Effective amounts of the metal-binding compound to include in the media can be determined empirically, and doing so is within the skill in the art.

The invention further provides a kit for reducing the damage done by ROS to a cell, a tissue or organ that has been removed from an animal. The kit is a packaged combination of one or more containers holding reagents and other items useful for preserving harvested cells, tissues or organs. The kit comprises a container holding a metal-binding compound of the invention. Suitable containers include bottles, bags, vials, test tubes, syringes, and other containers known in the art The kit may also contain other items which are known in the art and which may be desirable from a commercial and user standpoint, such as a container for the cells, tissue or organ, diluents, buffers, empty syringes, tubing, gauze pads, disinfectant solution, etc.

It is to be noted that "a" or "an" entity refers to one or more of that entity. For example, "a cell" refers to one or more cells.

EXAMPLES

Example 1

Synthesis of Tetrapeptide Asp Ala His Lys [SEQ ID NO:1]

This example describes the synthesis of the tetrapeptide Asp Ala His Lys [SEQ ID NO:1] composed of all L-amino acids using standard solid-phase synthesis techniques. First, 9-fluorenylmethyloxycarbonyl (Fmoc)-protected Asp (v COO— ester; Tolsulfonyl) on Wang resin (0.6 mmole; Nova Biochem) was suspended in a solution of piperidine/dimethylformamide (DMF) (40% v/v; 3 ml) for 30 min with occasional agitation. At the end of this period, the solvent was drained, and the resin was washed sequentially with DMF and dichloromethane (DCM; 5×3 ml). A ninhydrin test was used to monitor the reaction. The resin was swollen with DMF (~1 ml). The C-protected t-benzyloxycarbonyl (Boc) ester of alanine in DMF was added, followed by a mixture of diisopropylamine (8 equivalent) and 2-(1H-benzotriazole-1-yl)-1,2, 3,3-tetramethyluroniumtetrafluoroborate (TBTU-) (4 equivalents). The resin was shaken for about 24 hours, and the reaction was monitored by the ninhydrin test. At the end of this period, DMF was drained, and the resin was washed with DMF and DCM. The solution was drained, and the beads were washed with DCM (3×2 ml). The protecting group of the dipeptide-resin was removed, and the beads were suspended in DMF. Amino protected (benzyloxy) derivative of histidine (4 mmole) was added, followed by mixture of diisopropylamine (8 equivalent) and TBTU-(4 equivalent). The resin was shaken for about 24 hours, and the reaction monitored by ninhydrin test. At the end of this period, DMF was drained, and the resin was washed with DMF and DCM. The tripeptide-resin was briefly dried in a gentle stream of nitrogen and suspended in nitrogen-saturated DMF. Protected lysine was added, followed by a mixture of diisopropylamine (8 equivalent) and TBTU-(4 equivalent). The resin was shaken for about 24 hours, and the reaction monitored by the ninhydrin test. At the end of this period, DMF was drained and the resin was washed with DMF and DCM. The Boc protecting group was carefully removed to give the tetrapeptide bound to the resin, with a typical loading of 5 mmole/g. The resin bound tetrapeptide (0.25 gm; 5 mmolar) was treated with trifluoroacetic acid (TFA) and was shaken for 24 hours. At the end of this period, the ninhydrin test gave a blue color, indicating the release of the tetrapeptide from the resin. In some circumstances, addition of 5% (V/V) of DMF to TFA accelerated the rate of release of the peptide from the resin. Removal of TFA at reduced pressure gave the tetrapeptide (all D) as TFA salt and was dried under vacuum at 5° C. for 24 hours. The residue was a white powder and was characterized by spectrometric methods.

A number of enantiomers of the tetrapeptide can be prepared in this manner. For example, use of D-amino acids in the peptide synthesis forms the tetrapeptide containing all D-amino acids. Also, combinations of L-amino acids and D-amino acids can be used.

Example 2

Preparation of Cyclohexanediamine

Derivative of Asp Ala His Lys [SEQ ID NO:1]

Trans-diaminocyclohexane was prepared by resolving cis/trans 1,2-diaminocyclohexane (Aldrich-Sigma) as the tartaric acid salt. The R-trans isomer melts at 75° C. and the S-trans isomer melts between 43-45° C. (Ph.D. Thesis, P. D. Newman, University College, Cardiff, U.K., 1994). The trans-diaminocyclohexane (10 gm) was then suspended in anhydrous toluene (30 mL) and cooled to 5° C. in an ice bath, and bromoacetic acid (8 gm) in toluene (25 mL) was added dropwise. At the end of the addition, the reaction temperature was raised to 30° C. and kept at that temperature for a further 5 hours. Toluene was evaporated, and the R-trans 1,2-diaminocyclohexane diacetic acid was crystallized from hexane/toluene to give a white solid (yield 70%). The product was characterized by spectroscopic methods.

The resin-bound tetrapeptide prepared in Example 1 (20 mg) was suspended in DMF (5 mL) and was treated with the R-trans 1,2-diaminocyclohexanediacetic acid (20 mg) followed by addition of a mixture of diisopropylamine (8 equivalent) and TBTU-(4 equivalent). The resin was shaken for about 24 h on a roller. Then, the resin was washed with DMF followed by DCM (5×3 mL) and partially dried. Hydrolysis of the resin linkage was effected by treating the resin-bound reaction product with TFA (5 mL; 5 hr). The resin was separated and washed with DCM. The washings were combined with TFA and concentrated under vacuum. The residue (cyclohexanediamine tetrapeptide; formula given in FIG. 3D where $R_5$ is H) was characterized by spectrometric analysis.

Example 3

Preparation of Tetrapeptide Tetracetic Acid

The resin-bound tetrapeptide prepared in Example 1 (20 mg) was suspended in DMF (5 mL) and treated with excess (10-fold) chloroacetic acid. The resin was shaken at room temperature for 48 hours, followed by heating to 60° C. for a further hour. DMF was removed by filtration, and the resin was washed with DMF followed by DCM (5×3 mL). Partially dried resin was used without further treatment in the next stage. Hydrolysis of the resin linkage was effected by treating the resin-bound reaction product with TFA (5 mL; 5 hr). The resin was separated and washed with DCM. The washings were combined with TFA and concentrated under vacuum (yield 30%). The product (formula given in FIG. 4) was characterized by spectrometric methods.

Example 4

Preparation of Mesoporphyrin IX Tetrapeptide

The resin-bound tetrapeptide prepared in Example 1 (20 mg) was suspended in DMF (5 mL) and treated with mesoporphyrin IX dicarboxylic acid (10 μmole; formula given in FIG. 6A), followed by addition of a mixture of diisopropylamine (8 equivalent) and TBTU-(4 equivalent). The resin was shaken for about 24 hours on a roller kept in a dark chamber. The resin was washed with DMF followed by DCM (5×3 mL) and partially dried. Hydrolysis of the resin linkage was effected by treating the resin-bound reaction product with TFA (5 mL; 5 hr). The resin was separated and washed with DCM/TFA mixture (1:1.5 mL). The washings were combined and concentrated under vacuum. The porphyrin tetrapeptide (formula given in FIG. 6C) was purified by semi-preparative HPLC (yield 60%). The structure was confirmed by spectrometric methods.

This procedure can be used to synthesize other porphyrin-peptides, such as mesoporphyrin I and related molecules.

Example 5

Preparation of Tetrabispiridylethyl Tetrapeptide

The resin-bound tetrapeptide prepared in Example 1 (20 mg) was suspended in DMF (5 mL) and treated with bromoethylpyridine (20 μmole). This was followed by the addition of pyridine (0.5 mL). The resin was shaken for about 48 hours on a roller. The resin was washed with DMF, followed by DCM (5×3 mL) to remove all of the unreacted monomers, and then dried under vacuum for 30 minutes. Hydrolysis of the resin linkage was effected by treating the resin-bound reaction product with TFA (5 mL; 5 hr). The resin was separated and washed with DCM/TFA mixture (1:1.5 mL). The washings were combined and concentrated under vacuum. The pyridylethyl tetrapeptide derivative (formula given in FIG. 5) was purified by semi-preparative HPLC (yield 50%). The structure was confirmed by spectrometric methods.

This procedure can be applied to other heterocycles, such as phenanthroline and related molecules.

Example 6

Preparation of Aryl Derivative of Asp Ala His Lys [SEQ ID NO:1]

A derivative having the formula shown in FIG. 1B, wherein $R_1$ is phenyl, was prepared. Diethylacetamidomalonate (10 gm) in anhydrous ethanol (100 mL) was added to a slurry of sodium ethoxide in ethanol (5 gm; 50 mL) and heated to reflux for 30 min. The product was cooled (10° C.) and reacted with ethyl α-bromophenyl acetate (5 gm). The reaction was allowed to proceed to completion (24 h), and excess sodium ethoxide was neutralized with dilute acid. The triester was extracted into ethylacetate and, upon removal of solvent, gave a viscous liquid. The crude product was hydrolyzed with hydrochloric acid (100 mL) and decarboxylated to give phenyl substituted aspartic acid (10 gm). The N-benzoyloxy t-butyl derivative was prepared using a standard reaction sequence. To the resin-bound tripeptide (Lys His Ala) prepared as described in Example 1 (20 mg) in DMF was added the N-benzoyloxy-t-butyl aspartic acid derivative, followed by a mixture of diisopropylamine (8 equivalent) and TBTU-(4 equivalent). The resin was shaken for about 24 h, and the reaction monitored by the ninhydrin test. At the end of this period, DMF was drained, and the resin was washed with DMF and DCM. The solution was drained, and the beads washed with DCM (3×2 ml). The tetrapeptide derivative was isolated by careful hydrolysis. Stereoisomers of the tetrapeptide were separated by preparative-scale HPLC.

Example 7

Inhibition of the Generation of ROS

By The Tetrapeptide Asp Ala His Lys [SEQ ID NO:1]

A tetrapeptide having the sequence L-Asp L-Ala L-His L-Lys [SEQ ID NO:1] (the L-tetrapeptide) was obtained from one or more companies that provide custom synthesis of peptides, including Ansynth Services, QCB, Genosys and Bowman Research. The peptide was prepared by standard solid phase synthesis methods (see also Example 1).

The ability of the L-tetrapeptide to inhibit the generation of ROS was tested as described in Gutteridge and Wilkins, *Biochim. Biophys. Acta,* 759, 38-41 (1983) and Cheeseman et al., *Biochem. J.,* 252, 649-653 (1988). Briefly, Cu(II) and $H_2O_2$ were mixed causing the generation of hydroxyl radicals in a Fenton-type reaction. The hydroxyl radicals attack the sugar 2-deoxy-D-ribose (the sugar residue of DNA) to produce fragments. Heating the fragments at low pH produces malonaldehyde that, upon the addition of 2-thiobarbituric acid, yields a pink chromogen which can be measured spectrophotometrically at 532 nm. Thus, the absorbance at 532 nm is a measure of the damage to 2-deoxy-D-ribose.

The assay was performed with and without the L-tetrapeptide. The results are summarized in Table 1. As can be seen from Table 1, when the L-tetrapeptide was present at Cu(II): tetrapeptide ratios of 1:1.2 and 1:2, the degradation of 2-deoxy-D-ribose was inhibited by 38% and 73%, respectively. Clearly, the L-tetrapeptide inhibited the degradation of 2-deoxy-D-ribose by hydroxyl radicals.

TABLE 1

| | CuCl$_2$ (mM) | H$_2$O$_2$ (mM) | Tetra-peptide (mM) | OD at 532 nm | Percent Inhibition |
|---|---|---|---|---|---|
| Control | 0.1 | 2.0 | 0.0 | 0.124 | |
| Tetrapeptide | 0.1 | 2.0 | 0.12 | 0.077 | 38 |
| Control | 0.1 | 2.0 | 0.0 | 0.175 | |
| Tetrapeptide | 0.1 | 2.0 | 0.2 | 0.048 | 73 |

A similar assay was also performed using a tetrapeptide having the sequence Asp Ala His Lys composed of all D-amino acids (D-tetrapeptide). The D-tetrapeptide was obtained from one or more companies that provide custom synthesis of peptides, including Ansynth Services and QCB. The peptide was prepared by standard solid phase synthesis methods (see Example 1)

The ability of the D-tetrapeptide to inhibit the generation of ROS was tested as described by Zhao and Jung, *Free Radic Res,* 23(3), 229-43 (1995). Briefly, Cu(II) and ascorbic acid were mixed causing the generation of hydroxyl radicals in a Fenton-type reaction. The advantage of using ascorbic acid instead of hydrogen peroxide is that ascorbic acid does not interfere with other assays (i.e. LDH assay) which is not the case with peroxide. The hydroxyl radicals attack the sugar 2-deoxy-D-ribose to produce fragments. Heating the fragments at low pH produces malonaldehyde that, upon the addition of 2-thiobarbituric acid, yields a pink chromogen which can be measured spectrophotometrically at 532 nm. Thus, the absorbance at 532 nm is a measure of the damage to 2-deoxy-D-ribose.

Establishing optimal Cu(II) and ascorbic acid concentrations was the first step in developing this protocol. First, a constant Cup concentration of 10 μM was used based on this level being the physiological concentration found in the body (bound and unbound Cu(II)). The ascorbic acid concentrations were varied in order to establish a linear range. The ascorbic acid concentration chosen was 500 μM since it gave the most absorbance at 532 nm and still fell in the linear range. Interestingly, at ascorbic acid concentrations greater than 500 μM, there was a steady decrease in hydroxyl radicals presumably due to ascorbic acid's dual effect as a hydroxyl radical generator at low concentrations and an antioxidant at high concentrations.

Using the aforementioned concentrations for Cu(II) and ascorbic acid, a titration curve was established for the D-tetrapeptide. Briefly, the D-tetrapeptide was pre-incubated with Cu(II) for 15 minutes at room temperature prior to adding ascorbic acid. This was done to permit the D-tetrapeptide to bind with the Cu(II) and therefore inhibit ROS generation. As can be seen from the table, when the Cu(II):D-tetrapeptide ratio was between 4:1 to 4:7, there was little to no inhibition of hydroxyl radical generation. When the ratio was 1:2 or higher, there was total inhibition of hydroxyl radical production.

TABLE 2

| Cu(II):D-Tetrapeptide | Cu(II) (μM) | Ascorbic Acid (μM) | D-Tetrapeptide (μM) | A532 | % Inhibition |
|---|---|---|---|---|---|
| 1:0 | 10 | 500 | 0 | 0.767 | |
| 4:1 | 10 | 500 | 2.5 | 0.751 | |
| 2:1 | 10 | 500 | 5 | 0.743 | |
| 1:1 | 10 | 500 | 10 | 0.751 | |
| 4:5 | 10 | 500 | 12.5 | 0.789 | |
| 2:3 | 10 | 500 | 15 | 0.774 | |
| 4:7 | 10 | 500 | 17.5 | 0.737 | |
| 1:2 | 10 | 500 | 20 | 0.029 | 96.2 |
| 1:4 | 10 | 500 | 40 | 0.016 | 97.9 |

Example 8

Testing of Asp Ala His Lys D-Tetrapeptide

In A Langendorff Reperfusion Model

Figure 8:
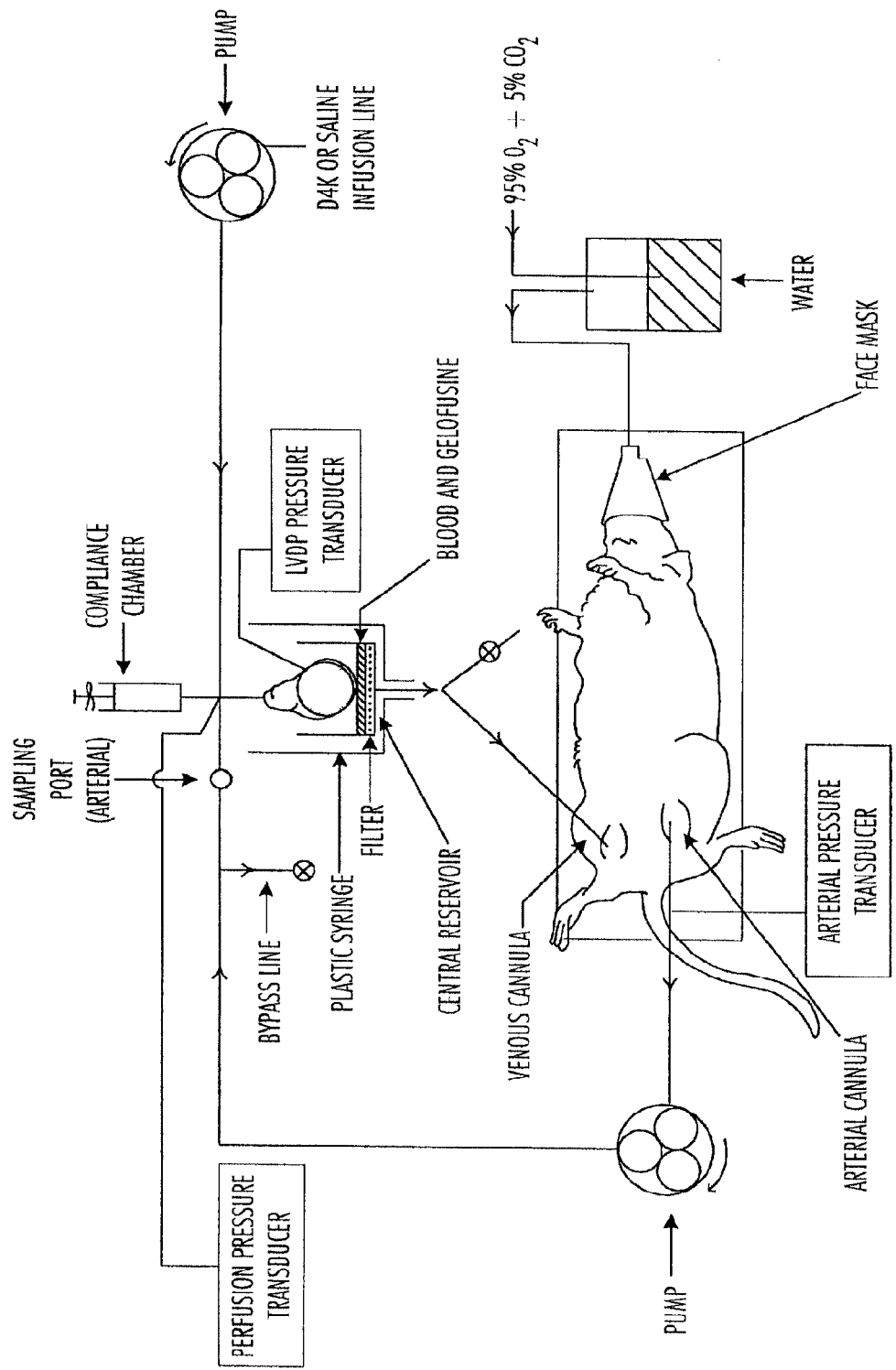
FIG. 8: Diagram of a parabiotic blood perfusion system in which an isolated heart is perfused in the Langendorff mode with blood at 37° C. from a support animal of the same species.

Blood-perfused hearts were prepared essentially as in previous studies (Galiñanes et al., *Circulation,* 88:673-683 (1993); Kolocassides et al., *Am. J. Physiol.,* 269:H1415-H1420 (1995); Hearse et al., *J. Mol. Cell. Cardiol.,* 31:1961-1973 (1999)). See FIG. 8. The procedures are described briefly below.

Male Wistar rats, obtained from Bantin and Kingman Universal, UK, were used. All animals received humane care in compliance with the "*Principles of Laboratory Animal Care*" formulated by the National Society for Medical Research and the "*Guide for the Care and Use of Laboratory Animals*" prepared by the National Academy of Sciences, and published by the US National Institutes of Health (NIH Publication No. 85-23, revised 1996).

Support rats (300-400 g) were anesthetized with sodium pentobarbitone (60 mg/kg, intraperitoneally) and anticoagulated with heparin (1000 IU/kg intravenously). The right femoral vein and left femoral artery were exposed by blunt dissection and cannulated (18G and 22G Abbocath-T catheters respectively) for the return and supply of blood to the perfused heart. An extracorporeal circuit was established, primed with Gelofusine® plasma substitute (B. Braun Medical Ltd., Aylesbury, UK) and was maintained for 15 minutes (min) before connection to the isolated heart. This period was to ensure that the priming solution was adequately mixed with the blood of the support rat and that the entire preparation was stable. Each 500 ml of Gelofusine® contains 20.00 g succinated gelatin (average molecular weight 30,000), 3.65 g. sodium chloride, water for injection to 500 ml (electrolytes mmol/500 ml: cations Na 77, anions Cl 62.5, pH 7.4). Prior to perfusing the donor heart, an additional 7-8 ml of blood from a rat of the same strain was added to the central reservoir. This was to ensure that the support rat had an adequate supply of blood during the experiment when blood was not recirculated but instead collected for a 2 min period. A peristaltic pump (Gilson Minipuls 3) was located on the arterial outflow of the support rat and flow through the extracorporeal circuit was increased gradually over 10 min to a value of 2.5 ml/min. This gradual increase prevented the drop in arterial pressure that would have occurred if a flow rate of 2.5 ml/min had been established immediately. The blood was pumped through a cannula (to which the aorta of the perfused heart would subsequently be attached) and returned, by gravity, via a reservoir and filter to the venous inflow line of the support animal. An air-filled syringe above the perfusion cannula acted as a compliance chamber, which served to dampen oscillations in perfusion pressure which occurred as a consequence of the contraction of the isolated heart and the peristaltic action of the pump. The support animal was allowed to breathe a mixture of 95% $O_2$+5% $CO_2$ through a 35% Venturi face mask. The flow rate was adjusted to maintain blood $pO_2$ and $pCO_2$ within the physiological range. Body temperature was stabilized at 37.0 (±0.5)° C. by means of a thermostatically-controlled heating pad and was monitored by a rectal thermometer. Blood pressure was monitored by means of a pressure transducer attached to the arterial line. All pressure transducers were connected to a MacLab (ADInstruments, Australia), which was run continuously through the experiment. Blood gas ($pO_2$, $pCO_2$, pH), hematocrit, glucose and electrolyte levels ($Na^+$, $K^+$, $Ca^+$) of the support rat were monitored before the donor heart was attached to the extracorporeal circuit and at the end of each experiment. During the course of the experiment, minimum amounts of donor blood (from another at of the same strain) were transfused as required so as to maintain the volume and stability of the preparation. Additional heparin and pentobarbitone were administered into the central reservoir as required.

To isolate hearts, each rat (270-350 g) was anesthetized with diethyl ether and anticoagulated with heparin (1000 IU/kg intravenously). The heart was then immediately excised and immersed in cold (4° C.) Gelofusine®. The aorta was rapidly cannulated and perfused in the Langendorff mode, (Langendorff, *Pflugers Archives fur die Gestamte Physiologie des Menschen and der Tiere*, 61:291-332 (1895)) with arterial blood from the support animal, at a constant flow rate of 2.5 ml/min. After removal of the left atrial appendage, a fluid-filled balloon catheter (for the measurements of left ventricular systolic and diastolic pressures, and, by difference, left ventricular developed pressure), attached to a pressure transducer, was introduced into the left ventricle via the mitral valve. The balloon was inflated with water until a left ventricular end diastolic pressure (LVEDP) of between 4-8 mmHg was obtained. Heart rate was calculated from the pressure trace and expressed as beats per minute (bpm). Perfusion pressure was measured via a sidearm of the aortic cannula. All pressure transducers were connected to a MacLab, which was run continuously through the experiment.

Figure 9:
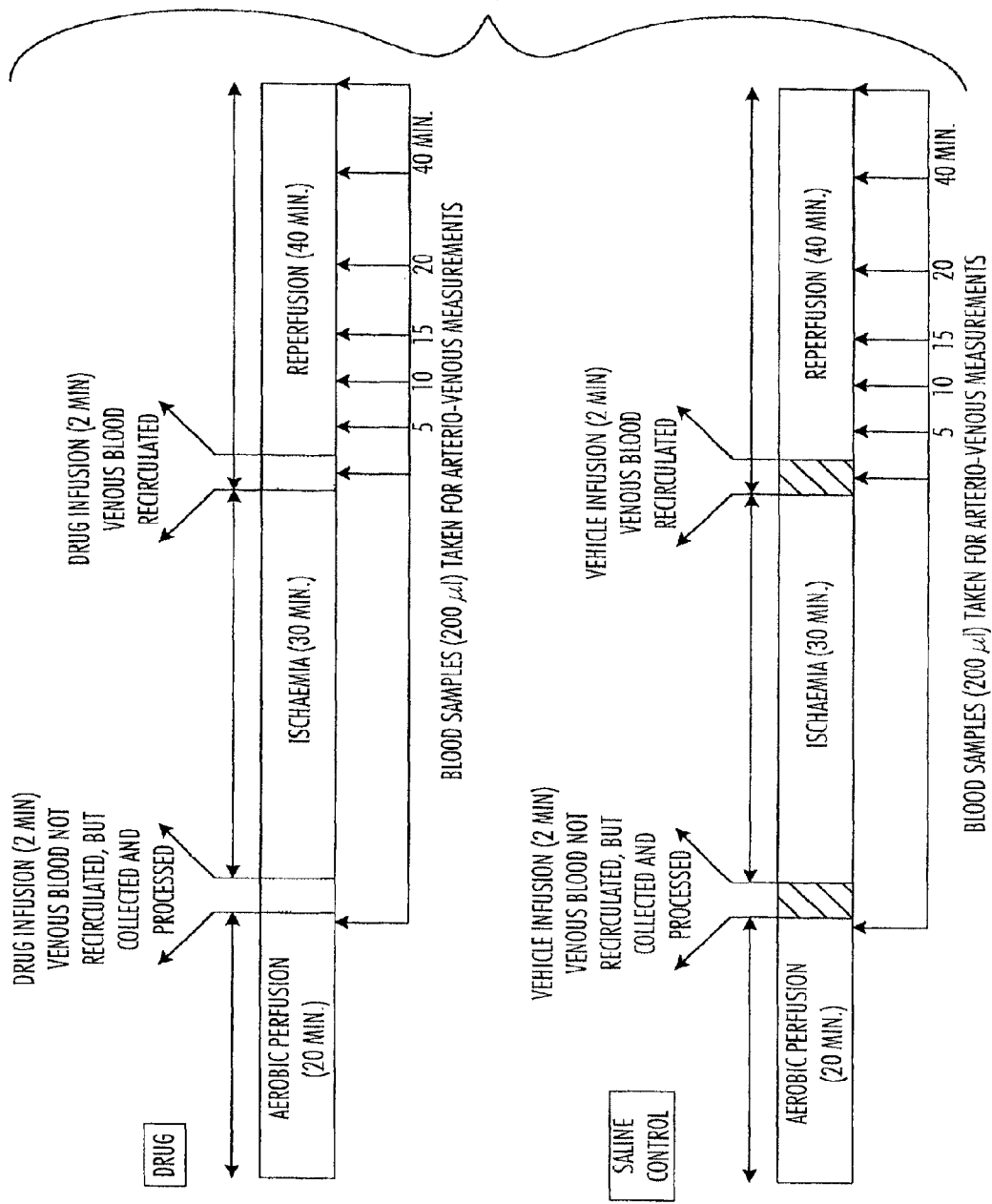
FIG. 9: Diagram of the treatments of isolated perfused hearts with drug and saline in the parabiotic blood perfusion system illustrated in FIG. 8.

Excised hearts were randomly assigned to two treatment groups (see FIG. 9; 6 hearts/group) and aerobically perfused for 20 min prior to (i) saline control with 2 min saline infusion immediately prior to a 30 min period of ischemia plus 2 min saline infusion at the onset of reperfusion and (ii) drug with 2 min drug infusion immediately prior to a 30 min period of ischemia (the drug was therefore trapped in the vasculature for the duration of the ensuing ischemic period), plus a 2 min drug infusion at the onset of reperfusion. Hearts were then subjected to 30 min of global, zero-flow ischemia, during which time they were immersed in saline at 37.0° C. Ischemia was initiated by clamping the line leading from the pump to the aortic cannula, thus diverting the flow away from the isolated heart back to the support animal, via the bypass line. Hearts were then reperfused for 40 min, during which time contractile function was continuously measured.

The drug, whose identity was unknown to the researchers performing the experiments, was the tetrapeptide D-Asp D-Ala D-His D-Lys. The tetrapeptide was supplied to the researchers by Bowman Research, UK, dissolved in saline at a concentration of 16.7 mg/mL. It was infused as supplied without any dilution or modification. Physiological saline was supplied by Baxter, UK and used in controls. Fresh solutions of saline and the drug were used daily.

Drug or vehicle was infused into a sidearm of the aortic cannula by means of a peristaltic pump (Gilson Minipuls 3), set at a constant flow of 0.25 ml/min. Since blood flow through the aortic cannula was 2.5 ml/min, and drug infusion was 0.25 ml/min, the final concentration of drug delivered to the heart was 1/11th of that supplied by Bowman Research. During the 2 min period of pre-ischemic vehicle or drug infusion and at the time points indicated in FIG. 9 arterial and venous blood samples were collected, centrifuged and frozen for analysis. The infusion was then repeated for the first 2 min of the reperfusion period, during which time the blood was not collected, but recirculated.

Predefined exclusion criteria stated that: (i) support animals would be excluded from the study if they did not attain a stable systolic blood pressure $\geq$80 mm Hg before cannulation of the donor heart, (ii) donor hearts would be excluded from the study if, at the 20 min baseline pre-intervention reading, LVDP$\leq$100 mm Hg or (iii) blood chemistry values were outside the normal range.

Results are expressed as mean±SEM. All recovery values are expressed as a percent of the pre-intervention baseline value (measured 20 min after the onset of the experiment) for each individual heart. The two-tailed unpaired Student's t test was used for the comparison of two means between groups. A difference was considered statistically significant when p <0.05.

For reasons of quality control and to allow application of predefined exclusion criteria, the stability and reproducibility of the system were monitored by measuring the blood chemistry (pH, $pO_2$, $pCO_2$, haematocrit, $Na^+$, $K^+$ and $Ca^{2+}$, glucose) and baseline contractile function of each support animal (immediately before perfusing a donor heart and at the end of each experiment) and each perfused heart. Table 3 reveals that there were only minor changes in each index measured, confirming that similar perfusion conditions applied in both study groups and that all values were within the acceptable physiological range. The systolic pressure and heart rate of the support rats are shown in Table 4. As can be seen, there were no significant differences between the two study groups at the 15 min baseline reading.

Table 5 shows that there were no significant differences between groups at the end of the 20 min aerobic perfusion period (i.e. just prior to the infusion of drug or vehicle) in LVDP, heart rate and perfusion pressure. Thus, for LVDP, the primary endpoint in the study, the mean values were 177.3±10.6 mmHg and 177.2±5.6 mmHg for the groups that were to become saline control and drug treated.

Figure 10:
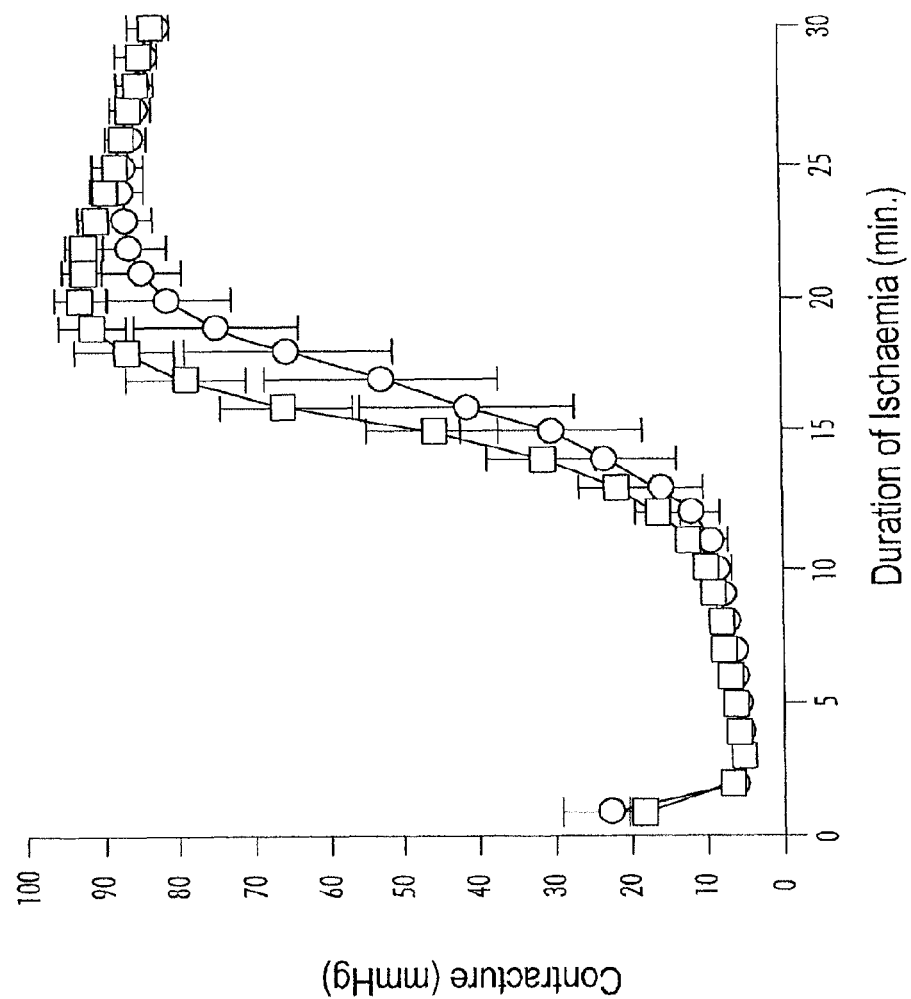
FIG. 10: Graph of contracture versus duration of ischemia showing the effect of a drug (D-Asp D-Ala D-His D-Lys) on contracture during ischemia in the blood-perfused rat heart model illustrated in FIGS. 8 and 9.

As expected, myocardial ischemia caused cessation of myocardial contraction, with cardiac arrest initially in the diastolic state. However, as ischemic injury developed with time an increase in diastolic state occurred as the heart went into ischemic contracture. The temporal profiles for the development of ischemic contracture in each of the study groups is shown in FIG. 10. As can be seen from Table 6, there were no differences in any of the measured indices, although there is some evidence of a trend to delay time-to-50% contracture in the drug treated group, which is suggestive with protection.

Figure 11:
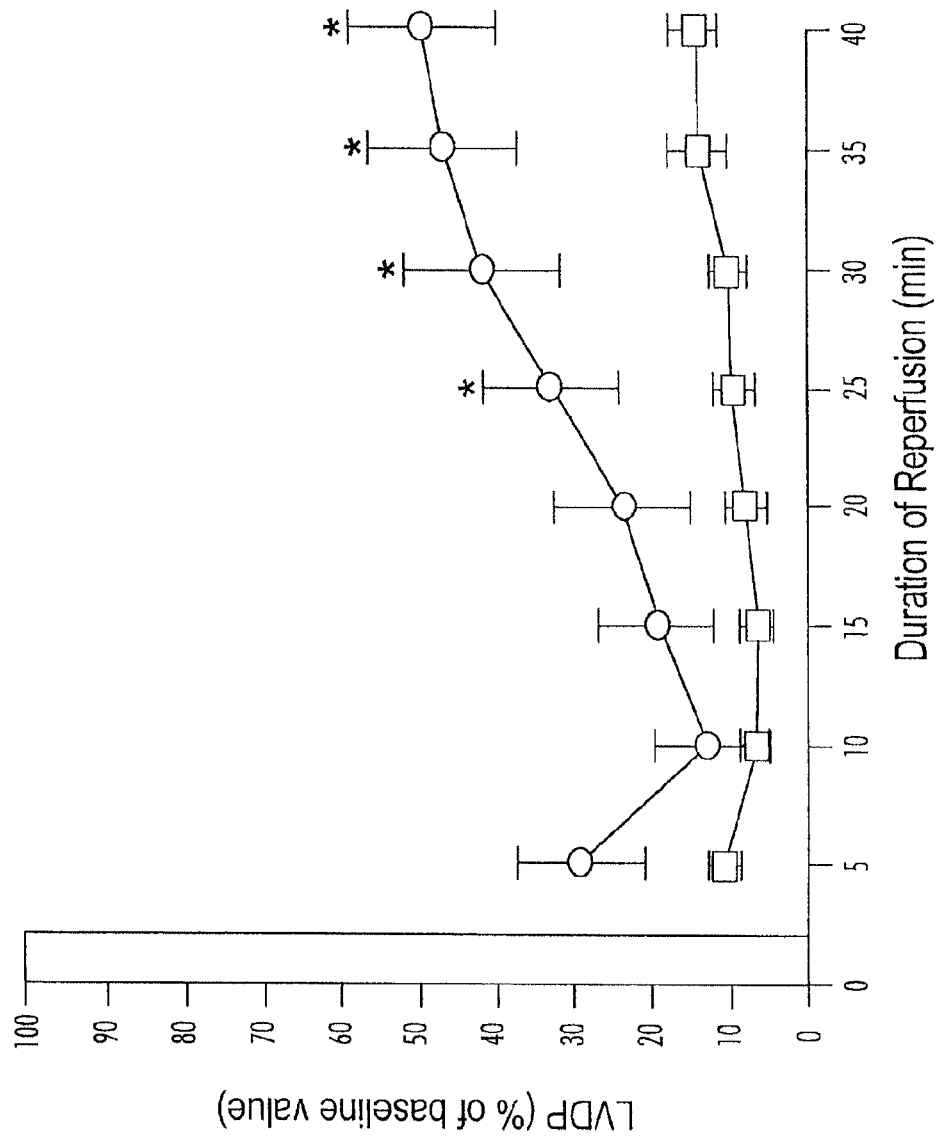
FIG. 11: Graph of left ventricle diastolic pressure (LVDP; expressed as a percentage of the 20-minute pre-intervention baseline value) versus duration of reperfusion showing the effect of the drug D-Asp D-Ala D-His D-Lys on post-ischemic recovery of LVDP in the blood-perfused rat heart model illustrated in FIGS. 8 and 9. * indicates $p \leq 0.05$.

FIG. 11 shows the profiles for the mean recovery of LVDP (expressed as a percent of baseline pre-intervention values) in both study groups. It is evident that hearts in the saline control group recovered slowly and poorly, such that by the end of the 40 min reperfusion period, LVDP was only 15.3±3.2% of the pre-intervention control. By contrast, hearts in the drug group recovered more rapidly and to a greater extent (50.5±9.3%).

Figure 12:
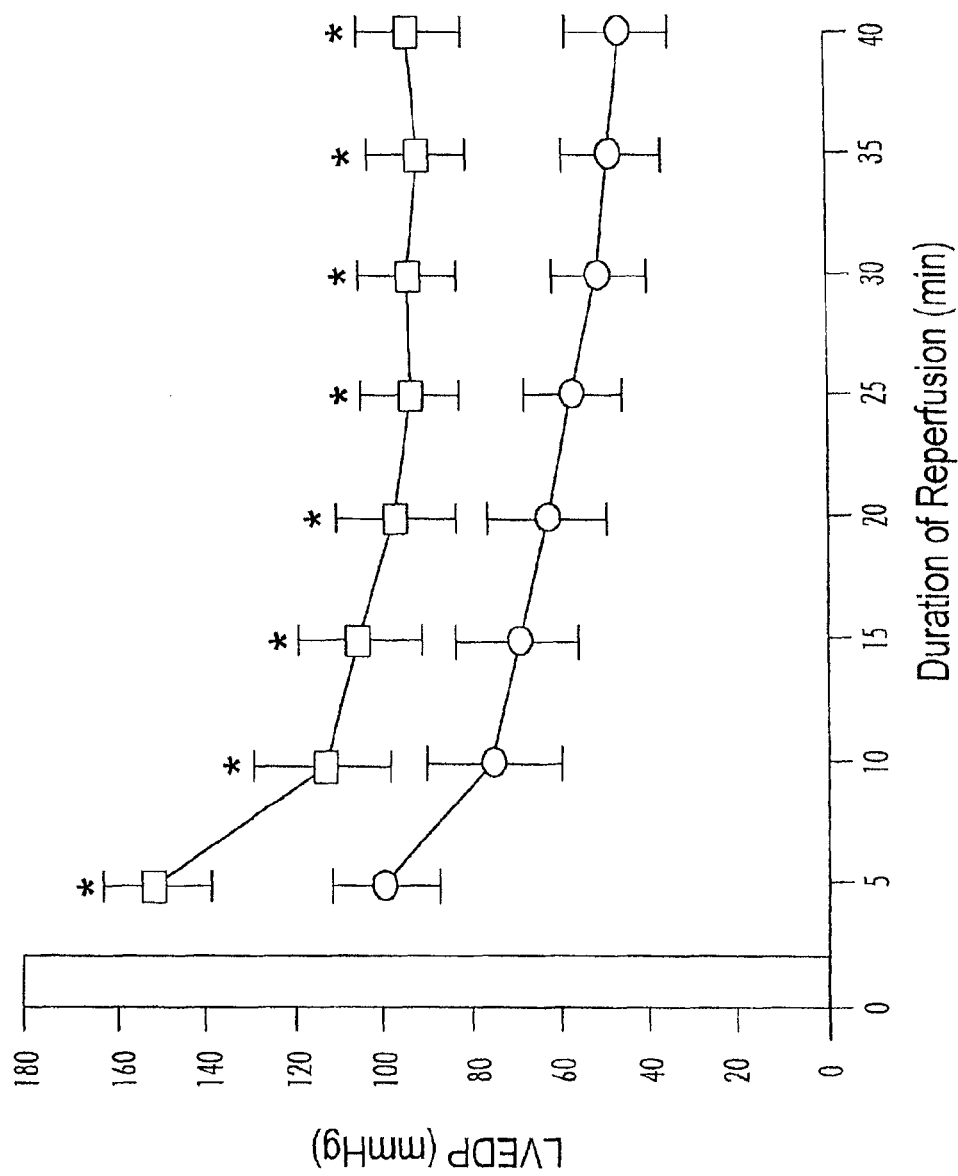
FIG. 12: Graph of left ventricle end diastolic pressure (LVEDP) versus duration of reperfusion showing the effect of the drug D-Asp D-Ala D-His D-Lys on post-ischemic recovery of LVEDP in the blood-perfused rat heart model illustrated in FIGS. 8 and 9. * indicates $p \leq 0.05$.

FIG. 12 shows the absolute values for the left ventricular end diastolic pressure in both study groups during the 40 min period of reperfusion. In both groups, the high levels of LVEDP resulting from the contracture which developed during ischaemia fell with time towards the pre-intervention control value. However, the drug group normalized their LVEDP more quickly and more completely than that seen in the saline control group, the difference being significant at every time point studied. This would be consistent with the enhanced recovery seen during reperfusion in the drug group.

Figure 13:
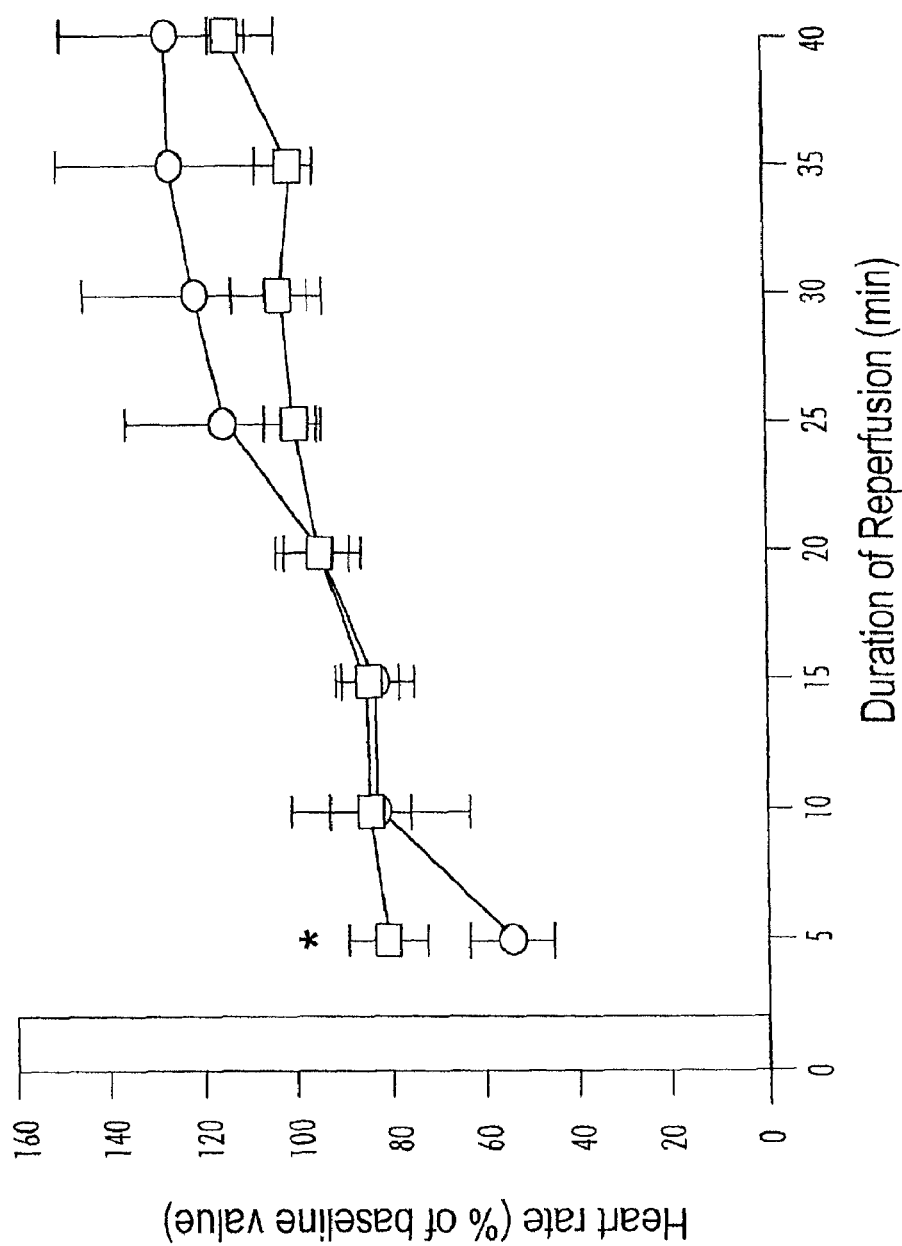
FIG. 13: Graph of heart rate (expressed as a percentage of the 20-minute pre-intervention baseline value) versus duration of reperfusion showing the effect of the drug D-Asp D-Ala D-His D-Lys on post-ischemic recovery of heart rate in the blood-perfused rat heart model illustrated in FIGS. 8 and 9. * indicates $p \leq 0.05$.

A comparison of the heart rates obtained in the saline control group and drug, as shown in FIG. 13 reveals that these two groups were essentially identical (115.0±3.8 versus 127.2±22.8%).

Figure 14:
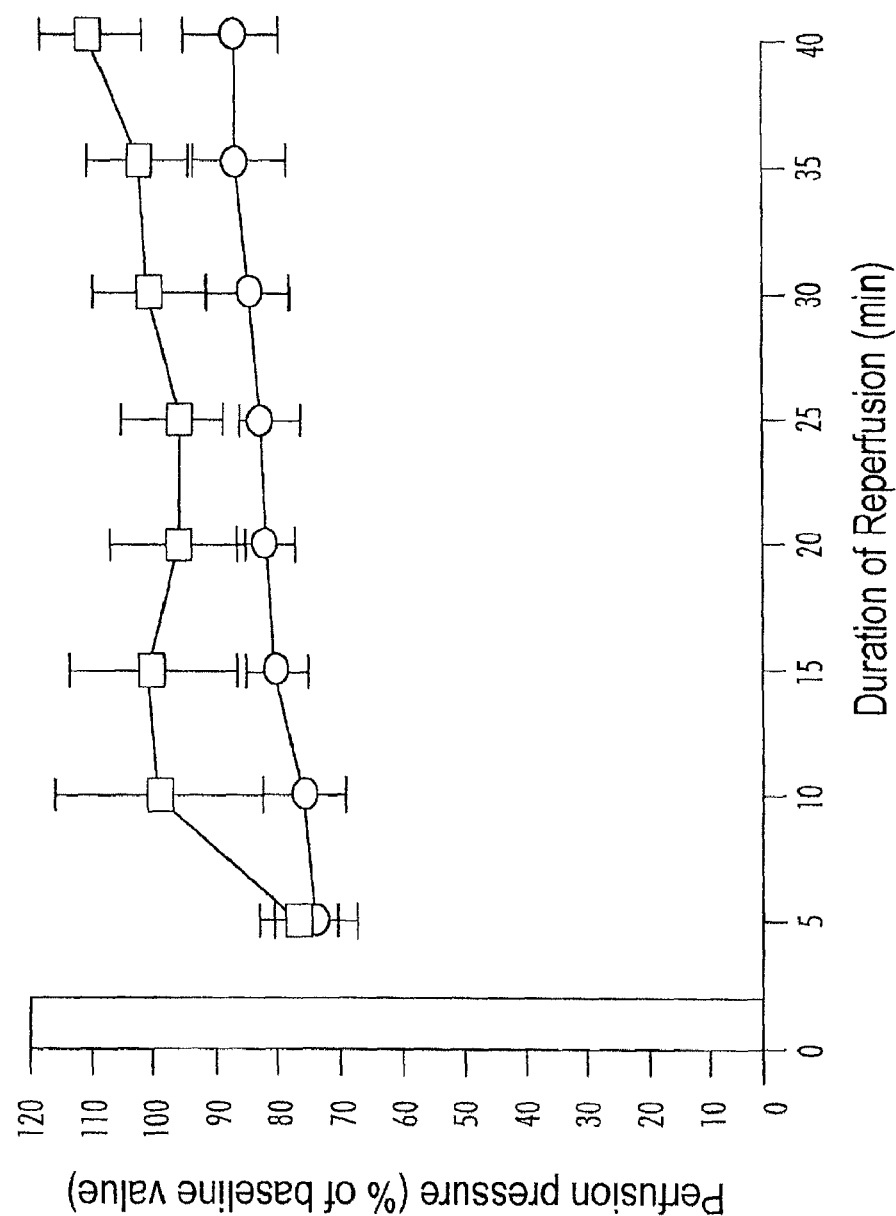
FIG. 14: Graph of perfusion pressure (expressed as a percentage of the 20-minute pre-intervention baseline value) versus duration of reperfusion showing the effect of the drug D-Asp D-Ala D-His D-Lys on post-ischemic recovery of perfusion pressure in the blood-perfused rat heart model illustrated in FIGS. 8 and 9.

As shown in FIG. 14, the perfusion pressure during the 40 min reperfusion period was essentially constant in both groups and the values did not differ significantly between each other at the end of the 40 min reperfusion period. In saline controls, the mean value at the end of reperfusion was 109.9±8.2% of its pre-intervention control, while that of the drug group was 87.4±8.0% of its pre-intervention value. Thus, although the values for drug tended to be lower throughout the reperfusion period (which is consistent with the observed cardioprotection), these changes did not reach statistical significance.

The results of this pilot study indicate that, in the isolated blood-perfused rat heart, Asp Ala His Lys appears to have significant and substantial protective properties as assessed by an approximately three and a half (3.5) fold (15.3±3.2% to 50.5±9.3%) enhancement of post-ischemic functional recovery. The magnitude of protection is equal to some of the most powerful interventions studied.

TABLE 3

Composition of the blood perfusing the isolated donor hearts

| Index | Value prior to attaching donor heart | | End of experiment | |
|---|---|---|---|---|
| | Saline Control | Drug* | Saline Control | Drug* |
| pH | 7.29 ± 0.01 | 7.26 ± 0.01 | 7.33 ± 0.02 | 7.31 ± 0.02 |
| $pCO_2$ (mmHg) | 60.0 ± 3.2 | 67.7 ± 2.2 | 57.6 ± 4.9 | 65.6 ± 4.7 |
| $pO_2$ (mmHg) | 230.6 ± 14.8 | 281.7 ± 23.2 | 241.0 ± 37.2 | 252.3 ± 33.9 |
| Haematocrit (%) | 27.5 ± 0.9 | 27.3 ± 1.8 | 26.8 ± 1.7 | 27.0 ± 1.5 |
| $Na^+$ (mmol/L) | 146.7 ± 0.3 | 146.2 ± 0.6 | 145.7 ± 0.2 | 146.2 ± 0.5 |
| $K^+$ (mmol/L) | 3.3 ± 0.1 | 3.2 ± 0.1 | 4.2 ± 0.2 | 4.2 ± 0.1 |
| $Ca^{2+}$ (mmol/L) | 1.2 ± 0.1 | 1.2 ± 0.1 | 1.4 ± 0.1 | 1.4 ± 0.1 |
| Glucose (mmol/L) | 8.9 ± 0.6 | 10.2 ± 0.3 | 10.2 ± 0.5 | 10.2 ± 0.7 |
| % oxygen saturation | 99.6 ± 0.1 | 99.8 ± 0.1 | 98.7 ± 1.2 | 99.7 ± 0.1 |

There were 4-6 support animals per group. All values are expressed as mean ± SEM.
*Drug was D-Asp D-Ala D-His D-Lys.

TABLE 4

Baseline systolic pressure and heart rate in the support blood-perfused rat

| Subsequent Treatment Group | Control values (t = 15 min aerobic perfusion) | |
|---|---|---|
| | Systolic Pressure (mmHg) | Heart Rate (bpm) |
| Saline Control | 96.4 ± 2.6 | 296.6 ± 9.8 |
| Drug* | 98.1 ± 3.8 | 297.6 ± 8.7 |

All values are expressed as mean ± SEM. There were 6 support animals per group.
*Drug was D-Asp D-Ala D-His D-Lys.

TABLE 5

Baseline left ventricular developed pressure (LVDP), heart rate and perfusion pressure in isolated blood-perfused rat hearts before various interventions

| Subsequent Treatment Group | Control values (t = 20 min aerobic perfusion) | | |
|---|---|---|---|
| | LVDP (mmHg) | Heart Rate (bpm) | Perfusion Pressure (mmHg) |
| Saline Control | 177.3 ± 10.6 | 236.6 ± 17.9 | 94.6 ± 7.5 |
| Drug* | 177.2 ± 5.6 | 257.3 ± 29.7 | 99.6 ± 7.3 |

All values are expressed as mean ± SEM. There were 6 support animals per group.
*Drug was D-Asp D-Ala D-His D-Lys.

TABLE 6

Ischemic contracture during 30 min of global, zero flow ischaemia

| Group | Contracture | | | |
|---|---|---|---|---|
| | Initiation (min) | Time-to-50% (min) | Peak (mmHg) | Time-to-peak (min) |
| Saline Control | 9.2 ± 1.6 | 15.1 ± 0.5 | 93.7 ± 3.0 | 19.8 ± 0.6 |
| Drug* | 11.9 ± 1.7 | 16.5 ± 0.9 | 89.5 ± 3.0 | 21.7 ± 1.2 |

All values are expressed as the mean ± SEM. There were 6 hearts per group.
*Drug was D-Asp D-Ala D-His D-Lys.

Example 9

Testing of Asp Ala His Lys In A Brain Ischemia Model

Focal ischemic infarcts were made in mature male Wistar rats (270-300 g, Charles River Laboratories) as described previously (Koizumi et al, *Jpn. J. Stroke,* 8:1-8 (1986); Chen et al., *J. Cereb.lood Flow Metab.,* 12(4):621-628 (1992)).

Animals were allowed free access to food and water before surgery. They were anesthetized with 3.5% halothane, and anesthesia was maintained with 1.0%-2.0% halothane in 70% $N_2$/30% $O_2$ using a face mask. Rectal temperature was maintained at 37° C. during surgery using a feedback-regulated water heating system (YSI 73A rectal probe, Fisher, connected to a K-20/64N aquatic blanket, Hamilton Industries, Cincinnati, Ohio). Previous studies have shown that rectal and brain temperatures are identical during and after ischemia in this model (Chen et al., *J. Cereb.lood Flow Metab.,* 12(4): 621-628 (1992)). The right femoral artery was cannulated with medical grade silicone tubing (Technical Products, Inc., Decatur, Ga.) for measurement of blood gases and blood pressure, and the femoral vein was cannulated for infusions. Cannulae were drawn through a subcutaneous tunnel and exited through the dorsal neck. Arterial blood gases were measured in all animals before and after ischemia.

For ischemia surgery, the right common carotid artery was exposed at its bifurcation. A 4-0 nylon suture, with its tip rounded by heating over a flame, was then advanced 18.5-19.5 mm (depending on the animal's weight) from the external into the internal carotid artery and then through the intracranial carotid artery until the tip occluded the origin of the middle cerebral artery (MCA). Animals were then allowed to awaken from anesthesia. At 2 hours after MCA occlusion, they were re-anaesthetized, and intra-arterial sutures were withdrawn into the external carotid artery.

Beginning one minute prior to occlusion, animals received an intravenous infusion of vehicle alone (control) or drug (D-Asp D-Ala D-His D-Lys) in vehicle over one minute. The identity of the drug was unknown to the researchers performing the experiments. It was supplied to the researchers as a concentrated stock (16.67 mg/ml) in phosphate buffered saline, pH 7.4, and was stored it at −80° C. The drug was determined to be biologically active prior to use by determining its ability to reduce free radical formation in vitro as described in Example 7. The stock solution was thawed just prior to use, and a sufficient quantity was administered to give a dose of 20 mg/kg. At the end of the intravenous administration of the drug or vehicle, the nylon suture was immediately advanced to occlude the MCA. Following the 2 hours of occlusion of the MCA, the animals received a repeat intravenous infusion of drug or vehicle over one minute. At the end of the second infusion, the nylon suture was immediately pulled back from occluding the MCA to allow for reperfusion. Also, after the second infusion, the animals were re-anesthetized, and the cannulae were removed. The animals were returned to their home cages, where they were allowed free access to food and water.

Animals were weighed before ischemia and before sacrifice. A neurological examination, as described in Zea Longa et al., *Stroke*, 20:84-91 (1989), was administered at 1 hour and at 24 hours after reperfusion. Scoring was as follows: 0, normal; 1, failure to extend contralateral (left) forepaw fully (amild focal neurologic deficit); 2, circling to the left (a moderate focal nuerologic deficit); 3, falling to the left (a several focal neurologic deficit); and 4, no spontaneous gait and depressed level of consciousness.

Twenty-four hours after MCA occlusion, animals were anesthetized with ketamine (44 mg/kg) and xylazine (13 mg/kg), both given intramuscularly, and perfused transcardially with heparinized saline, followed by 10% buffered formalin. The brains were removed and cut into 2-mm coronal slices using a rat brain matrix (Activational System, Inc., Warren, Mich.; a total of 7 slices). The slices were then embedded in paraffin, and 6-mm sections were cut from the anterior surface of each slice and stained with hematoxylin and eosin (H and E). Infarct volume was determined using a computer-interfaced image analysis system (Global Lab Image system, Data Translation, Marlboro, Mass.), using the "indirect" method (Swanson et al., *J. Cerebral Blood Flow Metabol.*, 10:290-293 (1990)): the area of intact regions of the ipsilateral (right) hemisphere and area of the intact contralateral (left) hemisphere were determined for each slice, the former was substracted from the latter to calculate infract area per slice. Infarct areas were then summed and multiplied by slice thickness to yield infarct volume per brain (in $mm^3$).

The results are presented in Tables 7-10 below. Some of the data are expressed as mean±S.E.M. Continuous data were analyzed by repeated measures ANOVA and paired or unpaired two-tailed t-tests with Bonferroni correction where appropriate. Non-continuous behavior date were analyzed by the Mann-Shitney U-test.

TABLE 7

Infarct Volume

| | Treated* | | Control |
|---|---|---|---|
| Animal | Infarct Volume ($mm^3$) | Animal | Infarct Volume ($mm^3$) |
| #1 | 11.5 | #2 | 44.5 |
| #3 | 14.7 | #4 | 32.3 |
| #5 | 43.3 | #6 | 39.4 |
| #7 | 10.9 | #8 | 22.2 |

TABLE 7-continued

Infarct Volume

| | Treated* | | Control |
|---|---|---|---|
| Animal | Infarct Volume ($mm^3$) | Animal | Infarct Volume ($mm^3$) |
| Mean | 20.1 | Mean | 34.6 |
| S.E.M. | 7.7 | S.E.M. | 4.8 |

*Treated with D-Asp D-Ala D-His D-Lys

TABLE 8

Neurological Scale

| | Treated* | | | Control | |
|---|---|---|---|---|---|
| Animal | Day $0^a$ | Day $1^b$ | Animal | Day $0^a$ | Day $1^b$ |
| #1 | 2 | 1 | #2 | 2 | 2 |
| #3 | 2 | 1 | #4 | 2 | 2 |
| #5 | 2 | 2 | #6 | 2 | 2 |
| #7 | 2 | 1 | #8 | 2 | 2 |

*Treated with D-Asp D-Ala D-His D-Lys
$^a$Day of ischemia surgery
$^b$One day after ischemia surgery

TABLE 9

Body Weight

| | Treated* | | | Control | |
|---|---|---|---|---|---|
| Animal | Day $0^a$ | Day $1^b$ | Animal | Day $0^a$ | Day $1^b$ |
| #1 | 300 | 272 | #2 | 300 | 251 |
| #3 | 300 | 266 | #4 | 300 | 256 |
| #5 | 295 | 256 | #6 | 278 | 230 |
| #7 | 295 | 255 | #8 | 300 | 250 |

*Treated with D-Asp D-Ala D-His D-Lys
$^a$Day of ischemia surgery
$^b$One day after ischemia surgery

TABLE 10

Blood Gases And Blood Pressure 10 minutes before MCA occlusion

| | | | | 10 minutes after MCA occlusion | | | |
|---|---|---|---|---|---|---|---|
| Animal | pH | $pCO_2$ | $pO_2$ | $BP^c$ | Animal | pH | $pCO_2$ | $pO_2$ | $BP^c$ |

| Animal | pH | $pCO_2$ | $pO_2$ | $BP^c$ | Animal | pH | $pCO_2$ | $pO_2$ | $BP^c$ |
|---|---|---|---|---|---|---|---|---|---|
| #1 | 7.437 | 38.5 | 117.1 | 96 | #1 | 7.422 | 40.2 | 130.1 | 106 |
| #3 | 7.430 | 38.3 | 110.5 | 89 | #3 | 7.423 | 40.1 | 130.1 | 98 |
| #5 | 7.518 | 38.5 | 147.0 | 98 | #5 | 7.471 | 36.5 | 105.3 | 92 |
| #7 | 7.423 | 33.4 | 97.4 | 86 | #7 | 7.433 | 34.0 | 139.9 | 89 |
| #2 | 7.401 | 35.5 | 120.1 | 90 | #2 | 7.423 | 40.1 | 130.1 | 103 |
| #4 | 7.440 | 38.5 | 121.1 | 93 | #4 | 7.421 | 39.5 | 129.3 | 101 |
| #6 | 7.425 | 35.9 | 110.0 | 88 | #6 | 7.453 | 36.2 | 105.3 | 92 |
| #8 | 7.417 | 39.5 | 120.7 | 90 | #8 | 7.428 | 36.9 | 111.0 | 93 |

Example 10

Inhibition of the Generation of ROS

The ability of the tetrapeptide L-Asp L-Ala L-His L-Lys [SEQ ID NO:1] and other peptides and compounds to inhibit the production of ROS was tested. The other peptides tested were: L-Asp L-Ala L-His L-Lys L-Ser L-Glu L-Val L-Ala L-His L-Arg L-Phe L-Lys [SEQ ID NO:3]; L-Ala L-His L-Lys L-Ser L-Glu L-Val L-Ala L-His L-Arg L-Phe L-Lys [SEQ ID NO:4]; L-His L-Lys L-Ser L-Glu L-Val L-Ala L-His L-Arg L-Phe L-Lys [SEQ ID NO:5]; and Acetylated-L-Asp L-Ala L-His L-Lys L-Ser L-Glu L-Val L-Ala L-His L-Arg L-Phe L-Lys [SEQ ID NO:6]. The peptides were obtained from one or more companies that provide custom synthesis of peptides, including Ansynth Services, QCB, Genosys and Bowman Research. The other compounds tested were histidine (Sigma Chemical Co.), catalase (Sigma Chemical Co.), and superoxide dismutase (Sigma Chemical Co.).

1. Inhibition of Hydroxyl Radical Production

The hydroxyl radical is probably the most reactive oxygen-derived species. The hydroxyl free radical is very energetic, short-lived and toxic.

Some researchers suggest that the toxicity of hydrogen peroxide and superoxide radical may be due to their conversion to the hydroxyl free radical. The superoxide radical can be directly converted to the hydroxyl radical via the Haber-Weiss reaction. Alternatively, it can be converted to hydrogen peroxide which, in turn, is converted into the hydroxyl radical via the Fenton reaction. Both pathways require a transition metal, such as copper (Acworth and Bailey, *The Handbook Of Oxidative Metabolism* (ESA, Inc. 1997)).

It is also known that copper, in the presence of ascorbate, produces hydroxyl radicals. The following reaction scheme has been suggested:

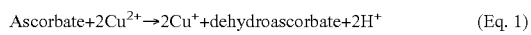

$$\text{Ascorbate} + 2\text{Cu}^{2+} \rightarrow 2\text{Cu}^{+} + \text{dehydroascorbate} + 2\text{H}^{+} \quad \text{(Eq. 1)}$$

$$\text{Cu}^{+} + \text{O}_2 \rightarrow \text{O}_2^{\cdot-} + \text{Cu}^{2+} \quad \text{(Eq. 2)}$$

$$\text{Cu}^{+} + \text{O}_2^{\cdot-} + 2\text{H}^{+} \rightarrow \text{Cu}^{2+} + \text{H}_2\text{O}_2 \quad \text{(Eq. 3)}$$

$$\text{Cu}^{+} + \text{H}_2\text{O}_2 \rightarrow \text{OH}^- + \text{OH}^{\cdot} + \text{Cu}^{2+} \quad \text{(Eq. 4)}$$

Biaglow et al., *Free Radic. Biol. Med.*, 22(7):1129-1138 (1997).

The ability of the compounds listed above to inhibit the generation of hydroxyl radicals was tested as described in Gutteridge and Wilkins, *Biochim. Biophys. Acta*, 759:38-41 (1983). Briefly, Cu(II) and ascorbic acid were mixed causing the generation of hydroxyl radicals. Then, deoxyribose was added, and the hydroxyl radicals, if present, attacked the deoxyribose to produce fragments. Heating the fragments at low pH produced malonaldehyde that, upon the addition of 2-thiobarbituric acid (TBA), yielded a pink chromogen which was measured spectrophotometrically at 532 nm. Thus, absorbance at 532 nm is a measure of the damage to deoxyribose and, therefore, of hydroxyl radical formation.

To perform the assay, $CuCl_2$ in buffer (20 mM $KH_2PO_4$ buffer, pH 7.4) and either one of the test compounds in buffer or buffer alone were added to test tubes (final concentration of $CuCl_2$ was 10 µM). The test tubes were incubated for 15 minutes at room temperature. Then, 0.5 mM ascorbic acid in buffer and 1.9 mM 2-deoxy-D-ribose in buffer were added to each test tube, and the test tubes were incubated for 1 hour at 37° C. Finally, 1 ml of 1% (w/v) TBA in 50 mM NaOH and 1 ml of concentrated acetic acid were added to each test tube, and the test tubes were incubated in boiling water for 15 minutes. After the test tubes had cooled for 15 minutes, the absorbance at 532 nm was read.

It was found that the tetrapeptide L-Asp L-Ala L-His L-Lys [SEQ ID NO:1] caused complete inhibition of the formation of hydroxyl radicals in this assay at tetrapeptide/copper ratios of 2:1 or higher. Tetrapeptide/copper ratios less than 2:1 were ineffective.

Figure 15A:
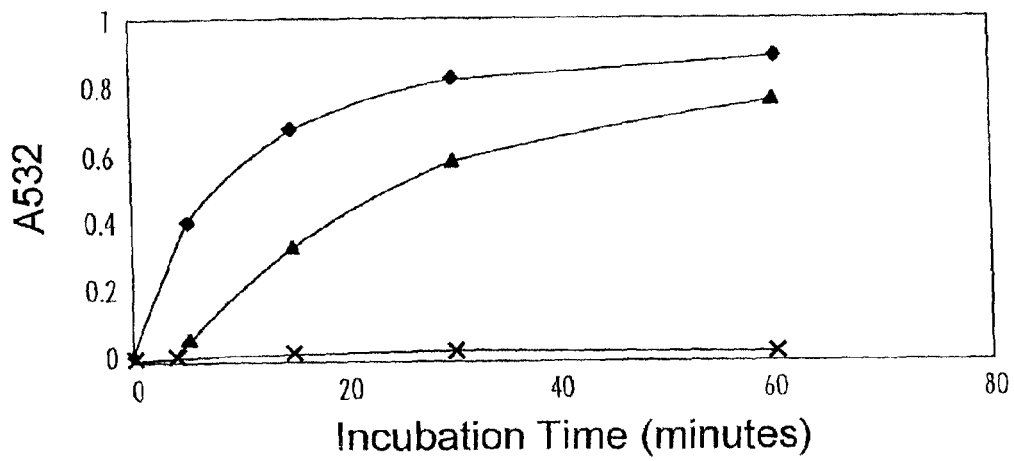
FIG. 15A-B: Graphs of absorbance at 532 nm (A532) versus incubation time in an assay for the production of hydroxyl radicals.

The results of a time course are presented in FIG. 15A. As can be seen in FIG. 15A, copper and ascorbate (no added peptide) produced TBA-reactive substances quickly and reached a maximum in 30 minutes. The tetrapeptide at a tetrapeptide/copper ratio of 2:1 prevented all formation of TBA-reactive substances. Interestingly, the tetrapeptide at a tetrapeptide/copper ratio of 1:1 slowed the production of TBA-reactive substances. These data suggest that the tetrapeptide at a 1:1 tetrapeptide/copper ratio is able to offer some protection from hydroxyl radicals by binding copper which results in site-directed hydroxyl attack on the tetrapeptide. Once enough of the tetrapeptide is destroyed, then copper is released, which allows it to produce hydroxyl radicals that attack the dexoyribose.

Figure 15B:
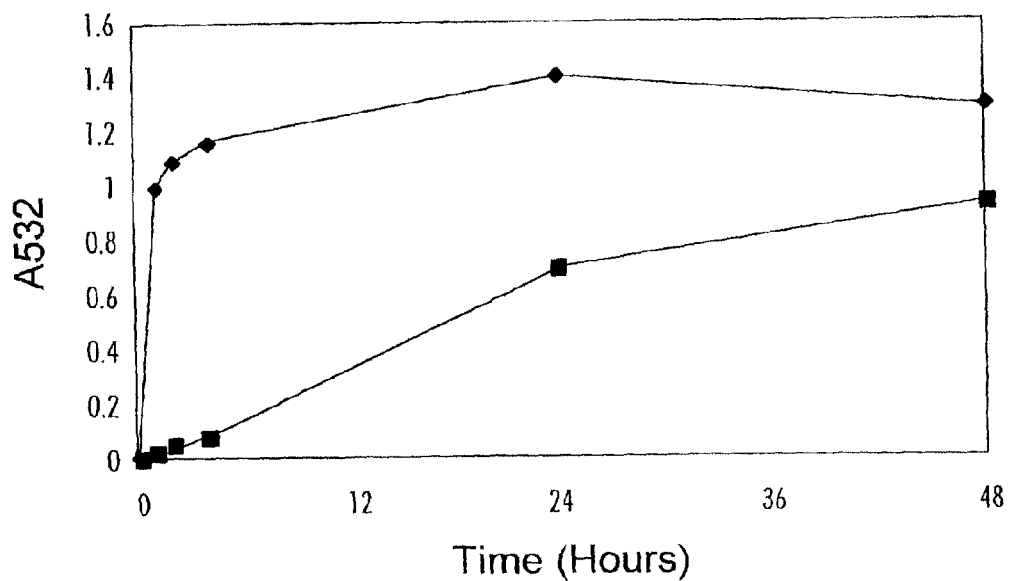

When the tetrapeptide at a tetrapeptide/copper ratio of 2:1 was incubated for longer periods of time, its ability to prevent the formation of TBA-reactive substances slowly eroded. See FIG. 15B. As can be seen from FIG. 15B, the production of TBA-reactive substances was inhibited by 95% during the first 4 hours of incubation. By 24 hours, the level of inhibition had dropped to 50% and, by 48 hours, the level of inhibition had dropped to 20%. These data suggest that TBA-reactive substances are still being produced even in the presence of the tetrapeptide. They also suggest that the tetrapeptide is being degraded during the time course of the experiment. This degradation is more than likely due to the formation of free radicals in close proximity to the tetrapeptide/copper complex which attack and degrade the tetrapeptide, with release of the copper. Since free radicals, such as the hydroxyl radical, are very reactive, they will attack the first electron rich molecule they come into contact with, which would be the tetrapeptide in this case.

The effect of pH on the inhibition of hydroxyl radical formation by the tetrapeptide was tested at a tetrapeptide/copper ratio of 2:1. At this ratio, the tetrapeptide gave >95% inhibition of the formation of TBA-reactive species at pH 7.0-8.5. These are physiological pH levels and pH levels that would be expected during ischemia (acidosis occurs in ischemic tissues). At pH 6.0, the tetrapeptide was ineffective at preventing the formation of TBA-reactive species, possibly due to the reduced ability of the histidine to bind copper. The nitrogen atom on the imidazole ring of histidine participates in binding copper with a pKa of 6.0. Therefore, at a pH of 6.0, histidine is only able to bind 50% of the copper. The other 50% of the copper would be unbound or loosely bound to the tetrapeptide by the other amino acids and would, therefore, be able to participate in the production of TBA-reactive species.

Histidine and several peptides with histidine in different positions were tested at 1:1 and 2:1 peptide:copper ratios for their ability to inhibit the production of hydroxyl radicals. Also, a peptide having an acetylated aspartic acid (Ac-Asp) as the N-terminal amino acid was also tested. The results are presented in Table 11. In Table 11, the % inhibition is the percent decrease in absorbance compared to buffer alone divided by the absorbance of the buffer alone.

As can be seen from the results in Table 11, the peptides with histidine in the second and third positions gave >95% inhibition at a 2:1 peptide:copper ratio, while these peptides at a 1:1 peptide:copper ratio were ineffective. Interestingly, at a 2:1 peptide:copper ratio, the peptide with histidine in the first position and the peptide with acetylated aspartic acid as the N-terminal amino acid provided some protection (about 47% and about 28% inhibition, respectively), although this protection might be attributable to the histidine in the seventh and ninth positions, respectively, of these peptides. Histidine alone at a 2:1 histidine:copper ratio provided some protection (about 20% inhibition).

Catalase has been shown to prevent hydroxyl radical formation. Gutteridge and Wilkins, *Biochim. Biophys. Acta,*

759:38-41 (1983); Facchinetti et al., *Cell. Molec. Neurobiol.*, 18(6):667-682 (1998); Samuni et al., *Eur. J. Biochem.*, 137: 119-124 (1983). Catalase (0-80 nM) was, therefore, tested in this assay, and it was found to prevent the formation of the pink chromogen (data not shown). This finding suggests that hydrogen peroxide is formed in this assay, since catalase breaks down hydrogen peroxide to water and agrees with Equations 3 and 4 above. Catalase also prevents the formation of the pink chromogen when the L-Asp L-Ala L-His L-Lys [SEQ ID NO:1] tetrapeptide at a tetrapeptide/copper ratio of 1:1 is present (data not shown). As shown above, at this ratio, the copper is still able to participate in the redox reactions to produce hydroxyl radicals. These experiments show that hydrogen peroxide is an important precursor to the formation of the hydroxyl radical.

39(4):813-821 (1996); Ciuffi et al., *Pharmacol Res.*, 38(4): 279-287 (1998); Pogni et al., *J. Inorg. Biochem.*, 73:157-165 (1999); Willingham and Sorenson, *Biochem. Biophys. Res. Commun.*, 150(1):252-258 (1988); Konstantinova et al., *Free Rad. Res. Comms.*, 12-13:215-220 (1991); Goldstein et al., *J. Am. Chem. Soc.*, 112:6489-6492 (1990). This finding is not surprising since SOD itself has copper in its active site.

The SOD activity of copper complexes of the tetrapeptide L-Asp L-Ala L-His L-Lys [SEQ ID NO: 1] was assayed. Superoxide radicals were produced using the xanthine oxidase assay of Beauchamp and Fridovich, *Anal. Biochem.*, 44:276-287 (1971). Xanthine oxidase converts xanthine into uric acid, with oxygen acting as an electron acceptor. This causes superoxide radical to be produced. Superoxide radical is able to reduce nitro blue tetrazolium (NBT). Reduced NBT

TABLE 11

| Compound (Ratio)[a] | Absorbance at 532 nm | Absorbance at 532 nm | % Inhibition |
|---|---|---|---|
| Copper only (buffer control) | 0.767* | 0.954 | 0 |
| Histindine/copper (2:1) | | 0.760 | 20.3 |
| His Lys Ser Glu Val Ala His Arg Phe Lys[b]/copper (1:1) | | 0.716 | 24.9 |
| His Lys Ser Glu Val Ala His Arg Phe Lys[b]/copper (2:1) | | 0.509 | 46.6 |
| Ala His Lys Ser Glu Val Ala His Arg Phe Lys[c]/copper (1:1) | | 0.843 | 11.6 |
| Ala His Lys Ser Glu Val Ala His Arg Phe Lys[c]/copper (2:1) | | 0.047 | 95.1 |
| Asp Ala His Lys Ser Glu Val Ala His Arg Phe Lys[d]/copper (1:1) | 0.645 | | 13.2 |
| Asp Ala His Lys Ser Glu Val Ala His Arg Phe Lys[d]/copper (2:1) | 0.040 | | 95.8 |
| Ac-Asp Ala His Lys Ser Glu Val Ala His Arg Phe Lys[e]/copper (1:1) | 0.633 | | 16.9 |
| Ac-Asp Ala His Lys Ser Glu Val Ala His Arg Phe Lys[e]/copper (2:1) | 0.692 | | 27.5 |
| Asp Ala His Lys[f]/copper (1:1) | 0.751* | | 1.3 |
| Asp Ala His Lys[f]/copper (2:1) | 0.029* | | 96.2 |

[a]All amino acids are L-amino acids.
[b]SEQ ID NO: 5
[c]SEQ ID NO: 4
[d]SEQ ID NO: 3
[e]SEQ ID NO: 6
[f]SEQ ID NO: 1
*Data taken from Table 2 in Example 7.

B. Assay For Superoxide Dismutase (SOD) Activity

The enzyme superoxide dismutase (SOD) is a naturally-occurring enzyme which is responsible for the breakdown in the body of superoxide to hydrogen peroxide (similar to Equation 3). Hydrogen peroxide can then be detoxified by catalase.

SOD was assayed for activity in the assay described in the previous section and was found to have none (data not shown). This result is not surprising since SOD actually converts superoxide radical into hydrogen peroxide. Hydrogen peroxide can then be converted into the hydroxyl radical by reduced copper.

There are reports in the literature that copper complexes have SOD activity. Athar et al., *Biochem. Mol. Biol. Int.*, has a λmax of 560 nm. It is known that copper inhibits xanthine oxidase activity (Konstantinova et al., *Free Rad. Res. Comms.*, 12-13:215-220 (1991)), so all experiments containing copper also contained ethylenediaminetetracetic acid (EDTA), a known copper chelator. The EDTA-copper complex was tested for SOD activity and was shown to have no SOD activity (data not shown).

To perform the assay for SOD activity, 0.1 mM xanthine (Sigma Chemical Co.), 25 μM NBT (Sigma Chemical Co.), 50 mM sodium carbonate, and 1.2 μM EDTA (Sigma Chemical Co.), were mixed in a cuvette (all final concentrations, final pH 10.2). The reaction was started by the addition of various amounts of a tetrapeptide-copper complex (tetrapeptide/copper ratios of 1:1 and 2:1) and 20 nM xanthine oxidase (Sigma Chemical Co.). The tetrapeptide-copper complex was prepared by mixing the tetrapeptide and copper (as $CuCl_2$) and allowing the mixture to incubate for 15 minutes at room temperature immediately before addition to the cuvette. The samples were read at time 0 and every 60 seconds for five minutes at 560 nm.

Figure 16:
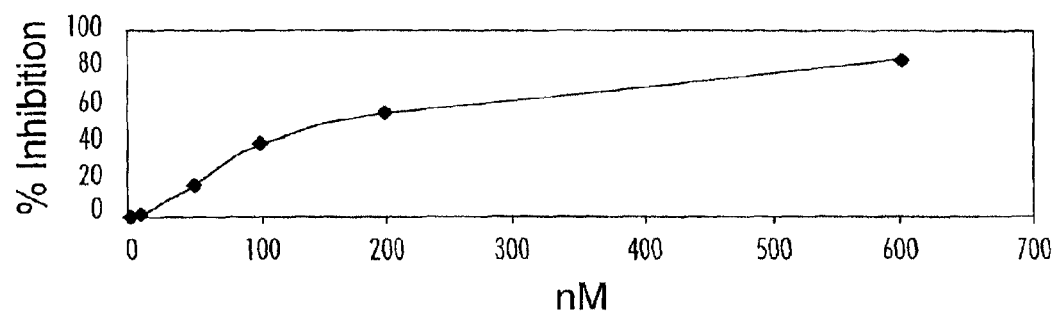
FIG. 16: Graph of % inhibition versus concentration tetrapeptide (L-Asp L-Ala L-His L-Lys [SEQ ID NO:1])-copper complex at a tetrapeptide/copper ratio of 1:1 in the xanthine oxidase assay for superoxide dismutase activity.

The complex of the tetrapeptide with copper at a ratio of 1:1 was shown to have SOD activity, as evidenced by inhibition of NBT reduction (see FIG. 16). However, the complex was about 500 times less effective than SOD itself, based on $IC_{50}$ values (amount that gives 50% inhibition) in this assay. The complex of the tetrapeptide with copper at a ratio of 2:1 was found to have no SOD activity (data not shown).

To verify that the 1:1 tetrapeptide-copper complex did not interfere with xanthine oxidase activity, uric acid production was measured at 295 nm. Athar et al., *Biochem. Mol. Biol. Int.*, 39(4):813-821 (1996); Ciuffi et al., *Pharmacol Res.*, 38(4):279-287 (1998). This assay is similar to the SOD assay, except that NBT is not present. Instead, uric acid is assayed at 295 nm every 60 seconds for 5 minutes. It was found that the 1:1 tetrapeptide-copper complex only inhibited uric acid production by 11% at a concentration of 600 nM (data not shown). Therefore, the 1:1 tetrapeptide-copper complex has true SOD activity. Since superoxide is converted to hydrogen peroxide by the complex, this could help to explain why it is not effective at preventing hydroxyl radical production.

Figure 17:
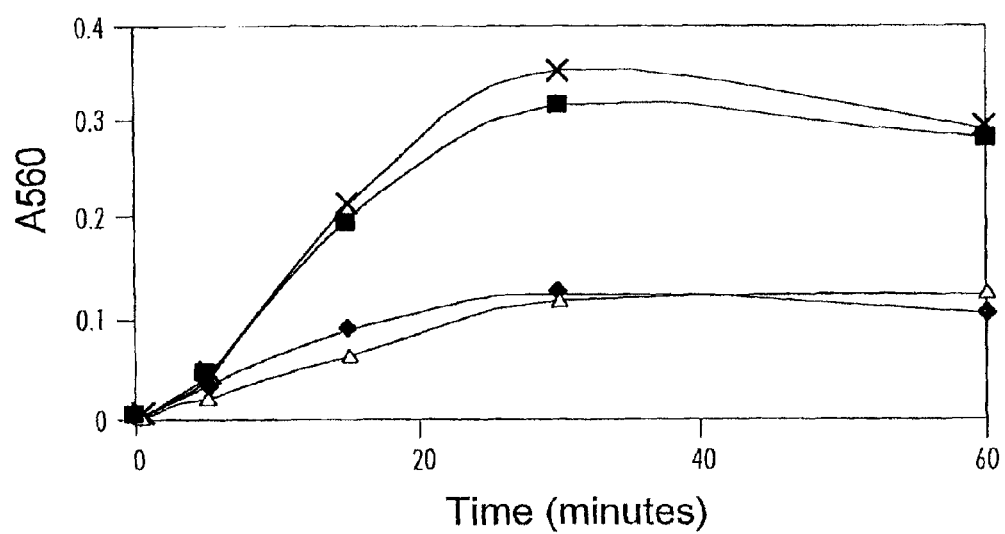
FIG. 17: Graph of absorbance at 560 nm (A560) versus time in an assay for superoxide radical production.

Superoxide radical production was measured in solutions containing the 1:1 or 2:1 tetrapeptide-copper complexes. The assay combined techniques from the TBA assay and the xanthine oxidase assay. NBT was added to all test tubes in order to quantitate its reduction by superoxide radical. The samples also contained ascorbate and copper and were incubated at 37° C. At 5, 15, 30 and 60 minutes, the samples were removed from the incubator and read at 560 nm. The results are shown in FIG. 17. In the sample containing the 2:1 tetrapeptide-copper complex, NBT reduction increased over time and reached a maximum at 30 minutes. The sample containing the 1:1 tetrapeptide-copper complex also showed an increase in NBT reduction, with a decreased maximum reached at 60 minutes. These data suggest that superoxide accumulates in the sample containing the 2:1 tetrapeptide-copper complex, while the 1:1 tetrapeptide-copper complex mimics superoxide dismutase.

The likely sequence of events that occurs in the production of hydroxyl radicals is as follows:

$$O_2 \rightarrow O_2^{\bullet-} \rightarrow H_2O_2 \rightarrow OH^{\bullet} \qquad (Eq. 5).$$

It has already been shown that the 1:1 tetrapeptide-copper complex can convert superoxide radical ($O_2^{\bullet-}$) into hydrogen peroxide ($H_2O_2$). This is the SOD activity of the complex. The 2:1 tetrapeptide-copper complex cannot facilitate this conversion since the two molecules of the tetrapeptide fill all six coordination bonds of copper. This explains why the 2:1 tetrapeptide-copper complex is so effective because it inhibits the formation of hydrogen peroxide, which could in turn react with reduced copper to produce hydroxyl radicals via the Fenton reaction. The 1:1 tetrapeptide-copper complex also provides a valuable service by eliminating the superoxide radical. Even though it produces hydrogen peroxide, most compartments of the human body have sufficient quantities of the enzyme catalase that can eliminate hydrogen peroxide. In the brain, however, catalase activity is reported to be minimal. Halliwell et al., *Methods in Enzymol.*, 186:1-85 (1990). Therefore, the brain is a particularly vulnerable organ during periods of ischemia, since copper is released due to the acidosis that accompanies ischemia.

C. Protection of DNA

DNA strand breaks were measured according to the method of Asaumi et al., *Biochem. Mol. Biol. Int.*, 39(1):77-86 (1996). Briefly, 17 µg/ml of plasmid pBR322 DNA was allowed to pre-incubate for 15 minutes at room temperature with 50 µM $CuCl_2$ and concentrations of the tetrapeptide of 0-200 µM. Then, 2.5 mM ascorbate was added to each reaction, and the mixture was incubated for 1 hour at 37° C. The total volume of the mixture was 16 µL. Next, 3 µL of loading buffer containing 0.25% (w/v) bromophenol blue, 0.25% (w/v) xylene cyanole FF, and 40% (w/v) sucrose in water was added. The samples were separated by electrophoresis in a 0.8% agarose gel for 90 minutes at 70 Volts. The gel was stained in 1×TBE (Tris-Borate-EDTA buffer) containing 2 µg/ml ethidium bromide for 30 minutes. The gel was then destained in 1×TBE for 5 minutes prior to photographing the gel.

Figure 18:
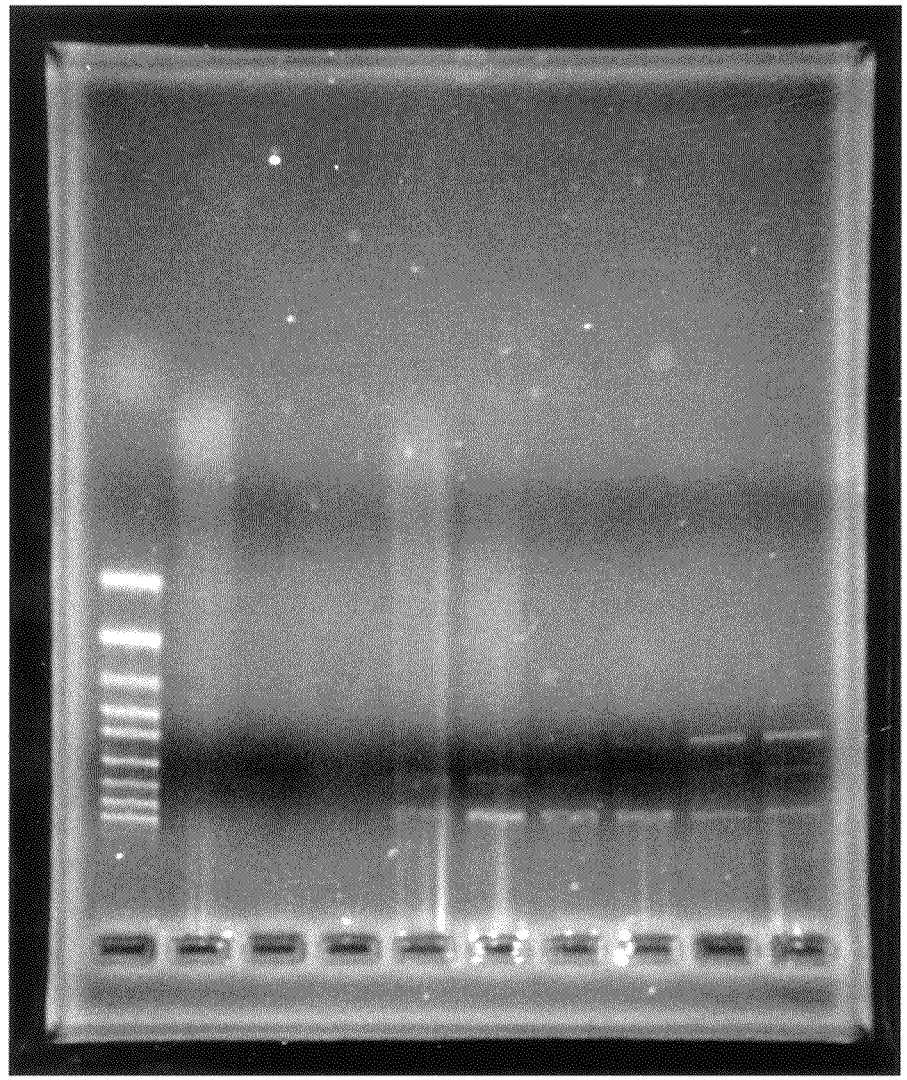
FIG. 18: Gel after electrophoresis of DNA treated in various ways. Lane 1-17 μg/ml plasmid DNA (untreated control); Lane 2-17 μg/ml plasmid DNA and 50 μM $CuCl_2$; Lane 3-17 μg/ml plasmid DNA and 2.5 mM ascorbate; Lane 4-17 μg/ml plasmid DNA, 2.5 mM ascorbate, 50 μM $CuCl_2$, and 200 μM tetrapeptide (L-Asp L-Ala L-His L-Lys [SEQ ID NO:1]) (4:1 ratio tetrapeptide/copper); Lane 5-17 μg/ml plasmid DNA, 2.5 mM ascorbate, 50 μM $CuCl_2$, and 100 μM tetrapeptide (2:1 ratio tetrapeptide/copper); Lane 6-17 μg/ml plasmid DNA, 2.5 mM ascorbate, 50 μM $CuCl_2$, and 50 μM tetrapeptide (1:1 ratio tetrapeptide/copper); Lane 7-17 μg/ml plasmid DNA, 2.5 mM ascorbate, 50 μM $CuCl_2$, and 25 μM tetrapeptide (1:2 ratio tetrapeptide/copper); Lane 8-17 μg/ml plasmid DNA, 2.5 mM ascorbate, 50 μM $CuCl_2$, and 12.5 μM tetrapeptide (1:4 ratio tetrapeptide/copper); Lane 9-17 μg/ml plasmid DNA, 2.5 mM ascorbate, and 50 μM $CuCl_2$ (positive control); and Lane 10—DNA ladder.

The results showed that the tetrapeptide was very effective at preventing the formation of DNA strand breaks. See FIG. 18. Optimal protective tetrapeptide:copper ratios were 2:1 and greater, since superhelical circular DNA was still visible on the gel at these ratios. At a tetrapeptide:copper ratios of 1:1 or less, nicked circular DNA, linear DNA and more damaged DNA (smears) were visible.

Example 11

Reduction of the Damage Done to DNA by ROS

ROS damages DNA by causing strand breaks, base modifications, point mutations, altered methylation patterns, and DNA-protein cross linking (Marnett, *Carcinogenesis* 21:361-370 (2000); Cerda et al., *Mutat. Res.* 386:141-152 (1997)). Copper, iron, and other transition metals, in the presence of reducing agents, catalyze the production of ROS such as superoxide ($O_2^{\bullet}$), hydrogen peroxide ($H_2O_2$) and the hydroxyl radical ($OH^{\bullet}$) through both the Haber-Weiss and Fenton reactions (Stoewe et al., *Free Radic. Biol. Med.* 3:97-105 (1987)). $OH^{\bullet}$ is considered the most reactive and damaging ROS and is capable of producing all the above DNA lesions (Marnett, *Carcinogenesis* 21:361-370 (2000)). Previous investigations have reported that $OH^{\bullet}$ induced, single- and double-strand DNA breaks occur during site-specific copper ion reactions in vitro and during excessive copper exposure in vivo (Chiu et al., *Biochemistry* 34:2653-2661 (1995); Kim et al., *Free Radic. Res.* 33:81-89 (2000); Hayashi et al., *Biochem. Biophys. Res. Comm.* 276:174-178, doi: 10.1006/bbrc.2000.3454 (2000)).

Telomeres, which are repeats of the hexanucleotide TTAGGG, exist at the ends of DNA to form a "protective cap" against degradation, chromosomal rearrangement, and allow the replication of DNA without the loss of genetic information (Reddel, *Carcinogenesis* 21:477-484 (2000)). The classical theory of cellular aging, or senescence, involves the telomere end replication problem (Olovnikov, *J. Theor. Biol.* 41:181-190 (1973)). DNA polymerase is unable to replicate the terminal end of the lagging strand during DNA replication resulting in the loss of 30-500 base pairs (Harley et al., *Nature* 345:458-460 (1990); von Zglinicki et al., *Exp. Cell Res.* 220:186-193, doi:10.1006/excr.1995.1305 (1995)). Somatic cells are unable to replace these lost telomeric repeats, leading to progressive telomere shortening during a cell's replicative life. Senescence is manifested when telomere length reaches a critical threshold (Reddel, *Carcinogenesis* 21:477-484 (2000)). Premature senescence has been documented in human fibroblasts exposed to oxidative stress (Chen et al., *Proc. Natl. Acad. Sci. USA* 91:4130-4134 (1994)). Examination of telomere length in fibroblasts after several population doublings under conditions of higher oxidative stress reveals shortened telomere lengths similar to senescence under normal conditions (von Zglinicki et al., *Exp. Cell Res.* 220:186-193, doi:10.1006/excr.1995.1305 (1995)). These data suggest that ROS-induced DNA damage in the telomere sequence may play an important role in telomere shortening.

In this study, the ability of Asp Ala His Lys [SEQ ID NO:1] to protect DNA and telomeres from ROS damage induced by copper coupled with ascorbic acid was examined.

A. Materials and Methods

Reagents: The synthetic D-analog of Asp Ala His Lys (D-Asp Ala His Lys) was obtained from Bowman Research Ltd. (Newport, Wales, UK). TeloTAGG Telomere Length Assay and X-ray film were purchased from Roche Molecular Biochemicals (Mannheim, Germany). DNeasy genomic isolation kits were purchased from Qiagen (Valencia, Calif.). Hybond-N+nylon membrane was ordered from Amersham Pharmacia Biotech (Piscataway, N.J.). All other chemicals were obtained from Sigma (St. Louis, Mo.).

DNA treatments: DNA strand breaks were measured using a modified method of Asaumi (Asaumi et al., *Biochem. Mol. Biol. Int.* 39:77-86 (1996)). Raji cells, a Burkitt lymphoma derived cell line (obtained from American Type Culture Collection (ATCC), Rockville, Md., ascension number CCL-86), were grown in Iscove's modified Dulbecco's medium (IMDM) with 10% fetal calf serum (FCS) at 10% $CO_2$ and 37° C. Genomic DNA was isolated using DNeasy spin columns (Qiagen) following the manufacturer's protocol. Then, 1 μg genomic DNA was incubated per reaction with $CuCl_2$, ascorbic acid, and/or the tetrapeptide in 10 mM sodium phosphate buffer, pH 7.4. Final concentrations were as follows: $CuCl_2$=10 μM, 25 μM, and 50 μM; ascorbic acid=25 μM, 50 μM, and 100 μM; D-Asp Ala His Lys=50 μM, 100 μM, and 200 μM. Total reaction volumes of 20 μl in 0.2 ml PCR tubes were incubated at 37° C. for 2 hours. Following the incubation, strand breaks were visualized by immediately adding 5 μl of loading dye [0.25% (w/v) bromophenol blue and 40% (w/v) sucrose] and loading on a 0.5% tris acetic acid EDTA (TAE) agarose gel. Gels were then run at 70V for 90 mM and stained using 2 μg/ml ethidium bromide for 30 minutes. Prior to photographing, gels were rinsed in TAE for 10 minutes.

Cell treatments: Raji cells were washed with PBS (10 mM phosphate buffered saline; 138 mM NaCl; 2.7 mM KCl pH 7.4). Then, 1.5×10⁶ cells were put into 5 ml PBS containing $CuCl_2$, ascorbic acid, and/or D-Asp Ala His Lys. Final concentrations were as follows: $CuCl_2$=10 μM, 25 μM, and 50 μM; ascorbic acid=100 μM, 250 μM, and 500 μM; D-Asp Ala His Lys=50 μM, 100 μM, and 200 μM. The cells were then incubated at 37° C. for 2 hours. Following the incubation, genomic DNA was isolated using DNeasy columns. DNA damage was visualized by 0.5% TAE agarose gel electrophoresis.

Telomere Length Assay: To examine telomere damage, the TeloTAGG Telomere Length Assay (Roche) was used according to manufacturer's recommendations: digesting 1 μg of genomic DNA per reaction using HinfI and RSA I. Samples were then run on a 0.8% TAE agarose gel at 70V for 2 hours. Southern blots were performed and probed using a digoxigenin (DIG) labeled telomere specific oligonucleotide. For cell treated samples, genomic DNA was used as described above. For DNA treated samples, reactions were setup as above, brought to 200 μl with PBS, and isolated using DNeasy columns prior to restriction digestions.

B. Results and Discussion

Copper ions, an essential part of chromatin (Dijkwel et al., *J. Cell Sci.* 84:53-67 (1986)), are present within DNA (Wacker et al., *J. Biol. Chem.* 234:3257-3262 (1959)) and may participate in oxidative DNA damage (Chiu et al., *Biochemistry* 34:2653-2661 (1995); Hayashi et al., *Biochem. Biophys. Res. Comm.* 276:174-178, doi:10.1006/bbrc.2000.3454 (2000); Kagawa et al., *J. Biol. Chem.* 266: 20175-20184 (1991)). In the presence of ascorbate or other reducing agents, copper can lead to the production of ROS by catalyzing the following reactions (Biaglow et al., *Free Radic. Biol. Med.* 22:1129-1138 (1997)):

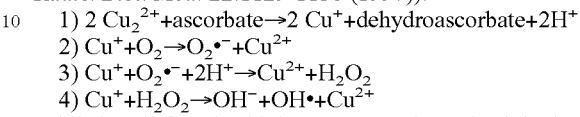

While iron is found at higher concentrations physiologically, oxidation by copper and $H_2O_2$ is 50 times faster than iron (Stoewe et al., *Free Radic. Biol. Med.* 3:97-105 (1987); Halliwell *J. Neurochem.* 59:1609-1623 (1992)). Due to the negative charge of the sugar phosphate backbone, cations can loosely bind DNA. Site-specific binding of copper ions within base pairs may be important to the regulation of DNA biosynthesis (Minchenkova et al., *Biopolymers* 5:615-625 (1967)). Unlike iron-catalyzed reactions, OH• scavengers do not prevent copper-mediated oxidative damage suggesting that oxidative DNA damage occurs in close proximity to the copper ions (Oikawa et al., *Biochim. Biophys. Acta* 1399:19-30 (1998)). The reactivity of OH• is so great that, presumably, OH• interactions only occur at or near the site of OH• production (Marnett, *Carcinogenesis,* 21, 361-370 (2000)). Oikawa, et. al., (Oikawa et al., *Biochim. Biophys. Acta* 1399: 19-30 (1998)) have shown that the following copper-mediated ROS reaction also occurs, and that the resulting DNA-copper-peroxide complex may be even more damaging to DNA than OH•:

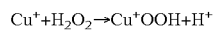

Figure 20:
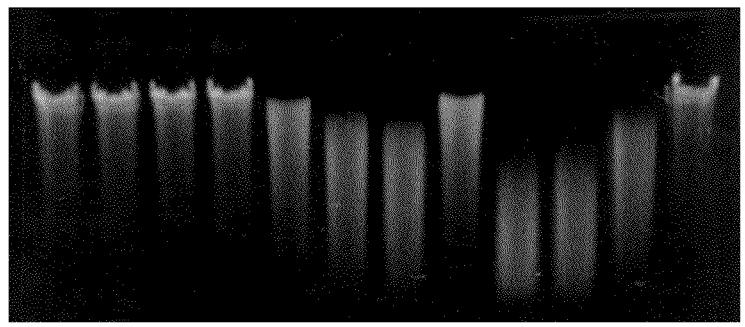
FIG. 20: TAE (tris acetic acid EDTA (ethylenediamine tetracetic acid)) agarose gel visualized with ethidium bromide showing attenuation of ROS-induced DNA double strand breaks in genomic DNA by D-Asp Ala His Lys. Lane 1—no treatment; Lane 2—$CuCl_2$, 50 μM; Lane 3—ascorbic acid, 100 μM; Lane 4—D-Asp Ala His Lys, 200 μM; Lane 5—$CuCl_2$, 10 μM+ascorbic acid, 50 μM; Lane 6—$CuCl_2$, 25 μM+ascorbic acid, 50 μM; Lane 7—$CuCl_2$, 50 μM+ascorbic acid, 50 μM; Lane 8—$CuCl_2$, 50 μM+ascorbic acid, 25 μM; Lane 9—$CuCl_2$, 50 μM+ascorbic acid, 100 μM; Lane 10—$CuCl_2$, 50 μM+ascorbic acid, 100 μM+D-Asp Ala His Lys, 50 μM; Lane 11—$CuCl_2$, 50 μM+ascorbic acid, 100 μM+D-Asp Ala His Lys, 100 μM; Lane 12—$CuCl_2$, 50 μM+ascorbic acid, 100 μM+D-Asp Ala His Lys, 200 μM.
Figure 21:
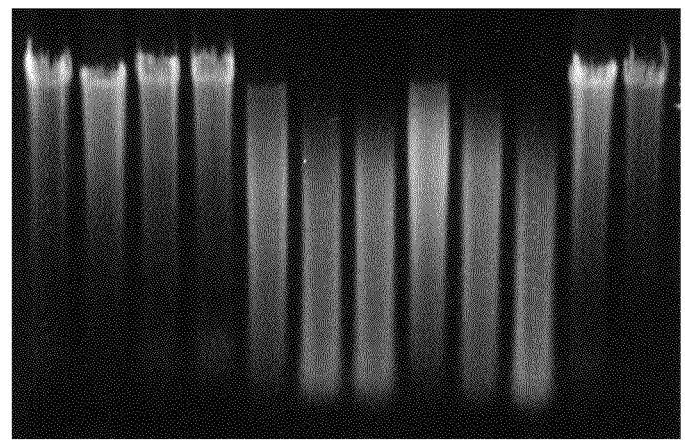
FIG. 21: TAE agarose gel visualized with ethidium bromide showing attenuation of ROS-induced DNA double strand breaks in genomic DNA by D-Asp Ala His Lys. Lane 1—no treatment; Lane 2—$CuCl_2$, 50 μM; Lane 3—ascorbic acid, 500 μM; Lane 4-D-Asp Ala His Lys, 200 μM; Lane 5—$CuCl_2$, 10 μM+ascorbic acid, 500 μM; Lane 6—$CuCl_2$, 25 μM+ascorbic acid, 500 μM; Lane 7—$CuCl_2$, 50 μM+ascorbic acid, 500 μM; Lane 8—$CuCl_2$, 50 μM+ascorbic acid, 100 μM; Lane 9—$CuCl_2$, 50 μM+ascorbic acid, 250 μM; Lane 10—$CuCl_2$, 50 μM+ascorbic acid, 500 μM+D-Asp Ala His Lys, 50 μM; Lane 11—$CuCl_2$, 50 μM+ascorbic acid, 500 μM+D-Asp Ala His Lys, 100 μM; Lane 12—$CuCl_2$, 50 μM+ascorbic acid, 500 μM+D-Asp Ala His Lys, 200 μM.

As expected, the results of the above-described experiments showed that copper and ascorbic acid alone were unable to cause strand breaks. When $CuCl_2$ and ascorbic acid were combined, a dose dependent accumulation of lower molecular weight DNA fragments was seen, the result of double strand breaks. These double strand breaks were attenuated by D-Asp Ala His Lys in a dose dependent manner (FIG. 20). At molar ratios of 1:1 (50 μM copper to 50 μM D-Asp Ala His Lys) and 1:2, some strand breaks were apparent. By elevating the ratio to 1:4, no strand breaks were detected. Similar results were observed in Raji cells treated with copper and ascorbic acid (FIG. 21). A lower ratio of 1:2 (copper to D-Asp Ala His Lys) provided complete protection to DNA in cell samples. It is reasonable to expect that DNA samples would require higher D-Asp Ala His Lys levels due to competition for copper with DNA and proximal OH• attack. The separation of DNA and copper would be critical in these samples necessitating the need for elevated D-Asp Ala His Lys. In cell samples, damage would be attributable to $H_2O_2$. $H_2O_2$ is freely diffusible, can penetrate to the nucleus, and has been shown to damage DNA in fibroblasts (Chen et al., *Proc. Natl. Acad. Sci. USA* 91:4130-4134 (1994); von Zglinicki et al., *Free Radic. Biol. Med.* 28:64-74 (2000)). Entrance of $H_2O_2$ into the cell may lead either to the formation of DNA peroxide complexes with native metals or to the release of sequestered metal stores that, combined with endogenous reducing agents (reduced glutathione (GSH), reduced nicotinamide dinucleotide (NADH), and ascorbic acid), would drive the production of OH•. One possible mechanism of D-Asp Ala His Lys protection would be the chelation of copper ions, thereby preventing production of OH• and $H_2O_2$. Another mode of protection may be the formation of D-Asp Ala His Lys-copper-peroxide complexes which would absorb the OH• damage rather than DNA, "mop-up" peroxides, and perhaps, in cell samples, keep $H_2O_2$ outside the cell.

Prior reports suggest that oxidative DNA damage may be directed at G-C rich areas, including telomeres. Rodriguez, et. al., reported that copper induced ROS damage primarily targeted DNA guanine (Rodriguez et al., *Cancer Res.* 57:2394-2403 (1997)). Strong, preferential binding of Cu (II) to the G-C pair has been reported at the N-7 and O-6 of the guanine bases plus the N-3 of cytosine (Kagawa et al., *J. Biol. Chem.* 266:20175-20184 (1991)). DNA peroxides complexes formed at these positions are believed to direct OH• attack to adjacent bases (Oikawa et al., *Biochim. Biophys. Acta* 1399: 19-30 (1998)). In addition, GGG in telomeric DNA has been shown to be sensitive to copper mediated ROS damage (Oikawa et al., *FEBS Lett.* 453:365-368 (1999)).

Figure 22:
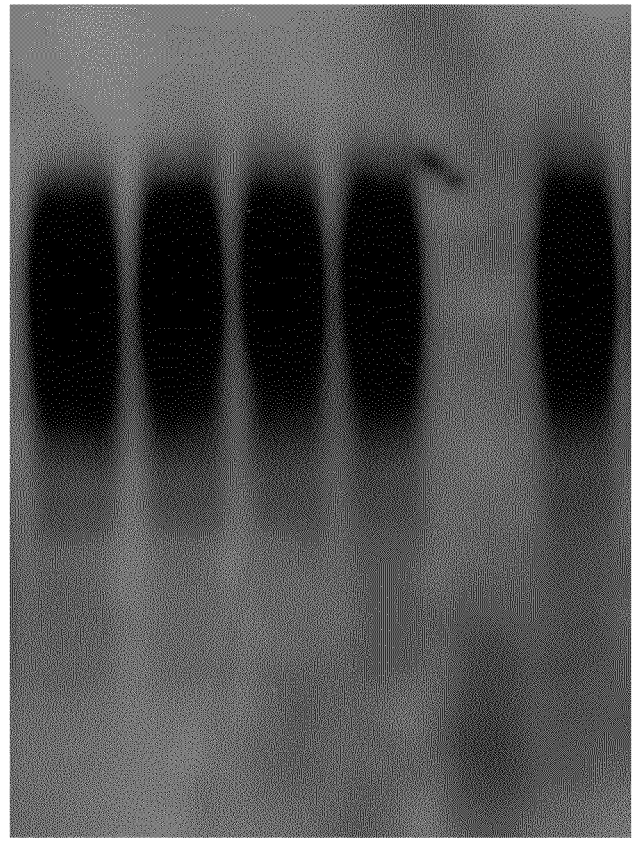
FIG. 22: Southern Blot showing attenuation of ROS-induced DNA double strand breaks in telomere DNA by D-Asp Ala His Lys. Lane 1—no treatment; Lane 2—CuCl$_2$, 50 µM; Lane 3—ascorbic acid, 100 µM, Lane 4—D-Asp Ala His Lys, 200 µM; Lane 5—CuCl$_2$, 50 µM+ascorbic acid, 100 µM; Lane 6—CuCl$_2$, 50 µM+ascorbic acid, 100 µM+D-Asp Ala His Lys, 200 µM.
Figure 23:
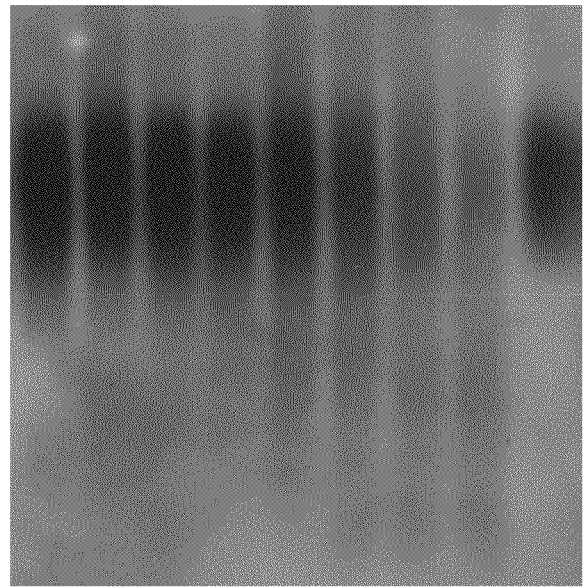
FIG. 23: Southern Blot showing attenuation of ROS-induced DNA double strand breaks in telomere DNA by D-Asp Ala His Lys. Lane 1—no treatment; Lane 2—CuCl$_2$, 50 µM; Lane 3—ascorbic acid, 500 µM; Lane 4—D-Asp Ala His Lys, 200 µM; Lane 5—CuCl$_2$, 50 µM+ascorbic acid, 100 µM; Lane 6—CuCl$_2$, 50 µM+ascorbic acid, 250 µM; Lane 7—CuCl$_2$, 50 µM+ascorbic acid, 500 µM; Lane 8—CuCl$_2$, 50 µM+ascorbic acid, 500 µM+D-Asp Ala His Lys, 50 µM; Lane 9—CuCl$_2$, 50 µM+ascorbic acid, 500 µM+D-Asp Ala His Lys, 100 µM.

Examination of the telomere in the genomic DNA samples in the present study showed double strand breaks in response to oxidative stress. DNA samples examined by Southern blot showed severely depleted and shortened telomere sequences (FIG. 22). Cell treatments showed damage to the telomere with some conservation of the sequence, even at the highest levels of copper and ascorbic acid used (FIG. 23), which may be attributed to ROS production outside the cells with the DNA sheltered inside the nucleus. D-Asp Ala His Lys protected the telomere from copper-mediated damage in these samples.

In addition to the double strand breaks detected in the experiments, other DNA lesions may be involved in ROS disease processes. Some cations, including copper, bound loosely to the phosphate backbone have been implicated in strand breaks while those coordinated in the helix cause base modifications (Marnett, *Carcinogenesis* 21:361-370 (2000); Rodriguez et al., *Cancer Res.* 57:2394-2403 (1997)). Episodes of increased copper and oxidative stress may direct DNA damage to G-C rich areas. In addition to telomeres, G-C rich areas exist at the 5' end of many genes (Bird, *Nature* 321:209-213 (1986)) hinting toward a site of oxidative damage involved in gene regulation. 8-Oxo-deoxyguanosine (8-oxo-dG) is a common DNA adduct produced by ROS, which can result in G→T point mutations widely seen in mutated oncogenes (Marnett, *Carcinogenesis* 21:361-370 (2000)). Conditions such as acidosis occurring during myocardial ischemia or alterations of ceruloplasmin have been shown to mobilize free copper to catalyze local oxidative tissue and DNA damage (Kim et al., *Free Radic. Res.* 33:81-89 (2000); Chevion et al., *Proc. Natl. Acad. Sci. USA* 90:1102-1106 (1993)). Levels of 8-oxo-dG are reported to be three to four times higher in the DNA of ischemic rat hearts than in controls (You et al., *J. Mol. Cell. Cardiol.* 32:1053-1059, doi:10.1006/jmcc.2000.1142 (2000)). In addition, chronic inflammation can produce areas of localized oxidative damage. Inflammatory cells, such as macrophages and neutrophils, release ROS that have been shown to damage the DNA of nearby cells (Shacter et al., *Carcinogenesis* 9:2297-2304 (1988)). Nitric oxide and superoxide released from activated leukocytes can lead to the production of peroxynitrite, which is more reactive with 8-oxo-dG than unmodified bases and possibly exacerbates the damage (Marnett, *Carcinogenesis* 21:361-370 (2000)).

C. Summary

Both DNA and the telomeric sequence are susceptible to copper-mediated ROS damage, particularly damage attributed to hydroxyl radicals. In this study, ROS-induced DNA double strand breaks and telomere shortening were produced by exposure to copper and ascorbic acid. D-Asp-Ala-His-Lys, a copper chelating tetrapeptide D-analog of the N-terminus of human albumin, attenuated DNA strand breaks in a dose dependent manner. The D-tetrapeptide, at a ratio of 4:1 (peptide:Cu), provided complete protection of isolated DNA and, at a ratio of 2:1 (peptide:Cu), completely protected Raji Burkitt cells' DNA exposed to copper/ascorbate. Southern blots of DNA treated with copper/ascorbate showed severe depletion and shortening of telomeres with some conservation of telomere sequences. The D-tetrapeptide provided complete telomere length protection at a ratio of 2:1 (peptide: Cu). While the exact mechanisms for ROS DNA damage have yet to be fully elucidated, D-Asp Ala His Lys inhibited copper-induced DNA double-strand breaks by ROS in both genomic DNA and in the telomere sequence.

Example 12

Inhibition of Angiogenesis

SPF research-grade fertilized eggs were obtained from Charles River Laboratories (800-772-3721). The eggs were candled to determine the position of the yolk and to mark the air cell with a pencil. Under sterile conditions, a small hole was drilled in the shell using a micro hand drill. The eggs were divided randomly into four groups, six eggs per group:

A—no injection;
B—100 µl of 7.0 mg/ml the peptide Asp Ala His Lys [SEQ ID NO:1] injected;
C—100 µl of 3.5 mg/ml the peptide Asp Ala His Lys [SEQ ID NO:1] injected; and
D—100 µl of water injected.

Injections were made into the yolk using a 0.5 ml syringe. The eggs were labeled at the time of injection with their group designations using a pencil. The holes in the injected eggs were sealed with candle wax, and the eggs were incubated in a Hova-Bator incubator (obtained from G.Q.F. Mfg. Co., Savannah, Ga.) set to 38° C. and 60-70% humidity (monitored by hygrometer inside incubator) for seven days. The eggs were incubated in trays with the small side down at a 30° angle. The eggs were turned six times per day to allow proper development. The eggs were candled every day for no more than 30 minutes total time out of the incubator, and any vascular development was noted.

At the end of the seven-day incubation period, a window was opened in the shell above the air cell using the following technique. The shell was cracked gently above the air cell using forceps. A few flakes of shell were removed with the forceps. The shell above the contents of the egg was removed using a pair of scissors. A drop of saline was placed on the opaque inner membrane. A morphometric analysis of angiogenesis in the chorioallantoic membranes was carried out, and the results are summarized in Table 12 below and were documented by digital photography.

TABLE 12

| Group | Total No. Eggs | No. Eggs Exhibiting Angiogenesis |
|---|---|---|
| A | 6 | 4 |
| B | 6 | 2 |
| C | 6 | 1 |
| D | 6 | 5 |

Nine of the twelve eggs injected with the peptide (groups B and C) did not develop a vascular system, whereas only three of twelve control eggs (groups A and D) failed to develop a vascular system. Statistical analysis of control eggs (groups A and D) versus treated eggs (groups B and C) showed that the difference in vascular development was statistically significant.

Example 13

Inhibition of IL-8 Release

Interleukin 8 (IL-8) is a pro-inflammatory cytokine and a potent chemoattractant and activator of neutrophils. It has also been reported to be a chemoattractant and activator of T-lymphocytes and eosinophils. IL-8 is produced by immune cells (including lymphocytes, neutrophils, monocytes and macrophages), fibroblasts and epithelial cells. Reports indicate an important role for IL-8 in the pathogenesis of respiratory viral infections, asthma, bronchitis, emphysema, cystic fibrosis, acute respiratory distress syndrome, sepsis, multiple organ dysfunction syndrome, and other inflammatory disorders.

The IL-8 release by Jurkat cells (American Type Culture Collection (ATCC), Rockville, Md.) exposed to copper and ascorbic acid (to produce ROS—see Examples 7, 10 and 11) was investigated. To do so, $1\times10^6$ Jurkat cells were incubated at 37° C. and 5% $CO_2$ in 0.5 ml IMDM medium (ATCC) (serum-free) with insulin transferin selenite solution (ITSS; Sigma) for 24 hours with the following additives.

Experiment 1:
a. None (control);
b. Asp Ala His Lys [SEQ ID NO:1] ("DAHK")—200 μM and ascorbic acid—500 μM;
c. $CuCl_2$—10 μM and ascorbic acid—500 μM;
d. $CuCl_2$—25 μM and ascorbic acid—500 μM;
e. $CuCl_2$—50 μM and ascorbic acid—500 μM;
f. $CuCl_2$—100 μM and ascorbic acid—500 μM;
g. $CuCl_2$—50 μM and DAHK—50 μM and ascorbic acid—500 μM;
h. $CuCl_2$—50 μM and DAHK—100 μM and ascorbic acid—500 μM; and
i. $CuCl_2$—50 μM and DAHK—200 μM and ascorbic acid—500 μM.

Experiment 2:
a. None (control);
b. $CuCl_2$—100 μM;
c. DAHK—200 μM and ascorbic acid—500 μM;
d. $CuCl_2$—25 μM and ascorbic acid—500 μM;
e. $CuCl_2$—50 μM and ascorbic acid—500 μM;
f. $CuCl_2$—100 μM and ascorbic acid—500 μM;
g. $CuCl_2$—50 μM and DAHK—50 μM and ascorbic acid—500 μM;
h. $CuCl_2$—50 μM and DAHK—100 μM and ascorbic acid—500 μM; and
i. $CuCl_2$—50 μM and DAHK—200 μM and ascorbic acid—500 μM.

Experiment 3:
a. None (control);
b. $CuCl_2$—100 μM;
c. DAHK—400 μM and ascorbic acid—250 μM;
d. $CuCl_2$—25 μM and ascorbic acid—250 μM;
e. $CuCl_2$—50 μM and ascorbic acid—250 μM;
f. $CuCl_2$—100 μM and ascorbic acid—250 μM;
h. $CuCl_2$—100 μM and DAHK—200 μM and ascorbic acid—250 μM; and
i. $CuCl_2$—100 μM and DAHK—400 μM and ascorbic acid—250 μM.

After the 24-hour incubation, supernatants were collected and the concentration of IL-8 in each supernatant was determined by an ELISA using human IL-8 matched pair antibodies (Endogen, Cambridge, Mass.). The ELISA was performed using an ELISA kit from Endogen, Cambridge, Mass. according to the manufacturer's instructions with the following exceptions: (1) coating antibody at 1 μg/ml; (2) detecting antibody 30 ng/ml; StrepAvidin HRP diluted 1:32,000.

Figure 24A:
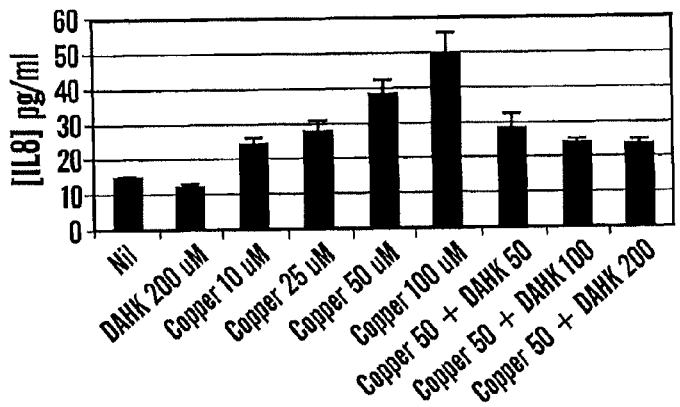
FIGS. 24A-C: Graphs of interleukin-8 (IL-8) concentration versus various treatments of Jurkat cells (all treatments, except nil and copper-only treatments, contained ascorbic acid in addition to the other additives listed on the graphs).
Figure 24B:
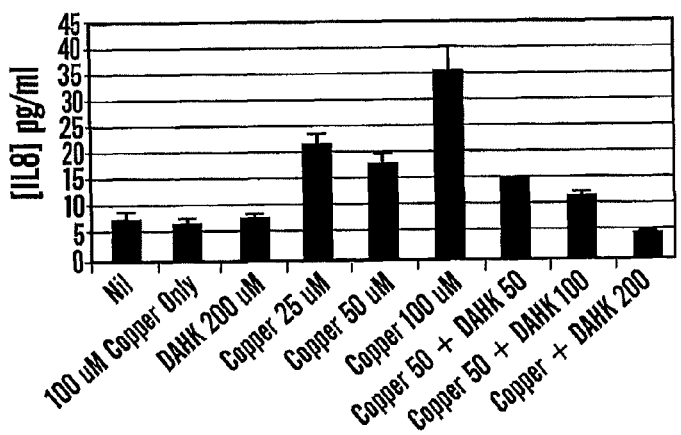
Figure 24C:
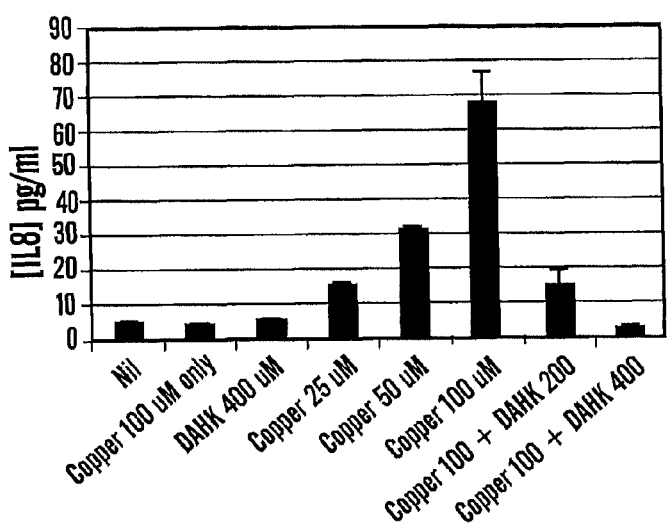

The results are presented in FIG. 24A (Experiment 1), FIG. 24B (Experiment 2), and FIG. 24 C (Experiment 3). As can be seen, copper and ascorbic acid caused the release of Il-8 from the cells in a dose-dependent manner. As can also be seen, DAHK inhibited the release of IL-8, with the best results being obtained with an 8:1 DAHK:Cu ratio.

Example 14

Inhibition of Oxidation of CoA

Coenzyme A (CoA) is essential for acetylation reactions in the body and, as a consequence, plays a critical role in the metabolism of carbohydrates and fatty acids. CoA can be oxidized to a disulfide which cannot participate in acetylation reactions. As a result, metabolism and energy utilization are inhibited.

In this example, it was investigated whether Cu(II) could oxidize CoA and, if so, whether the tetrapeptide Asp Ala His Lys [SEQ ID NO:1] (Bowman Research, Inc., United Kingdom) could protect CoA (Sigma) from oxidation by Cu(II). The experimental setup and results are presented in Table 13 below. All of the ingredients were added simultaneously and, after a 15-minute incubation, absorbance at 412 nm (A412) was measured. Free thiol groups were measured using DTNB. DTNB is dithionitrobenzoic acid (Sigma).

TABLE 13

|  | 1 | 2 | 3 | 4 | 5 | 6 | 7 |
|---|---|---|---|---|---|---|---|
| Asp Ala His Lys (2 mM) | 50 μl (190 μM) | 50 μl (190 μM) |  |  | 50 μl (190 μM) | 50 μl (190 μM) | 50 μl (190 μM) |
| CoA (2 mM) | 50 μl (190 μM) | 50 μl (190 μM) | 50 μl (190 μM) | 50 μl (190 μM) |  |  | 50 μl (190 μM) |
| $CuCl_2$ (1 mM) | 100 μl (190 μM) |  | 100 μl (190 μM) |  |  | 100 μl (190 μM) | 50 μl (85 μM) |
| Tris buffer, 50 mM, pH 8.0 | 200 μl | 300 μl | 250 μl | 350 μl | 350 μl | 250 μl | 250 μl |
| DTNB (3 mM) | 125 μl | 125 μl | 125 μl | 125 μl | 125 μl | 125 μl | 125 μl |
| A412 | 0.279 | 1.119 | 0.127 | 0.888 | 0.142 | 0.113 | 1.111 |

As can be seen from Table 13, Cu(II) oxidized CoA. As can also be seen, the tetrapeptide at a 1:1 tetrapeptide:Cu(II) ratio provided some protection of CoA, and the tetrapeptide at a 2:1 tetrapeptide:Cu(II) ratio provided 100% protection.

```
                             SEQUENCE LISTING

<160> NUMBER OF SEQ ID NOS: 9

<210> SEQ ID NO 1
<211> LENGTH: 4
<212> TYPE: PRT
<213> ORGANISM: Homo sapiens

<400> SEQUENCE: 1

Asp Ala His Lys
1

<210> SEQ ID NO 2
<211> LENGTH: 8
<212> TYPE: PRT
<213> ORGANISM: Artificial
<220> FEATURE:
<223> OTHER INFORMATION: metal
<220> FEATURE:
<221> NAME/KEY: METAL
<222> LOCATION: (1)..(8)
<223> OTHER INFORMATION: copper, nickel and other transition metals
<220> FEATURE:
<221> NAME/KEY: VARIANT
<222> LOCATION: (8)..(8)
<223> OTHER INFORMATION: Xaa = Orn

<400> SEQUENCE: 2

Asp Ala His Gly Gly His Ala Xaa
1               5

<210> SEQ ID NO 3
<211> LENGTH: 12
<212> TYPE: PRT
<213> ORGANISM: Homo sapiens

<400> SEQUENCE: 3

Asp Ala His Lys Ser Glu Val Ala His Arg Phe Lys
1               5                   10

<210> SEQ ID NO 4
<211> LENGTH: 11
<212> TYPE: PRT
<213> ORGANISM: Homo sapiens

<400> SEQUENCE: 4

Ala His Lys Ser Glu Val Ala His Arg Phe Lys
1               5                   10

<210> SEQ ID NO 5
<211> LENGTH: 10
<212> TYPE: PRT
<213> ORGANISM: Homo sapiens

<400> SEQUENCE: 5

His Lys Ser Glu Val Ala His Arg Phe Lys
1               5                   10

<210> SEQ ID NO 6
<211> LENGTH: 12
<212> TYPE: PRT
<213> ORGANISM: Homo sapiens
<220> FEATURE:
<221> NAME/KEY: MOD_RES
<222> LOCATION: (1)..(1)
```

```
<223> OTHER INFORMATION: ACETYLATION

<400> SEQUENCE: 6

Asp Ala His Lys Ser Glu Val Ala His Arg Phe Lys
1               5                   10

<210> SEQ ID NO 7
<211> LENGTH: 7
<212> TYPE: PRT
<213> ORGANISM: Homo sapiens
<220> FEATURE:
<221> NAME/KEY: UNSURE
<222> LOCATION: (1)..(7)
<223> OTHER INFORMATION: Xaa = any amino acid

<400> SEQUENCE: 7

Gly Met Xaa Cys Xaa Xaa Cys
1               5

<210> SEQ ID NO 8
<211> LENGTH: 7
<212> TYPE: PRT
<213> ORGANISM: Homo sapiens
<220> FEATURE:
<221> NAME/KEY: UNSURE
<222> LOCATION: (1)..(7)
<223> OTHER INFORMATION: Xaa = any amino acid

<400> SEQUENCE: 8

Gly Met Thr Cys Xaa Xaa Cys
1               5

<210> SEQ ID NO 9
<211> LENGTH: 7
<212> TYPE: PRT
<213> ORGANISM: Enterococcus hirae

<400> SEQUENCE: 9

Gly Met Thr Cys Ala Asn Cys
1               5
```

I claim:

1. A method of treating inflammation in an animal in need thereof comprising administering to the animal an effective amount of a metal-binding peptide which does not have a metal ion bound to it or of a physiologically-acceptable salt of the peptide, the sequence of the peptide being:

$$P_1-P_2,$$

wherein:

$P_1$ is:

$Xaa_1$ $Xaa_2$ His or $Xaa_1$ $Xaa_2$ His $Xaa_3$, the $P_1$ portion of the peptide being linear;

$Xaa_1$ is the N-terminal amino acid of the peptide, the only substituents on the α-amino group of $Xaa_1$ are hydrogen, and $Xaa_1$ is glycine, alanine, valine, leucine, isoleucine, serine, threonine, aspartic acid, asparagine, glutamic acid, glutamine, lysine, hydroxylysine, histidine, arginine, ornithine, phenylalanine, tyrosine, tryptophan, cysteine, methionine, or α-hydroxymethylserine;

$Xaa_2$ is alanine, β-alanine, valine, leucine, isoleucine, serine, threonine, aspartic acid, asparagine, glutamic acid, glutamine, lysine, hydroxylysine, histidine, arginine, ornithine, phenylalanine, tyrosine, tryptophan, cysteine, methionine, or α-hydroxymethylserine;

$Xaa_3$ is glycine, alanine, valine, lysine, arginine, ornithine, aspartic acid, glutamic acid, asparagine, glutamine or tryptophan; and $P_2$ is an amino acid sequence which comprises the sequence of a Cu(I) binding site, and $P_2$ contains no more than 10 amino acids.

2. The method of claim 1 wherein:

$Xaa_1$ is glycine, alanine, valine, leucine, isoleucine, serine, threonine, aspartic acid, glutamic acid, lysine, hydroxylysine, histidine, arginine, or α-hydroxymethylserine, and $Xaa_2$ is alanine, valine, leucine, isoleucine, threonine, serine, asparagine, glutamine, cysteine, methionine, lysine, hydroxylysine, histidine, arginine, or α-hydroxymethylserine.

3. The method of claim 1 wherein $Xaa_1$ is aspartic acid, glutamic acid, arginine, threonine or α-hydroxymethylserine.

4. The method of claim 1 wherein $Xaa_2$ is alanine, valine, leucine, isoleucine, threonine, serine, asparagine, methionine, histidine or α-hydroxymethylserine.

5. The method of claim 1 wherein $Xaa_3$ is lysine.

6. The method of claim 1 wherein:

$Xaa_1$ is aspartic acid, glutamic acid, arginine, lysine, threonine, serine or α-hydroxymethylserine, Xaa$_2$ is alanine, valine, leucine, isoleucine, threonine, serine, asparagine, methionine, histidine or α-hydroxymethylserine, and Xaa$_3$, when present, is lysine.

7. The method of claim 6 wherein Xaa$_1$ is aspartic acid or glutamic acid and Xaa$_2$ is alanine, valine, leucine, isoleucine, threonine, serine or α-hydroxymethylserine.

8. The method of claim 7 wherein Xaa$_2$ is alanine, valine, leucine or isoleucine.

9. The method of claim 8 wherein P$_1$ is Asp Ala His or Asp Ala His Lys.

10. The method of claim 9 wherein P$_1$ is Asp Ala His Lys.

11. The method of claim 6 wherein Xaa$_1$ is arginine, lysine, threonine, serine or α-hydroxymethylserine, and Xaa$_2$ is alanine, valine, leucine, isoleucine, threonine, serine or α-hydroxymethylserine.

12. The method of claim 11 wherein P$_1$ is Thr Leu His, HMS HMS His or Arg Thr His.

13. The method of claim 1 wherein P$_2$ comprises one of the following sequences:

```
Met Xaa4 Met,

Met Xaa4 Xaa4 Met,

Cys Cys,

Cys Xaa4 Cys,

Cys Xaa4 Xaa4 Cys,
```
-continued
```
Met Xaa4 Cys Xaa4 Xaa4 Cys,

Gly Met Xaa4 Cys Xaa4 Xaa4 Cys,    [SEQ ID NO: 7]

Gly Met Thr Cys Xaa4 Xaa4 Cys,     [SEQ ID NO: 8]

Gly Met Thr Cys Ala Asn Cys,       [SEQ ID NO: 9]
or

γ-Glu Cys Gly;
``` wherein Xaa$_4$ is any amino acid.

14. The method of claim 13 wherein P$_2$ is Gly Met Thr Cys Ala Asn Cys [SEQ ID NO:9].

15. The method of claim 1 wherein at least one of the amino acids of P$_1$ other than β-alanine or glycine, when present, is a D-amino acid.

16. The method of claim 1 wherein at least one of the amino acids of P$_2$ other than β-alanine or glycine, when present, is a D-amino acid.

17. The method of claim 15 wherein at least one of the amino acids of P$_2$ other than β-alanine or glycine, when present, is a D-amino acid.

18. The method of claim 1 wherein the terminal —COOH of P$_1$-P$_2$ is substituted to produce —COR$_2$, wherein R$_2$ is —NH$_2$, —NHR$_1$, —N(R$_1$)$_2$, —OR$_1$, or —R$_1$, wherein R$_1$ is an alkyl, aryl or heteroaryl.

19. The method of claim 13 wherein P$_1$ is Asp Ala His or Asp Ala His Lys.

20. The method of claim 14 wherein P$_1$ is Asp Ala His or Asp Ala His Lys.

* * * * *